(12) United States Patent
McClurken et al.

(10) Patent No.: US 7,998,140 B2
(45) Date of Patent: *Aug. 16, 2011

(54) FLUID-ASSISTED MEDICAL DEVICES, SYSTEMS AND METHODS

(75) Inventors: Michael E. McClurken, Durham, NH (US); Scott D. O'Brien, Sanford, ME (US)

(73) Assignee: Salient Surgical Technologies, Inc., Portsmouth, NH (US)

( * ) Notice: Subject to any disclaimer, the term of this patent is extended or adjusted under 35 U.S.C. 154(b) by 555 days.

This patent is subject to a terminal disclaimer.

(21) Appl. No.: 10/813,736

(22) Filed: Mar. 30, 2004

(65) Prior Publication Data

US 2005/0015085 A1 Jan. 20, 2005

Related U.S. Application Data

(63) Continuation of application No. 10/486,807, filed on Sep. 15, 2004, now abandoned, and a continuation of application No. PCT/US03/09763, filed on Mar. 27, 2003, application No. 10/813,736, and a continuation-in-part of application No. 10/365,170, filed on Feb. 11, 2003.

(60) Provisional application No. 60/453,093, filed on Mar. 6, 2003, provisional application No. 60/368,177, filed on Mar. 27, 2002, provisional application No. 60/356,390, filed on Feb. 12, 2002.

(51) Int. Cl.
*A61B 18/12* (2006.01)

(52) U.S. Cl. .......................................... 606/41; 606/49

(58) Field of Classification Search .................... 606/41, 606/45, 46, 48–50; 607/96, 104
See application file for complete search history.

(56) References Cited

U.S. PATENT DOCUMENTS

| | | | |
|---|---|---|---|
| 623,022 A | 4/1899 | Johnson |
| 1,735,271 A | 11/1929 | Groff |
| 1,814,791 A | 7/1931 | Ende |
| 2,002,594 A | 5/1935 | Wappler et al. |
| 2,031,682 A | 2/1936 | Wappler et al. |
| 2,102,270 A | 12/1937 | Hyams |

(Continued)

FOREIGN PATENT DOCUMENTS

DE 1 007 960 5/1957

(Continued)

OTHER PUBLICATIONS

TissueLink Monopolar Floating Ball™, Instructions for Use, 70-100001-001 Rev D, Effective Date: Jan. 25, 2001, 6 pages.

(Continued)

*Primary Examiner* — Henry M Johnson, III
*Assistant Examiner* — Aaron Roane
(74) *Attorney, Agent, or Firm* — Sterne, Kessler, Goldstein & Fox P.L.L.C.

(57) ABSTRACT

Surgical devices for treating tissue are provided. Also provided are systems for treating tissue and methods of treating tissue. An exemplary surgical device has a handle, a shaft extending from the handle having a distal end, and an electrode tip having an electrode surface with at least a portion of the electrode tip extending distally beyond the distal end of the shaft. In one embodiment, preferably the portion of the electrode tip extending distally beyond the distal end of the shaft comprises a cone shaped portion. The device also has a fluid passage being connectable to a fluid source and at least one fluid outlet opening in fluid communication with the fluid passage.

34 Claims, 39 Drawing Sheets

U.S. PATENT DOCUMENTS

| | | |
|---|---|---|
| 2,275,167 A | 3/1942 | Bierman |
| 2,888,928 A | 6/1959 | Seiger |
| 3,163,166 A | 12/1964 | Brant et al. |
| 3,682,130 A | 8/1972 | Jeffers |
| 3,750,650 A | 8/1973 | Ruttgers |
| 3,901,241 A | 8/1975 | Allen, Jr. |
| 4,037,590 A | 7/1977 | Dohring et al. |
| 4,060,088 A | 11/1977 | Morrison, Jr. et al. |
| 4,116,198 A | 9/1978 | Roos |
| 4,244,371 A | 1/1981 | Farin |
| 4,276,874 A | 7/1981 | Wolvek et al. |
| 4,301,802 A | 11/1981 | Poler |
| 4,307,720 A | 12/1981 | Weber, Jr. |
| 4,321,931 A | 3/1982 | Hon |
| 4,326,529 A | 4/1982 | Doss et al. |
| 4,342,218 A | 8/1982 | Fox |
| 4,355,642 A | 10/1982 | Alferness |
| 4,381,007 A | 4/1983 | Doss |
| 4,532,924 A | 8/1985 | Auth et al. |
| 4,548,207 A | 10/1985 | Reimels |
| 4,567,890 A | 2/1986 | Ohta et al. |
| 4,602,628 A | 7/1986 | Allen, Jr. |
| 4,671,274 A | 6/1987 | Sorochenko |
| 4,674,499 A | 6/1987 | Pao |
| 4,919,129 A | 4/1990 | Weber, Jr. |
| 4,920,982 A | 5/1990 | Goldstein |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,976,711 A | 12/1990 | Parins et al. |
| 4,985,030 A | 1/1991 | Melzer et al. |
| 4,998,933 A | 3/1991 | Eggers et al. |
| 5,009,656 A | 4/1991 | Reimels |
| 5,013,312 A | 5/1991 | Parins et al. |
| 5,035,696 A | 7/1991 | Rydell |
| 5,071,419 A | 12/1991 | Rydell et al. |
| 5,080,660 A | 1/1992 | Buelna |
| 5,122,138 A | 6/1992 | Manwaring |
| 5,125,928 A | 6/1992 | Parins et al. |
| 5,147,357 A | 9/1992 | Rose et al. |
| 5,151,102 A | 9/1992 | Kamiyama et al. |
| 5,156,613 A | 10/1992 | Sawyer |
| 5,167,659 A | 12/1992 | Ohtomo et al. |
| 5,171,311 A | 12/1992 | Rydell et al. |
| 5,190,541 A | 3/1993 | Abele et al. |
| 5,195,959 A | 3/1993 | Smith |
| 5,197,963 A | 3/1993 | Parins |
| 5,197,964 A | 3/1993 | Parins |
| 5,217,460 A | 6/1993 | Knoepfler |
| 5,234,428 A | 8/1993 | Kaufman |
| 5,242,441 A | 9/1993 | Avitall |
| 5,242,442 A | 9/1993 | Hirschfeld |
| 5,254,117 A | 10/1993 | Rigby |
| 5,269,780 A | 12/1993 | Roos |
| 5,269,781 A | 12/1993 | Hewell, III |
| 5,277,696 A | 1/1994 | Hagen |
| 5,281,215 A | 1/1994 | Milder |
| 5,281,216 A | 1/1994 | Klicek |
| 5,282,799 A | 2/1994 | Rydell |
| 5,290,286 A | 3/1994 | Parins |
| 5,300,087 A | 4/1994 | Knoepfler |
| 5,313,943 A | 5/1994 | Houser et al. |
| 5,318,589 A | 6/1994 | Lichtman |
| 5,322,503 A | 6/1994 | Desai |
| 5,330,521 A | 7/1994 | Cohen |
| 5,334,193 A | 8/1994 | Nardella |
| 5,336,220 A | 8/1994 | Ryan |
| 5,342,357 A | 8/1994 | Nardella |
| 5,342,359 A | 8/1994 | Rydell |
| 5,348,554 A | 9/1994 | Imran et al. |
| 5,364,394 A | 11/1994 | Mehl |
| 5,383,874 A | 1/1995 | Jackson et al. |
| 5,383,876 A | 1/1995 | Nardella |
| 5,395,312 A * | 3/1995 | Desai ............................ 604/22 |
| 5,395,363 A | 3/1995 | Billings et al. |
| 5,401,272 A | 3/1995 | Perkins |
| 5,403,311 A | 4/1995 | Abele et al. |
| 5,403,312 A | 4/1995 | Yates et al. |
| 5,405,344 A | 4/1995 | Williamson et al. |
| 5,405,376 A | 4/1995 | Mulier et al. |
| 5,417,672 A | 5/1995 | Nita et al. |
| 5,417,709 A | 5/1995 | Slater |
| 5,431,168 A | 7/1995 | Webster, Jr. |
| 5,431,649 A | 7/1995 | Mulier et al. |
| 5,433,708 A | 7/1995 | Nichols et al. |
| 5,437,662 A | 8/1995 | Nardella |
| 5,437,664 A | 8/1995 | Cohen et al. |
| 5,441,498 A | 8/1995 | Perkins |
| 5,441,503 A | 8/1995 | Considine et al. |
| 5,445,638 A | 8/1995 | Rydell et al. |
| 5,456,682 A | 10/1995 | Edwards et al. |
| 5,456,684 A | 10/1995 | Schmidt et al. |
| 5,458,596 A | 10/1995 | Lax et al. |
| 5,458,597 A | 10/1995 | Edwards et al. |
| 5,458,598 A | 10/1995 | Feinberg et al. |
| 5,460,629 A | 10/1995 | Shlain et al. |
| 5,462,521 A | 10/1995 | Brucker et al. |
| 5,472,441 A | 12/1995 | Edwards et al. |
| 5,472,443 A | 12/1995 | Cordis et al. |
| 5,487,385 A | 1/1996 | Avitall |
| 5,490,819 A | 2/1996 | Nicholas et al. |
| 5,500,012 A | 3/1996 | Brucker et al. |
| 5,514,130 A | 5/1996 | Baker |
| 5,522,815 A | 6/1996 | Durgin, Jr. et al. |
| 5,536,267 A | 7/1996 | Edwards et al. |
| 5,540,562 A | 7/1996 | Giter |
| 5,542,928 A | 8/1996 | Evans et al. |
| 5,542,945 A | 8/1996 | Fritzsch |
| 5,556,397 A | 9/1996 | Long |
| 5,558,671 A | 9/1996 | Yates |
| 5,562,503 A | 10/1996 | Ellman et al. |
| 5,562,702 A | 10/1996 | Huitema et al. |
| 5,562,703 A | 10/1996 | Desai |
| 5,564,440 A | 10/1996 | Swartz et al. |
| 5,569,242 A | 10/1996 | Lax et al. |
| 5,569,243 A | 10/1996 | Kortenbach et al. |
| 5,573,424 A | 11/1996 | Poppe |
| 5,573,533 A | 11/1996 | Strul |
| 5,575,810 A | 11/1996 | Swanson et al. |
| 5,584,872 A | 12/1996 | LaFontaine et al. |
| 5,599,346 A | 2/1997 | Edwards et al. |
| 5,599,350 A | 2/1997 | Schulze et al. |
| 5,605,539 A | 2/1997 | Buelna et al. |
| 5,609,151 A | 3/1997 | Mulier et al. |
| 5,633,578 A | 5/1997 | Eggers et al. |
| 5,637,110 A | 6/1997 | Pennybacker et al. |
| 5,640,955 A | 6/1997 | Ockuly et al. |
| 5,643,197 A | 7/1997 | Brucker et al. |
| 5,647,869 A | 7/1997 | Goble et al. |
| 5,647,871 A | 7/1997 | Levine et al. |
| 5,653,692 A | 8/1997 | Masterson et al. |
| 5,660,836 A | 8/1997 | Knowlton |
| 5,676,662 A | 10/1997 | Fleischhacker et al. |
| 5,676,693 A | 10/1997 | LaFontaine |
| 5,681,282 A | 10/1997 | Eggers et al. |
| 5,681,294 A | 10/1997 | Osborne et al. |
| 5,683,366 A | 11/1997 | Eggers et al. |
| 5,683,384 A | 11/1997 | Gough et al. |
| 5,687,723 A | 11/1997 | Avitall |
| 5,688,270 A | 11/1997 | Yates et al. |
| 5,693,045 A | 12/1997 | Eggers |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,702,386 A | 12/1997 | Stern et al. |
| 5,709,680 A | 1/1998 | Yates et al. |
| 5,713,896 A | 2/1998 | Nardella |
| 5,718,241 A | 2/1998 | Ben-Haim et al. |
| 5,718,701 A | 2/1998 | Shai et al. |
| 5,718,703 A | 2/1998 | Chin |
| 5,722,400 A | 3/1998 | Ockuly et al. |
| 5,725,524 A | 3/1998 | Mulier et al. |
| 5,730,127 A | 3/1998 | Avitall |
| 5,735,846 A | 4/1998 | Panescu et al. |

| | | | | | | |
|---|---|---|---|---|---|---|
| 5,743,903 A | 4/1998 | Stern et al. | 6,016,809 A | 1/2000 | Mulier et al. | |
| 5,746,739 A | 5/1998 | Sutter | 6,017,338 A | 1/2000 | Brucker et al. | |
| 5,749,869 A | 5/1998 | Lindenmeier et al. | 6,018,676 A | 1/2000 | Davis et al. | |
| 5,755,717 A | 5/1998 | Yates et al. | 6,019,757 A | 2/2000 | Scheldrup | |
| 5,755,753 A | 5/1998 | Knowlton | 6,024,733 A | 2/2000 | Eggers et al. | |
| 5,766,153 A | 6/1998 | Eggers et al. | 6,027,501 A | 2/2000 | Goble et al. | |
| 5,766,167 A | 6/1998 | Eggers et al. | 6,030,379 A | 2/2000 | Panescu et al. | |
| 5,785,705 A | 7/1998 | Baker | 6,030,381 A * | 2/2000 | Jones et al. | 606/41 |
| 5,785,706 A | 7/1998 | Bednarek | 6,032,077 A | 2/2000 | Pomeranz | |
| 5,792,140 A | 8/1998 | Tu et al. | 6,032,674 A | 3/2000 | Eggers et al. | |
| 5,797,905 A | 8/1998 | Fleischman et al. | 6,033,398 A | 3/2000 | Farley et al. | |
| 5,797,960 A | 8/1998 | Stevens et al. | 6,035,238 A | 3/2000 | Ingle et al. | |
| 5,800,413 A | 9/1998 | Swartz et al. | 6,036,687 A | 3/2000 | Laufer et al. | |
| 5,800,482 A | 9/1998 | Pomeranz | 6,045,532 A | 4/2000 | Eggers et al. | |
| 5,807,393 A | 9/1998 | Williamson et al. | 6,047,700 A | 4/2000 | Eggers et al. | |
| 5,807,395 A | 9/1998 | Mulier et al. | 6,048,333 A | 4/2000 | Lennox et al. | |
| 5,810,764 A | 9/1998 | Eggers et al. | 6,053,172 A | 4/2000 | Hovda et al. | |
| 5,810,805 A | 9/1998 | Sutcu et al. | 6,053,912 A | 4/2000 | Panescu et al. | |
| 5,810,811 A | 9/1998 | Yates et al. | 6,056,744 A | 5/2000 | Edwards | |
| 5,817,093 A | 10/1998 | Williamson et al. | 6,056,745 A | 5/2000 | Panescu et al. | |
| 5,823,956 A | 10/1998 | Roth et al. | 6,056,746 A | 5/2000 | Goble et al. | |
| 5,827,271 A | 10/1998 | Buysse et al. | 6,056,747 A | 5/2000 | Saadat et al. | |
| 5,827,281 A | 10/1998 | Levin | 6,059,781 A | 5/2000 | Yamanashi et al. | |
| 5,833,703 A | 11/1998 | Manushakian | 6,063,079 A | 5/2000 | Hovda et al. | |
| 5,843,019 A | 12/1998 | Eggers et al. | 6,063,081 A | 5/2000 | Mulier et al. | |
| 5,843,021 A | 12/1998 | Edwards et al. | 6,066,134 A | 5/2000 | Eggers et al. | |
| 5,843,078 A | 12/1998 | Sharkey | 6,066,139 A | 5/2000 | Ryan et al. | |
| 5,843,152 A | 12/1998 | Tu et al. | 6,068,627 A | 5/2000 | Orszulak et al. | |
| 5,855,614 A | 1/1999 | Stevens et al. | 6,068,653 A | 5/2000 | LaFontaine | |
| 5,860,951 A | 1/1999 | Eggers et al. | 6,071,280 A | 6/2000 | Edwards et al. | |
| 5,860,974 A | 1/1999 | Abele | 6,073,051 A | 6/2000 | Sharkey et al. | |
| 5,861,002 A | 1/1999 | Desai | 6,074,389 A | 6/2000 | Levine et al. | |
| 5,861,021 A | 1/1999 | Thome et al. | 6,080,151 A | 6/2000 | Swartz et al. | |
| 5,868,739 A | 2/1999 | Lindenmeier et al. | 6,081,749 A | 6/2000 | Ingle et al. | |
| 5,871,469 A | 2/1999 | Eggers et al. | 6,083,237 A | 7/2000 | Huitema et al. | |
| 5,871,524 A | 2/1999 | Knowlton | 6,086,585 A | 7/2000 | Hovda et al. | |
| 5,873,855 A * | 2/1999 | Eggers et al. ... 604/114 | 6,086,586 A | 7/2000 | Hooven | |
| 5,876,398 A | 3/1999 | Mulier et al. | 6,091,995 A | 7/2000 | Ingle et al. | |
| 5,879,348 A | 3/1999 | Owens et al. | 6,093,186 A | 7/2000 | Goble | |
| 5,888,198 A | 3/1999 | Eggers et al. | 6,095,149 A | 8/2000 | Sharkey et al. | |
| 5,891,095 A | 4/1999 | Eggers et al. | 6,096,037 A | 8/2000 | Mulier et al. | |
| 5,891,141 A | 4/1999 | Rydell | 6,099,514 A | 8/2000 | Sharkey et al. | |
| 5,891,142 A | 4/1999 | Eggers et al. | 6,102,046 A | 8/2000 | Weinstein et al. | |
| 5,893,848 A | 4/1999 | Negus et al. | 6,105,581 A | 8/2000 | Eggers et al. | |
| 5,895,355 A | 4/1999 | Schaer | 6,109,268 A | 8/2000 | Thapliyal et al. | |
| 5,895,417 A | 4/1999 | Pomeranz et al. | 6,113,596 A | 9/2000 | Hooven et al. | |
| 5,897,553 A | 4/1999 | Mulier et al. | 6,113,597 A | 9/2000 | Eggers et al. | |
| 5,902,272 A | 5/1999 | Eggers et al. | 6,117,109 A | 9/2000 | Eggers et al. | |
| 5,902,328 A | 5/1999 | LaFontaine et al. | 6,122,549 A | 9/2000 | Sharkey et al. | |
| 5,904,711 A | 5/1999 | Flom et al. | H1904 H | 10/2000 | Yates et al. | |
| 5,906,613 A | 5/1999 | Mulier et al. | 6,126,682 A | 10/2000 | Sharkey et al. | |
| 5,913,854 A | 6/1999 | Maguire et al. | 6,135,999 A | 10/2000 | Fanton et al. | |
| 5,913,856 A | 6/1999 | Chia et al. | 6,141,576 A | 10/2000 | Littmann et al. | |
| 5,919,191 A | 7/1999 | Lennox et al. | 6,142,992 A | 11/2000 | Cheng et al. | |
| 5,919,219 A | 7/1999 | Knowlton | 6,149,620 A | 11/2000 | Baker et al. | |
| 5,921,982 A | 7/1999 | Lesh et al. | 6,159,194 A | 12/2000 | Eggers et al. | |
| 5,921,983 A | 7/1999 | Shannon, Jr. | 6,159,208 A | 12/2000 | Hovda et al. | |
| 5,925,045 A | 7/1999 | Reimels et al. | 6,165,169 A | 12/2000 | Panescu et al. | |
| 5,935,123 A | 8/1999 | Edwards et al. | 6,165,175 A | 12/2000 | Wampler et al. | |
| 5,944,715 A | 8/1999 | Goble et al. | 6,168,594 B1 | 1/2001 | LaFontaine et al. | |
| 5,948,011 A | 9/1999 | Knowlton | 6,171,275 B1 | 1/2001 | Webster, Jr. | |
| 5,951,549 A | 9/1999 | Richardson et al. | 6,174,308 B1 | 1/2001 | Goble et al. | |
| 5,954,716 A | 9/1999 | Sharkey et al. | 6,174,309 B1 | 1/2001 | Wrublewski et al. | |
| 5,957,919 A | 9/1999 | Laufer | 6,176,857 B1 | 1/2001 | Ashley | |
| 5,964,755 A | 10/1999 | Edwards | 6,179,824 B1 | 1/2001 | Eggers et al. | |
| 5,971,983 A | 10/1999 | Lesh | 6,179,836 B1 | 1/2001 | Eggers et al. | |
| 5,976,128 A | 11/1999 | Schilling et al. | 6,183,469 B1 | 2/2001 | Thapliyal et al. | |
| 5,980,504 A | 11/1999 | Sharkey et al. | 6,190,381 B1 | 2/2001 | Olsen et al. | |
| 5,980,516 A | 11/1999 | Mulier et al. | 6,190,384 B1 | 2/2001 | Ouchi | |
| 5,989,248 A | 11/1999 | Tu et al. | 6,193,715 B1 | 2/2001 | Wrublewski et al. | |
| 5,992,418 A | 11/1999 | de la Rama et al. | 6,193,716 B1 | 2/2001 | Shannon, Jr. | |
| 5,993,412 A | 11/1999 | Deily et al. | 6,203,542 B1 | 3/2001 | Ellsberry et al. | |
| 6,003,517 A | 12/1999 | Sheffield et al. | 6,210,402 B1 | 4/2001 | Olsen et al. | |
| 6,004,316 A | 12/1999 | Laufer | 6,210,406 B1 | 4/2001 | Webster | |
| 6,004,319 A | 12/1999 | Goble et al. | 6,210,410 B1 | 4/2001 | Farin et al. | |
| 6,007,570 A | 12/1999 | Sharkey et al. | 6,210,411 B1 | 4/2001 | Hofmann et al. | |
| 6,010,500 A | 1/2000 | Sherman et al. | 6,212,426 B1 | 4/2001 | Swanson | |
| 6,015,391 A | 1/2000 | Rishton et al. | 6,216,704 B1 | 4/2001 | Ingle et al. | |
| 6,015,407 A | 1/2000 | Rieb et al. | 6,217,576 B1 | 4/2001 | Tu et al. | |

| Patent No. | Date | Inventor(s) |
|---|---|---|
| 6,221,039 B1 | 4/2001 | Durgin et al. |
| 6,221,069 B1 | 4/2001 | Daikuzono |
| 6,224,592 B1 | 5/2001 | Eggers et al. |
| 6,224,593 B1 | 5/2001 | Ryan et al. |
| 6,226,554 B1 | 5/2001 | Tu et al. |
| 6,228,078 B1 | 5/2001 | Eggers et al. |
| 6,228,082 B1 | 5/2001 | Baker et al. |
| 6,231,591 B1 | 5/2001 | Desai |
| 6,235,020 B1 | 5/2001 | Cheng et al. |
| 6,236,891 B1 | 5/2001 | Ingle et al. |
| 6,238,387 B1 | 5/2001 | Miller, III |
| 6,238,391 B1 | 5/2001 | Olsen et al. |
| 6,238,393 B1 | 5/2001 | Mulier et al. |
| 6,241,753 B1 | 6/2001 | Knowlton |
| 6,241,754 B1 | 6/2001 | Swanson et al. |
| 6,251,110 B1 | 6/2001 | Wampler |
| 6,254,600 B1 | 7/2001 | Willink et al. |
| 6,258,086 B1 | 7/2001 | Ashley et al. |
| 6,258,087 B1 | 7/2001 | Edwards et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,654 B1 | 7/2001 | Swartz et al. |
| 6,266,551 B1 | 7/2001 | Osadchy et al. |
| 6,277,112 B1 | 8/2001 | Underwood et al. |
| 6,280,440 B1 | 8/2001 | Gocho |
| 6,283,961 B1 | 9/2001 | Underwood et al. |
| 6,283,988 B1 | 9/2001 | Laufer et al. |
| 6,283,989 B1 | 9/2001 | Laufer et al. |
| 6,290,715 B1 | 9/2001 | Sharkey et al. |
| 6,293,942 B1 | 9/2001 | Goble et al. |
| 6,293,945 B1 | 9/2001 | Parins et al. |
| 6,296,636 B1 | 10/2001 | Cheng et al. |
| 6,296,638 B1 | 10/2001 | Davison et al. |
| 6,296,640 B1 | 10/2001 | Wampler et al. |
| 6,299,633 B1 | 10/2001 | Laufer |
| 6,302,903 B1 | 10/2001 | Mulier et al. |
| 6,306,134 B1 | 10/2001 | Goble et al. |
| 6,309,387 B1 | 10/2001 | Eggers et al. |
| 6,311,090 B1 | 10/2001 | Knowlton |
| 6,312,408 B1 | 11/2001 | Eggers et al. |
| 6,312,430 B1 | 11/2001 | Wilson et al. |
| 6,315,777 B1 | 11/2001 | Comben |
| 6,322,549 B1 | 11/2001 | Eggers et al. |
| 6,322,559 B1 | 11/2001 | Daulton et al. |
| 6,327,505 B1 | 12/2001 | Medhkour et al. |
| 6,328,735 B1 | 12/2001 | Curley et al. |
| 6,328,736 B1 | 12/2001 | Mulier et al. |
| 6,336,926 B1 | 1/2002 | Goble |
| 6,350,262 B1 | 2/2002 | Ashley |
| 6,350,276 B1 | 2/2002 | Knowlton |
| 6,352,533 B1 | 3/2002 | Ellman et al. |
| 6,355,032 B1 | 3/2002 | Hovda et al. |
| 6,358,245 B1 | 3/2002 | Edwards et al. |
| 6,358,248 B1 | 3/2002 | Mulier et al. |
| 6,363,937 B1 | 4/2002 | Hovda et al. |
| 6,371,956 B1 | 4/2002 | Wilson et al. |
| 6,379,350 B1 | 4/2002 | Sharkey et al. |
| 6,379,351 B1 | 4/2002 | Thapliyal et al. |
| 6,391,025 B1 | 5/2002 | Weinstein et al. |
| 6,391,028 B1 | 5/2002 | Fanton et al. |
| 6,402,742 B1 | 6/2002 | Blewett et al. |
| 6,409,722 B1 | 6/2002 | Hoey et al. |
| 6,409,723 B1 | 6/2002 | Edwards |
| H2037 H | 7/2002 | Yates et al. |
| 6,416,507 B1 | 7/2002 | Eggers et al. |
| 6,416,508 B1 | 7/2002 | Eggers et al. |
| 6,416,509 B1 | 7/2002 | Goble et al. |
| 6,419,509 B2 | 7/2002 | Cho |
| 6,425,877 B1 | 7/2002 | Edwards |
| 6,432,103 B1 | 8/2002 | Ellsberry et al. |
| 6,440,130 B1 | 8/2002 | Mulier et al. |
| 6,443,952 B1 | 9/2002 | Mulier et al. |
| 6,447,509 B1 | 9/2002 | Bonnet et al. |
| 6,451,017 B1 | 9/2002 | Moutafis et al. |
| 6,458,123 B1 | 10/2002 | Brucker et al. |
| 6,458,130 B1 | 10/2002 | Frazier et al. |
| 6,461,350 B1 | 10/2002 | Underwood et al. |
| 6,461,354 B1 | 10/2002 | Olsen et al. |
| 6,461,357 B1 | 10/2002 | Sharkey et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,275 B1 | 10/2002 | Wampler et al. |
| 6,471,698 B1 | 10/2002 | Edwards et al. |
| 6,475,216 B2 | 11/2002 | Mulier et al. |
| 6,478,793 B1 | 11/2002 | Cosman et al. |
| 6,482,202 B1 | 11/2002 | Goble et al. |
| 6,485,490 B2 | 11/2002 | Wampler et al. |
| 6,488,680 B1 | 12/2002 | Francischelli et al. |
| 6,493,589 B1 | 12/2002 | Medhkour et al. |
| 6,494,902 B2 | 12/2002 | Hoey et al. |
| 6,497,704 B2 | 12/2002 | Ein-Gal |
| 6,497,705 B2 | 12/2002 | Comben |
| 6,506,189 B1 | 1/2003 | Rittman, III et al. |
| 6,508,815 B1 | 1/2003 | Strul et al. |
| 6,517,536 B2 | 2/2003 | Hooven et al. |
| 6,526,320 B2 | 2/2003 | Mitchell |
| 6,537,248 B2 | 3/2003 | Mulier et al. |
| 6,537,272 B2 | 3/2003 | Christopherson et al. |
| 6,539,265 B2 | 3/2003 | Medhkour et al. |
| 6,558,379 B1 | 5/2003 | Batchelor et al. |
| 6,558,385 B1 | 5/2003 | McClurken et al. |
| 6,575,969 B1 | 6/2003 | Rittman, III et al. |
| 6,577,902 B1 | 6/2003 | Laufer et al. |
| 6,579,288 B1 | 6/2003 | Swanson et al. |
| 6,585,732 B2 | 7/2003 | Mulier et al. |
| 6,602,248 B1 | 8/2003 | Sharps et al. |
| 6,603,988 B2 | 8/2003 | Dowlatshahi |
| 6,610,060 B2 | 8/2003 | Mulier et al. |
| 6,613,048 B2 | 9/2003 | Mulier et al. |
| 6,623,515 B2 | 9/2003 | Mulier et al. |
| 6,626,899 B2 | 9/2003 | Houser et al. |
| 6,635,034 B1 | 10/2003 | Cosmescu |
| 6,645,202 B1 | 11/2003 | Pless et al. |
| 6,666,862 B2 | 12/2003 | Jain et al. |
| 6,669,692 B1 | 12/2003 | Nelson et al. |
| 6,676,660 B2 | 1/2004 | Wampler |
| 6,679,882 B1 | 1/2004 | Kornerup |
| 6,682,501 B1 | 1/2004 | Nelson et al. |
| 6,682,527 B2 | 1/2004 | Strul |
| 6,682,528 B2 | 1/2004 | Frazier et al. |
| 6,685,700 B2 | 2/2004 | Behl et al. |
| 6,685,701 B2 | 2/2004 | Orszulak et al. |
| 6,685,704 B2 | 2/2004 | Greep |
| 6,689,129 B2 | 2/2004 | Baker |
| 6,689,131 B2 | 2/2004 | McClurken |
| 6,692,489 B1 | 2/2004 | Heim et al. |
| 6,694,984 B2 | 2/2004 | Habib |
| 6,695,837 B2 | 2/2004 | Howell |
| 6,695,840 B2 | 2/2004 | Schulze |
| 6,699,240 B2 | 3/2004 | Francischelli |
| 6,699,242 B2 | 3/2004 | Heggeness |
| 6,699,244 B2 | 3/2004 | Carranza et al. |
| 6,699,268 B2 | 3/2004 | Kordis et al. |
| 6,702,810 B2 | 3/2004 | McClurken et al. |
| 6,702,812 B2 | 3/2004 | Cosmescu |
| 6,706,039 B2 | 3/2004 | Mulier et al. |
| 6,712,074 B2 | 3/2004 | Edwards et al. |
| 6,712,811 B2 | 3/2004 | Underwood et al. |
| 6,712,813 B2 | 3/2004 | Ellman et al. |
| 6,712,816 B2 | 3/2004 | Hung et al. |
| 6,716,211 B2 | 4/2004 | Mulier et al. |
| 6,719,754 B2 | 4/2004 | Underwood et al. |
| 6,723,094 B2 | 4/2004 | Desinger |
| 6,726,683 B1 | 4/2004 | Shaw |
| 6,726,684 B1 | 4/2004 | Woloszko et al. |
| 6,726,686 B2 | 4/2004 | Buysse et al. |
| 6,730,081 B1 | 5/2004 | Desai |
| 6,733,496 B2 | 5/2004 | Sharkey et al. |
| 6,733,498 B2 | 5/2004 | Paton et al. |
| 6,733,501 B2 | 5/2004 | Levine |
| 6,736,810 B2 | 5/2004 | Hoey et al. |
| 6,740,058 B2 | 5/2004 | Lal et al. |
| 6,740,079 B1 | 5/2004 | Eggers et al. |
| 6,740,082 B2 | 5/2004 | Shadduck |
| 6,740,084 B2 | 5/2004 | Ryan |

| Patent | Date | Name |
|---|---|---|
| 6,740,102 B2 | 5/2004 | Hess et al. |
| 6,743,197 B1 | 6/2004 | Edwards |
| 6,743,229 B2 | 6/2004 | Buysse et al. |
| 6,743,230 B2 | 6/2004 | Lutze et al. |
| 6,746,447 B2 | 6/2004 | Davison et al. |
| 6,755,825 B2 | 6/2004 | Shoenman et al. |
| 6,755,827 B2 | 6/2004 | Mulier et al. |
| 6,757,565 B2 | 6/2004 | Sharkey et al. |
| 6,758,846 B2 | 7/2004 | Goble et al. |
| 6,761,718 B2 | 7/2004 | Madsen |
| 6,764,487 B2 | 7/2004 | Mulier et al. |
| 6,766,202 B2 | 7/2004 | Underwood et al. |
| 6,766,817 B2 | 7/2004 | da Silva |
| 6,770,070 B1 | 8/2004 | Balbierz |
| 6,770,071 B2 | 8/2004 | Woloszko et al. |
| 6,770,072 B1 | 8/2004 | Truckai et al. |
| 6,772,012 B2 | 8/2004 | Ricart et al. |
| 6,772,013 B1 | 8/2004 | Ingle et al. |
| 6,775,575 B2 | 8/2004 | Bommannan et al. |
| 6,776,780 B2 | 8/2004 | Mulier et al. |
| 6,780,177 B2 | 8/2004 | Shafirstein et al. |
| 6,780,180 B1 | 8/2004 | Goble et al. |
| 6,786,906 B1 | 9/2004 | Cobb |
| 6,796,981 B2 | 9/2004 | Wham et al. |
| 6,800,077 B1 | 10/2004 | Mucko et al. |
| 6,802,842 B2 | 10/2004 | Ellman et al. |
| 6,802,843 B2 | 10/2004 | Truckai et al. |
| 6,808,525 B2 | 10/2004 | Latterell et al. |
| 6,813,520 B2 | 11/2004 | Truckai et al. |
| 6,814,714 B1 | 11/2004 | Novak et al. |
| 6,814,731 B2 | 11/2004 | Swanson |
| 6,821,273 B2 | 11/2004 | Mollenauer |
| 6,827,713 B2 | 12/2004 | Bek et al. |
| 6,827,725 B2 | 12/2004 | Batchelor et al. |
| 6,832,996 B2 | 12/2004 | Woloszko |
| 6,832,997 B2 | 12/2004 | Uchida et al. |
| 6,835,195 B2 | 12/2004 | Schulze et al. |
| 6,836,688 B2 | 12/2004 | Ingle et al. |
| 6,843,789 B2 | 1/2005 | Goble |
| 6,845,264 B1 | 1/2005 | Skladnev et al. |
| 6,849,073 B2 | 2/2005 | Hoey et al. |
| 6,855,145 B2 | 2/2005 | Ciarrocca |
| 6,858,028 B2 | 2/2005 | Mulier et al. |
| 6,860,882 B2 | 3/2005 | Battles et al. |
| 6,863,669 B2 | 3/2005 | Spitzer |
| 6,864,686 B2 | 3/2005 | Novak et al. |
| 6,881,214 B2 | 4/2005 | Cosman et al. |
| 6,882,885 B2 | 4/2005 | Levy, Jr. et al. |
| 6,887,237 B2 | 5/2005 | McGaffigan |
| 6,887,240 B1 | 5/2005 | Lands et al. |
| 6,893,435 B2 | 5/2005 | Goble |
| 6,893,440 B2 | 5/2005 | Durgin et al. |
| 6,896,672 B1 | 5/2005 | Eggers et al. |
| 6,896,674 B1 | 5/2005 | Woloszko et al. |
| 6,899,712 B2 | 5/2005 | Moutafis et al. |
| 6,905,497 B2 | 6/2005 | Truckai et al. |
| 6,905,499 B1 | 6/2005 | Mucko et al. |
| 6,911,019 B2 | 6/2005 | Mulier et al. |
| 6,915,806 B2 | 7/2005 | Pacek et al. |
| 6,918,404 B2 | 7/2005 | Dias da Silva |
| 6,921,398 B2 | 7/2005 | Carmel et al. |
| 6,921,399 B2 | 7/2005 | Carmel et al. |
| 6,923,803 B2 | 8/2005 | Goble |
| 6,923,805 B1 | 8/2005 | LaFontaine et al. |
| 6,926,706 B1 | 8/2005 | Sealfon |
| 6,926,716 B2 | 8/2005 | Baker et al. |
| 6,926,717 B1 | 8/2005 | Garito et al. |
| 6,929,640 B1 | 8/2005 | Underwood et al. |
| 6,929,641 B2 | 8/2005 | Goble et al. |
| 6,929,642 B2 | 8/2005 | Xiao et al. |
| 6,929,644 B2 | 8/2005 | Truckai et al. |
| 6,929,645 B2 | 8/2005 | Battles et al. |
| 6,932,810 B2 | 8/2005 | Ryan |
| 6,932,815 B2 | 8/2005 | Sutter |
| 6,942,661 B2 | 9/2005 | Swanson |
| 6,949,096 B2 | 9/2005 | Davison et al. |
| 6,949,098 B2 | 9/2005 | Mulier et al. |
| 6,951,559 B1 | 10/2005 | Greep |
| 6,953,461 B2 | 10/2005 | McClurken et al. |
| 6,960,204 B2 | 11/2005 | Eggers et al. |
| 6,960,207 B2 | 11/2005 | Vanney et al. |
| 6,960,210 B2 | 11/2005 | Lands et al. |
| 6,962,589 B2 | 11/2005 | Mulier et al. |
| 6,964,274 B1 | 11/2005 | Ryan et al. |
| 6,964,661 B2 | 11/2005 | Rioux et al. |
| 6,966,907 B2 | 11/2005 | Goble |
| 6,966,909 B2 | 11/2005 | Marshall et al. |
| 6,971,394 B2 | 12/2005 | Sliwa, Jr. et al. |
| 6,974,452 B1 | 12/2005 | Gille et al. |
| 6,974,453 B2 | 12/2005 | Woloszko et al. |
| 6,979,332 B2 | 12/2005 | Adams |
| 6,984,231 B2 | 1/2006 | Goble et al. |
| 6,986,769 B2 | 1/2006 | Nelson et al. |
| 6,991,631 B2 | 1/2006 | Woloszko et al. |
| 7,001,380 B2 | 2/2006 | Goble |
| 7,001,382 B2 | 2/2006 | Gallo, Sr. |
| 7,004,941 B2 | 2/2006 | Tvinnereim et al. |
| 7,004,942 B2 | 2/2006 | Laird et al. |
| 7,008,419 B2 | 3/2006 | Shadduck |
| 7,008,421 B2 | 3/2006 | Daniel et al. |
| 7,033,348 B2 | 4/2006 | Alfano et al. |
| 7,033,356 B2 | 4/2006 | Latterell et al. |
| 7,041,096 B2 | 5/2006 | Malis et al. |
| 7,041,101 B2 | 5/2006 | Eggers |
| 7,041,102 B2 | 5/2006 | Truckai et al. |
| 7,052,494 B2 | 5/2006 | Goble et al. |
| 7,060,064 B2 | 6/2006 | Allen et al. |
| 7,063,670 B2 | 6/2006 | Sampson et al. |
| 7,066,586 B2 | 6/2006 | da Silva |
| 7,066,932 B1 | 6/2006 | Morgan et al. |
| 7,066,936 B2 | 6/2006 | Ryan |
| 7,070,596 B1 | 7/2006 | Woloszko et al. |
| 7,070,604 B1 | 7/2006 | Garito et al. |
| 7,074,217 B2 | 7/2006 | Strul et al. |
| 7,074,219 B2 | 7/2006 | Levine et al. |
| 7,083,601 B1 | 8/2006 | Cosmescu |
| 7,087,051 B2 | 8/2006 | Bourne et al. |
| 7,087,053 B2 | 8/2006 | Vanney |
| 7,094,215 B2 | 8/2006 | Davison et al. |
| 7,101,387 B2 | 9/2006 | Garabedian et al. |
| 7,104,986 B2 | 9/2006 | Hovda et al. |
| 7,112,199 B2 | 9/2006 | Cosmescu |
| 7,115,139 B2 | 10/2006 | McClurken et al. |
| 7,125,406 B2 | 10/2006 | Given |
| 7,147,634 B2 | 12/2006 | Nesbitt |
| 7,147,635 B2 | 12/2006 | Ciarrocca |
| 7,147,637 B2 | 12/2006 | Goble |
| 7,147,638 B2 | 12/2006 | Chapman et al. |
| 7,150,746 B2 | 12/2006 | DeCesare et al. |
| 7,150,747 B1 | 12/2006 | McDonald et al. |
| 7,150,748 B2 | 12/2006 | Ebbutt et al. |
| 7,153,300 B2 | 12/2006 | Goble |
| 7,156,845 B2 | 1/2007 | Mulier et al. |
| 7,166,105 B2 | 1/2007 | Mulier et al. |
| 7,166,106 B2 | 1/2007 | Bartel et al. |
| 7,169,143 B2 | 1/2007 | Eggers et al. |
| 7,169,144 B2 | 1/2007 | Hoey et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,811,282 B2 | 10/2010 | McClurken |
| 2001/0014819 A1 | 8/2001 | Ingle et al. |
| 2001/0020167 A1 | 9/2001 | Woloszko et al. |
| 2001/0023365 A1 | 9/2001 | Medhkour et al. |
| 2001/0025178 A1 | 9/2001 | Mulier et al. |
| 2001/0029370 A1 | 10/2001 | Hodva et al. |
| 2001/0032002 A1 | 10/2001 | McClurken et al. |
| 2001/0037106 A1 | 11/2001 | Shadduck |
| 2001/0039419 A1 | 11/2001 | Francischelli et al. |
| 2001/0041921 A1 | 11/2001 | Mulier et al. |
| 2001/0051802 A1 | 12/2001 | Woloszko et al. |
| 2001/0051804 A1 | 12/2001 | Mulier et al. |

| | | | | | |
|---|---|---|---|---|---|
| 2002/0002393 A1 | 1/2002 | Mitchell | 2004/0073205 A1 | 4/2004 | Treat et al. |
| 2002/0010463 A1 | 1/2002 | Mulier et al. | 2004/0073208 A1 | 4/2004 | Sutter |
| 2002/0013582 A1 | 1/2002 | Mulier et al. | 2004/0078034 A1 | 4/2004 | Acker et al. |
| 2002/0016589 A1 | 2/2002 | Swartz et al. | 2004/0078037 A1 | 4/2004 | Batchelor et al. |
| 2002/0019628 A1 | 2/2002 | Comben | 2004/0078038 A1 | 4/2004 | Desinger et al. |
| 2002/0022870 A1 | 2/2002 | Truckai et al. | 2004/0082946 A1 | 4/2004 | Malis et al. |
| 2002/0026186 A1 | 2/2002 | Woloszko et al. | 2004/0082952 A1 | 4/2004 | Dycus et al. |
| 2002/0026187 A1 | 2/2002 | Swanson | 2004/0087937 A1 | 5/2004 | Eggers et al. |
| 2002/0029036 A1 | 3/2002 | Goble et al. | 2004/0087939 A1 | 5/2004 | Eggers et al. |
| 2002/0035361 A1 | 3/2002 | Houser et al. | 2004/0087940 A1 | 5/2004 | Jahns et al. |
| 2002/0035387 A1 | 3/2002 | Mulier et al. | 2004/0087943 A1 | 5/2004 | Dycus et al. |
| 2002/0049438 A1 | 4/2002 | Sharkey et al. | 2004/0088029 A1 | 5/2004 | Yamamoto |
| 2002/0049439 A1 | 4/2002 | Mulier et al. | 2004/0092925 A1 | 5/2004 | Rizoiu et al. |
| 2002/0049483 A1 | 4/2002 | Knowlton | 2004/0092926 A1 | 5/2004 | Hoey et al. |
| 2002/0058933 A1 | 5/2002 | Christopherson et al. | 2004/0097919 A1 | 5/2004 | Wellman et al. |
| 2002/0058935 A1 | 5/2002 | Hoey et al. | 2004/0102770 A1 | 5/2004 | Goble |
| 2002/0062123 A1 | 5/2002 | McClurken et al. | 2004/0102824 A1 | 5/2004 | Sharkey et al. |
| 2002/0095150 A1 | 7/2002 | Goble | 2004/0111136 A1 | 6/2004 | Sharkey et al. |
| 2002/0095151 A1 | 7/2002 | Dahla et al. | 2004/0111137 A1 | 6/2004 | Sharkey et al. |
| 2002/0095152 A1 | 7/2002 | Ciarrocca et al. | 2004/0116923 A1 | 6/2004 | Desinger |
| 2002/0099366 A1 | 7/2002 | Dahla et al. | 2004/0122420 A1 | 6/2004 | Amoah |
| 2002/0115991 A1 | 8/2002 | Edwards | 2004/0122423 A1 | 6/2004 | Dycus et al. |
| 2002/0115992 A1 | 8/2002 | Utley et al. | 2004/0122494 A1 | 6/2004 | Eggers et al. |
| 2002/0120259 A1 | 8/2002 | Lettice et al. | 2004/0138654 A1 | 7/2004 | Goble |
| 2002/0120260 A1 | 8/2002 | Morris et al. | 2004/0138655 A1 | 7/2004 | McClurken et al. |
| 2002/0120261 A1 | 8/2002 | Morris et al. | 2004/0138657 A1 | 7/2004 | Bourne et al. |
| 2002/0128650 A1 | 9/2002 | McClurken | 2004/0143257 A1 | 7/2004 | Fuimaono |
| 2002/0133148 A1 | 9/2002 | Daniel et al. | 2004/0143258 A1 | 7/2004 | Fuimaono |
| 2002/0151884 A1 | 10/2002 | Hoey et al. | 2004/0143259 A1 | 7/2004 | Mulier et al. |
| 2002/0156511 A1 | 10/2002 | Habib | 2004/0143263 A1 | 7/2004 | Schechter et al. |
| 2002/0161364 A1 | 10/2002 | Mulier et al. | 2004/0147902 A1 | 7/2004 | McGuckin, Jr. et al. |
| 2002/0169446 A1 | 11/2002 | Mulier et al. | 2004/0147916 A1 | 7/2004 | Baker |
| 2002/0177846 A1 | 11/2002 | Mulier et al. | 2004/0147922 A1 | 7/2004 | Keppel |
| 2002/0183733 A1 | 12/2002 | Mulier et al. | 2004/0147925 A1 | 7/2004 | Buysse et al. |
| 2002/0188284 A1 | 12/2002 | To et al. | 2004/0162552 A1 | 8/2004 | McClurken |
| 2002/0193851 A1 | 12/2002 | Silverman et al. | 2004/0162554 A1 | 8/2004 | Lee et al. |
| 2002/0198524 A1 | 12/2002 | Mulier et al. | 2004/0162557 A1 | 8/2004 | Tetzlaff et al. |
| 2003/0004510 A1 | 1/2003 | Wham et al. | 2004/0162572 A1 | 8/2004 | Sauer |
| 2003/0014050 A1 | 1/2003 | Sharkey et al. | 2004/0167508 A1 | 8/2004 | Wham et al. |
| 2003/0032954 A1 | 2/2003 | Carranza et al. | 2004/0172111 A1 | 9/2004 | Hijii et al. |
| 2003/0032955 A1 | 2/2003 | Mulier et al. | 2004/0176760 A1 | 9/2004 | Qiu |
| 2003/0073989 A1 | 4/2003 | Hoey et al. | 2004/0176761 A1 | 9/2004 | Desinger |
| 2003/0073993 A1 | 4/2003 | Ciarrocca | 2004/0176762 A1 | 9/2004 | Lawes et al. |
| 2003/0114850 A1 | 6/2003 | McClurken et al. | 2004/0181219 A1 | 9/2004 | Goble et al. |
| 2003/0181902 A1 | 9/2003 | Mulier et al. | 2004/0181250 A1 | 9/2004 | Adams et al. |
| 2003/0204185 A1 | 10/2003 | Sherman et al. | 2004/0186469 A1 | 9/2004 | Woloszko et al. |
| 2003/0216733 A1 | 11/2003 | McClurken et al. | 2004/0186470 A1 | 9/2004 | Goble et al. |
| 2004/0015162 A1 | 1/2004 | McGaffigan | 2004/0186535 A1 | 9/2004 | Knowlton |
| 2004/0015163 A1 | 1/2004 | Buysse et al. | 2004/0193148 A1 | 9/2004 | Wham et al. |
| 2004/0015215 A1 | 1/2004 | Fredricks et al. | 2004/0193150 A1 | 9/2004 | Sharkey et al. |
| 2004/0015216 A1 | 1/2004 | DeSisto | 2004/0193152 A1 | 9/2004 | Sutton et al. |
| 2004/0015218 A1 | 1/2004 | Finch et al. | 2004/0193211 A1 | 9/2004 | Voegele et al. |
| 2004/0019350 A1 | 1/2004 | O'Brien et al. | 2004/0199156 A1 | 10/2004 | Rioux et al. |
| 2004/0024395 A1 | 2/2004 | Ellman et al. | 2004/0199160 A1 | 10/2004 | Slater |
| 2004/0024396 A1 | 2/2004 | Eggers | 2004/0206365 A1 | 10/2004 | Knowlton |
| 2004/0024398 A1 | 2/2004 | Hovda et al. | 2004/0210213 A1 | 10/2004 | Fuimaono et al. |
| 2004/0024399 A1 | 2/2004 | Sharps et al. | 2004/0210214 A1 | 10/2004 | Knowlton |
| 2004/0030327 A1 | 2/2004 | Golan | 2004/0215181 A1 | 10/2004 | Christopherson et al. |
| 2004/0030328 A1 | 2/2004 | Eggers et al. | 2004/0215182 A1 | 10/2004 | Lee |
| 2004/0030330 A1 | 2/2004 | Brassell et al. | 2004/0215183 A1 | 10/2004 | Hoey et al. |
| 2004/0030332 A1 | 2/2004 | Knowlton et al. | 2004/0215184 A1 | 10/2004 | Eggers et al. |
| 2004/0030333 A1 | 2/2004 | Goble | 2004/0215185 A1 | 10/2004 | Truckai et al. |
| 2004/0034340 A1 | 2/2004 | Biscup | 2004/0215188 A1 | 10/2004 | Mulier et al. |
| 2004/0034346 A1 | 2/2004 | Stern et al. | 2004/0215235 A1 | 10/2004 | Jackson et al. |
| 2004/0034349 A1 | 2/2004 | Kirwan, Jr. et al. | 2004/0215296 A1 | 10/2004 | Ganz et al. |
| 2004/0034400 A1 | 2/2004 | Ingle et al. | 2004/0220561 A1 | 11/2004 | Kirwan, Jr. et al. |
| 2004/0039429 A1 | 2/2004 | Daniel et al. | 2004/0220562 A1 | 11/2004 | Garabedian et al. |
| 2004/0044341 A1 | 3/2004 | Truckai et al. | 2004/0225288 A1 | 11/2004 | Buysse et al. |
| 2004/0054363 A1 | 3/2004 | Vaska et al. | 2004/0230190 A1 | 11/2004 | Dahla et al. |
| 2004/0054365 A1 | 3/2004 | Goble | 2004/0236322 A1 | 11/2004 | Mulier et al. |
| 2004/0054366 A1 | 3/2004 | Davison et al. | 2004/0236324 A1 | 11/2004 | Muller et al. |
| 2004/0054369 A1 | 3/2004 | Nelson et al. | 2004/0243125 A1 | 12/2004 | Dycus et al. |
| 2004/0054370 A1 | 3/2004 | Given | 2004/0243163 A1 | 12/2004 | Casiano et al. |
| 2004/0059328 A1 | 3/2004 | Daniel et al. | 2004/0249371 A1 | 12/2004 | Dycus et al. |
| 2004/0059363 A1 | 3/2004 | Alvarez et al. | 2004/0249374 A1 | 12/2004 | Tetzlaff et al. |
| 2004/0064023 A1 | 4/2004 | Ryan et al. | 2004/0249425 A1 | 12/2004 | Roy et al. |
| 2004/0064137 A1 | 4/2004 | Pellegrino et al. | 2004/0260279 A1 | 12/2004 | Goble et al. |
| 2004/0068306 A1 | 4/2004 | Shadduck | 2004/0260280 A1 | 12/2004 | Sartor |
| 2004/0068307 A1 | 4/2004 | Goble | 2004/0260368 A1 | 12/2004 | Ingle et al. |

| Publication No. | Date | Inventor |
|---|---|---|
| 2005/0010205 A1 | 1/2005 | Hovda et al. |
| 2005/0010212 A1 | 1/2005 | McClurken et al. |
| 2005/0015085 A1 | 1/2005 | McClurken et al. |
| 2005/0015086 A1 | 1/2005 | Platt |
| 2005/0015130 A1 | 1/2005 | Gill |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0033292 A1 | 2/2005 | Teitelbaum et al. |
| 2005/0038471 A1 | 2/2005 | Chan et al. |
| 2005/0043728 A1 | 2/2005 | Ciarrocca |
| 2005/0049583 A1 | 3/2005 | Swanson |
| 2005/0049586 A1 | 3/2005 | Daniel et al. |
| 2005/0055019 A1 | 3/2005 | Skarda |
| 2005/0055020 A1 | 3/2005 | Skarda |
| 2005/0059966 A1 | 3/2005 | McClurken et al. |
| 2005/0070888 A1 | 3/2005 | Dimatteo et al. |
| 2005/0070891 A1 | 3/2005 | DeSisto |
| 2005/0070894 A1 | 3/2005 | McClurken |
| 2005/0070896 A1 | 3/2005 | Daniel et al. |
| 2005/0080410 A1 | 4/2005 | Rioux et al. |
| 2005/0080413 A1 | 4/2005 | Canady |
| 2005/0085804 A1 | 4/2005 | McGaffigan |
| 2005/0085809 A1 | 4/2005 | Mucko et al. |
| 2005/0085880 A1 | 4/2005 | Truckai et al. |
| 2005/0090816 A1 | 4/2005 | McClurken et al. |
| 2005/0090819 A1 | 4/2005 | Goble |
| 2005/0096649 A1 | 5/2005 | Adams |
| 2005/0096651 A1 | 5/2005 | Truckai et al. |
| 2005/0101951 A1 | 5/2005 | Wham et al. |
| 2005/0101952 A1 | 5/2005 | Lands et al. |
| 2005/0101965 A1 | 5/2005 | Ryan |
| 2005/0107778 A1 | 5/2005 | Rioux et al. |
| 2005/0107779 A1 | 5/2005 | Ellman et al. |
| 2005/0107784 A1 | 5/2005 | Moses et al. |
| 2005/0107786 A1 | 5/2005 | Canady |
| 2005/0113820 A1 | 5/2005 | Goble et al. |
| 2005/0113825 A1 | 5/2005 | Cosmescu |
| 2005/0124987 A1 | 6/2005 | Goble |
| 2005/0130929 A1 | 6/2005 | Boyd |
| 2005/0131402 A1 | 6/2005 | Ciarrocca et al. |
| 2005/0137590 A1 | 6/2005 | Lawes et al. |
| 2005/0137662 A1 | 6/2005 | Morris et al. |
| 2005/0143729 A1 | 6/2005 | Francischelli et al. |
| 2005/0154385 A1 | 7/2005 | Heim et al. |
| 2005/0154433 A1 | 7/2005 | Levy, Jr. et al. |
| 2005/0159739 A1 | 7/2005 | Paul et al. |
| 2005/0159740 A1 | 7/2005 | Paul et al. |
| 2005/0159778 A1 | 7/2005 | Heinrich et al. |
| 2005/0159797 A1 | 7/2005 | Chandran et al. |
| 2005/0165444 A1 | 7/2005 | Hart et al. |
| 2005/0171524 A1 | 8/2005 | Stern et al. |
| 2005/0171526 A1 | 8/2005 | Rioux et al. |
| 2005/0171532 A1 | 8/2005 | Ciarrocca |
| 2005/0171533 A1 | 8/2005 | Latterell et al. |
| 2005/0171534 A1 | 8/2005 | Habib |
| 2005/0171583 A1 | 8/2005 | Mosher et al. |
| 2005/0177150 A1 | 8/2005 | Amoah et al. |
| 2005/0177209 A1 | 8/2005 | Leung et al. |
| 2005/0187543 A1 | 8/2005 | Underwood et al. |
| 2005/0187599 A1 | 8/2005 | Sharkey et al. |
| 2005/0203503 A1 | 9/2005 | Edwards et al. |
| 2005/0203504 A1 | 9/2005 | Wham et al. |
| 2005/0209591 A1 | 9/2005 | Sutter |
| 2005/0209621 A1 | 9/2005 | Gordon et al. |
| 2005/0222602 A1 | 10/2005 | Sutter et al. |
| 2005/0222611 A1 | 10/2005 | Weitkamp |
| 2005/0228372 A1 | 10/2005 | Truckai et al. |
| 2005/0245918 A1 | 11/2005 | Sliwa, Jr. et al. |
| 2005/0245921 A1 | 11/2005 | Strul et al. |
| 2005/0245922 A1 | 11/2005 | Goble |
| 2005/0245923 A1 | 11/2005 | Christopherson et al. |
| 2005/0250477 A1 | 11/2005 | Eastwood et al. |
| 2005/0251128 A1 | 11/2005 | Amoah |
| 2005/0251134 A1 | 11/2005 | Woloszko et al. |
| 2005/0256519 A1 | 11/2005 | Goble et al. |
| 2005/0261676 A1 | 11/2005 | Hall et al. |
| 2005/0261677 A1 | 11/2005 | Hall et al. |
| 2005/0267465 A1 | 12/2005 | Hillier et al. |
| 2005/0267467 A1 | 12/2005 | Paul et al. |
| 2005/0267468 A1 | 12/2005 | Truckai et al. |
| 2005/0267469 A1 | 12/2005 | Blocher |
| 2005/0273092 A1 | 12/2005 | G. et al. |
| 2005/0273097 A1 | 12/2005 | Ryan |
| 2005/0277915 A1 | 12/2005 | DeCesare et al. |
| 2005/0277916 A1 | 12/2005 | DeCesare et al. |
| 2005/0277917 A1 | 12/2005 | Garito et al. |
| 2005/0283147 A1 | 12/2005 | Yachi |
| 2005/0283148 A1 | 12/2005 | Janssen et al. |
| 2005/0283149 A1 | 12/2005 | Thorne et al. |
| 2005/0283150 A1 | 12/2005 | Moutafis et al. |
| 2005/0283151 A1 | 12/2005 | Ebbutt et al. |
| 2005/0288661 A1 | 12/2005 | Sauvageau et al. |
| 2005/0288665 A1 | 12/2005 | Woloszko |
| 2006/0004356 A1 | 1/2006 | Bilski et al. |
| 2006/0009760 A1 | 1/2006 | Mulier et al. |
| 2006/0009762 A1 | 1/2006 | Whayne |
| 2006/0015097 A1 | 1/2006 | Mulier et al. |
| 2006/0020265 A1 | 1/2006 | Ryan |
| 2006/0025765 A1 | 2/2006 | Landman et al. |
| 2006/0025766 A1 | 2/2006 | Heinrich et al. |
| 2006/0030912 A1 | 2/2006 | Eggers et al. |
| 2006/0036235 A1 | 2/2006 | Swoyer et al. |
| 2006/0036237 A1 | 2/2006 | Davison et al. |
| 2006/0036239 A1 | 2/2006 | Canady |
| 2006/0041254 A1 | 2/2006 | Francischelli et al. |
| 2006/0041255 A1 | 2/2006 | Eggers et al. |
| 2006/0047275 A1 | 3/2006 | Goble |
| 2006/0047280 A1 | 3/2006 | Goble et al. |
| 2006/0047331 A1 | 3/2006 | Lax et al. |
| 2006/0052770 A1 | 3/2006 | Mulier et al. |
| 2006/0064085 A1 | 3/2006 | Schechter et al. |
| 2006/0064101 A1 | 3/2006 | Arramon |
| 2006/0074411 A1 | 4/2006 | Carmel et al. |
| 2006/0074414 A1 | 4/2006 | Mulier et al. |
| 2006/0079872 A1 | 4/2006 | Eggleston |
| 2006/0079888 A1 | 4/2006 | Mulier et al. |
| 2006/0084968 A1 | 4/2006 | Truckai et al. |
| 2006/0095026 A1 | 5/2006 | Ricart et al. |
| 2006/0095031 A1 | 5/2006 | Ormsby |
| 2006/0095034 A1 | 5/2006 | Garito et al. |
| 2006/0095075 A1 | 5/2006 | Burkinshaw et al. |
| 2006/0095103 A1 | 5/2006 | Eggers et al. |
| 2006/0100619 A1 | 5/2006 | McClurken et al. |
| 2006/0106376 A1 | 5/2006 | Godara et al. |
| 2006/0106379 A1 | 5/2006 | O'Brien et al. |
| 2006/0111705 A1 | 5/2006 | Janzen et al. |
| 2006/0111709 A1 | 5/2006 | Goble et al. |
| 2006/0111710 A1 | 5/2006 | Goble et al. |
| 2006/0111711 A1 | 5/2006 | Goble |
| 2006/0111741 A1 | 5/2006 | Nardella |
| 2006/0116675 A1 | 6/2006 | McClurken et al. |
| 2006/0122593 A1 | 6/2006 | Jun et al. |
| 2006/0129145 A1 | 6/2006 | Woloszko et al. |
| 2006/0129185 A1 | 6/2006 | Paternuosto |
| 2006/0142757 A1 | 6/2006 | Daniel et al. |
| 2006/0149225 A1 | 7/2006 | McClurken |
| 2006/0167446 A1 | 7/2006 | Pozzato |
| 2006/0167449 A1 | 7/2006 | Mulier et al. |
| 2006/0167451 A1 | 7/2006 | Cropper |
| 2006/0178667 A1 | 8/2006 | Sartor et al. |
| 2006/0178668 A1 | 8/2006 | Albritton, IV |
| 2006/0178670 A1 | 8/2006 | Woloszko et al. |
| 2006/0178699 A1 | 8/2006 | Surti |
| 2006/0184164 A1 | 8/2006 | Malis et al. |
| 2006/0184167 A1 | 8/2006 | Vaska et al. |
| 2006/0189977 A1 | 8/2006 | Allen et al. |
| 2006/0189979 A1 | 8/2006 | Esch et al. |
| 2006/0195079 A1 | 8/2006 | Eberl |
| 2006/0200123 A1 | 9/2006 | Ryan |
| 2006/0217700 A1 | 9/2006 | Garito et al. |
| 2006/0217701 A1 | 9/2006 | Young et al. |
| 2006/0217707 A1 | 9/2006 | Daniel et al. |
| 2006/0224154 A1 | 10/2006 | Shadduck et al. |
| 2006/0235286 A1 | 10/2006 | Stone et al. |
| 2006/0235377 A1 | 10/2006 | Earley et al. |
| 2006/0235379 A1 | 10/2006 | McClurken et al. |

| | | | |
|---|---|---|---|
| 2006/0241577 A1 | 10/2006 | Balbierz et al. | |
| 2006/0241587 A1 | 10/2006 | Heim et al. | |
| 2006/0241588 A1 | 10/2006 | Heim et al. | |
| 2006/0241589 A1 | 10/2006 | Heim et al. | |
| 2006/0247614 A1 | 11/2006 | Sampson et al. | |
| 2006/0259025 A1 | 11/2006 | Dahla | |
| 2006/0259031 A1 | 11/2006 | Carmel et al. | |
| 2006/0259070 A1 | 11/2006 | Livneh | |
| 2006/0264927 A1 | 11/2006 | Ryan | |
| 2006/0264929 A1 | 11/2006 | Goble et al. | |
| 2006/0264931 A1 | 11/2006 | Chapman et al. | |
| 2006/0271033 A1 | 11/2006 | Ein-Gal | |
| 2006/0271036 A1 | 11/2006 | Garabedian et al. | |
| 2006/0271042 A1 | 11/2006 | Latterell et al. | |
| 2006/0276783 A1 | 12/2006 | Cosmescu | |
| 2006/0276785 A1 | 12/2006 | Asahara et al. | |
| 2007/0000501 A1 | 1/2007 | Wert et al. | |
| 2007/0010812 A1 | 1/2007 | Mittelstein et al. | |
| 2007/0016182 A1 | 1/2007 | Lipson et al. | |
| 2007/0049920 A1 | 3/2007 | McClurken et al. | |
| 2007/0093808 A1 | 4/2007 | Mulier et al. | |
| 2007/0118114 A1 | 5/2007 | Miller et al. | |
| 2007/0208332 A1 | 9/2007 | Mulier et al. | |
| 2008/0015563 A1 | 1/2008 | Hoey et al. | |
| 2008/0071270 A1 | 3/2008 | Desinger et al. | |

FOREIGN PATENT DOCUMENTS

| | | |
|---|---|---|
| EP | 0 175 595 | 3/1986 |
| EP | 0 895 756 A1 | 2/1999 |
| EP | 0 956 826 A2 | 11/1999 |
| EP | 0 833 593 B1 | 2/2001 |
| EP | 1 080 682 A1 | 3/2001 |
| EP | 1 095 627 A1 | 5/2001 |
| EP | 0 760 626 B1 | 9/2001 |
| EP | 0 837 647 B1 | 10/2001 |
| EP | 1 149 563 A1 | 10/2001 |
| EP | 1 157 666 A1 | 11/2001 |
| EP | 1 181 896 A1 | 2/2002 |
| EP | 1 383 438 B1 | 2/2006 |
| FR | 2 235 669 | 1/1975 |
| JP | 57-117843 | 7/1982 |
| JP | 5-092009 | 4/1993 |
| JP | 7-124245 | 5/1995 |
| JP | 2002-65692 A | 3/2002 |
| WO | WO 90/03152 A1 | 4/1990 |
| WO | WO 94/02077 A2 | 2/1994 |
| WO | WO 94/26228 A1 | 11/1994 |
| WO | WO 95/05781 A1 | 3/1995 |
| WO | WO 95/09570 A1 | 4/1995 |
| WO | WO 95/17222 A1 | 6/1995 |
| WO | WO 95/30373 A1 | 11/1995 |
| WO | WO 96/34571 A1 | 11/1996 |
| WO | WO 96/39914 A1 | 12/1996 |
| WO | WO 97/00646 A1 | 1/1997 |
| WO | WO 97/05829 A1 | 2/1997 |
| WO | WO 97/16127 A1 | 5/1997 |
| WO | WO 98/14131 A1 | 4/1998 |
| WO | WO 98/38932 A1 | 9/1998 |
| WO | WO 99/03414 A1 | 1/1999 |
| WO | WO 99/09919 A1 | 3/1999 |
| WO | WO 99/20213 A1 | 4/1999 |
| WO | WO 99/42044 A1 | 8/1999 |
| WO | WO 99/58070 A2 | 11/1999 |
| WO | WO 99/66850 A1 | 12/1999 |
| WO | WO 00/32127 A1 | 6/2000 |
| WO | WO 00/36985 A2 | 6/2000 |
| WO | WO 00/78240 A1 | 12/2000 |
| WO | WO 01/00099 A1 | 1/2001 |
| WO | WO 01/24720 A1 | 4/2001 |
| WO | WO 01/26570 A1 | 4/2001 |
| WO | WO 01/28444 A1 | 4/2001 |
| WO | WO 01/35845 A1 | 5/2001 |
| WO | WO 01/60273 A1 | 8/2001 |
| WO | WO 01/66026 A2 | 9/2001 |
| WO | WO 01/66027 A1 | 9/2001 |
| WO | WO 01/70114 A1 | 9/2001 |
| WO | WO 01/80757 A2 | 11/2001 |
| WO | WO 01/82812 A1 | 11/2001 |
| WO | WO 01/89403 A1 | 11/2001 |
| WO | WO 02/11635 A1 | 2/2002 |
| WO | WO 02/17804 A2 | 3/2002 |
| WO | WO 02/24089 A1 | 3/2002 |
| WO | WO 02/069821 A1 | 9/2002 |
| WO | WO 02/071966 A1 | 9/2002 |
| WO | WO 02/085230 A2 | 10/2002 |
| WO | WO 03/020339 A2 | 3/2003 |
| WO | WO 03/024349 A1 | 3/2003 |
| WO | WO 03/049631 A1 | 6/2003 |
| WO | WO 03/082134 A1 | 10/2003 |
| WO | WO 03/096880 A2 | 11/2003 |
| WO | WO 2004/039416 | 5/2004 |
| WO | WO 2005/122938 A1 | 12/2005 |
| WO | WO 2006/062916 A2 | 6/2006 |
| WO | WO 2006/062939 A2 | 6/2006 |

OTHER PUBLICATIONS

TissueLink Floating Ball™ brochure, 71-100001-001 Rev A, Copyright 2001, 4 pages.

TissueLink DS™ dissecting sealer, Instructions for Use, 70-10-0004 Rev A, Effective Date: Feb. 2002, 8 pages.

TissueLink DS3.0™ dissecting sealer brochure, 71-10-0391 Rev A, Copyright 2002, 2 pages.

TissueLink Endo SH™ sealing hook, Instructions for Use, 70-10-0304 Rev A, Effective Date: Feb. 2002, 8 pages.

TissueLink Endo SH2.0 Endoscopic Sealing Hook brochure, 71-10-0607 Rev A, Copyright 2006, 2 pages.

Hemostatic Effectiveness of the TissueLink Floating Ball™, Pre-Clinical Study #200, 74-820002-200-A, 2 pages, Copyright 2001.

Histologic Characteristics of the TissueLink Floating Ball™ Device Coagulation on Porcine Liver, Pre-Clinical Study #204, 74-820002-204-A, 4 pages, Copyright 2002.

Laparoscopic Cholecystectomy Use of the TissueLink Floating Ball™ Device in Difficult Cases, Clinical Experience #103, 74-820002-103-A, 2 pages, Copyright 2002.

Sealing of Intrahepatic Bile Ducts Using the TissueLink Floating Ball™ in an Acute Porcine Model, Pre-Clinical Study #201, 74-820002-201-A, 4 pages, Copyright 2001.

Thermal Effect of TissueLink™ Technology on Liver, Technical Brief #301, 74-82-0423 Rev A, 4 pages, Copyright 2002.

TissueLink FB3.0 Floating Ball™ in Orthopaedic Surgery Radiofrequency Coupled With Conductive Fluid for Hemostasis in Soft Tissue: A Chronic Animal Study, Pre-Clinical Study #205, 74-82-0408 Rev A, 4 pages, Copyright 2002.

TissueLink FB3.0 Floating Ball™ in Orthopaedic Surgery Range of Motion Study, Pre-Clinical Study #206, 74-82-0409 Rev A, 4 pages, Copyright 2002.

TissueLink Floating Ball™ Assisted Colorectal Hepatic Metastasectomy, Clinical Experience #101, 74-820002-101-A, 4 pages, Copyright 2001.

TissueLink Floating Ball™ Utility on Liver Resection, Clinical Experience #102, 74-820002-102-A, 1 page, Copyright 2001.

Use of the TissueLink Floating Ball™ Device Thoracic Summary, Clinical Experience #104, 74-820002-104-A, 4 pages, Copyright 2002.

Use of the TissueLink Floating Ball™ During Hepatic Resection, Clinical Experience #100, 74-820002-100-A, 2 pages, Copyright 2001.

VATS Pulmonary Nodulectomy Using the TissueLink Floating Ball™ Device, Clinical Experience #105, 74-820002-105-A, 2 pages, Copyright 2002.

United States Office Action dated Aug. 4, 2009 issued in related U.S. Appl. No. 11/537,852.

Office Action dated Apr. 14, 2009 issued in related U.S. Appl. No. 10/547,881.

Office Action dated Sep. 8, 2009 issued in related U.S. Appl. No. 10/488,801.

Office Action dated Sep. 15, 2009 issued in related U.S. Appl. No. 10/365,170.

Office Action dated Jun. 22, 2009 issued in related U.S. Appl. No. 10/486,807.

Office Action dated Sep. 17, 2009 issued in related U.S. Appl. No. 11/318,207.

Office Action dated Jan. 27, 2010 issued in related U.S. Appl. No. 10/746,222.
Office Action dated Jan. 29, 2010 issued in related U.S. Appl. No. 10/488,801.
Office Action dated Jan. 19, 2010 issued in related U.S. Appl. No. 10/486,807.
Office Action dated Apr. 26, 2010 issued in related U.S. Appl. No. 11/537,852.
Office Action dated Mar. 18, 2010 issued in related U.S. Appl. No. 10/365,170.
Notice of Allowance dated Apr. 2, 2010 issued in related U.S. Appl. No. 11/274,908.
Supplemental Notice of Allowance dated May 27, 2010 issued in related U.S. Appl. No. 11/274,908.
Office Action dated Apr. 5, 2010 issued in related U.S. Appl. No. 11/318,207.
English language abstract for JP 2002-65692, published Mar. 5, 2002, data supplied from espacement, 1 page.
Beer, E., "Removal of Neoplasms of the Urinary Bladder,"*JAMA*, Sep. 9, 1983, vol. 250, No. 10, pp. 1324-1325.
Mittleman, R.S. et al., "Use of the Saline Infusion Electrode Catherter for Improved Energy Delivery and Increase Lesion Size in Radiofrequency Catheter Ablation,"*PACE*, May 1995, Part I, vol. 18, pp. 1022-1027.
Sakatani, K. et al., "Isotonic mannitol and the prevention of local heat generation and tissue adherence to bipolar diathermy forceps tips during electrical coagulation", *J. Neurosurg.*, Apr. 1995, vol. 82, pp. 669-671.
Office Communication, dated Feb. 8, 2005, for U.S. Appl. No. 10/365,170, filed Feb. 11, 2003, 6 pages.
Office Communication, dated Oct. 4, 2005, for U.S. Appl. No. 10/365,170, filed Feb. 11, 2003, 8 pages.
Office Communication, dated Dec. 6, 2006, for U.S. Appl. No. 10/365,170, filed Feb. 11, 2003, 5 pages.
Office Communication, dated Mar. 26, 2008, for U.S. Appl. No. 10/365,170, filed Feb. 11, 2003, 9 pages.
Office Communication, dated Jan. 12, 2009, for U.S. Appl. No. 10/365,170, filed Feb. 11, 2003, 13 pages.
Office Communication, dated Nov. 9, 2010, for U.S. Appl. No. 10/365,170, filed Feb. 11, 2003, 13 pages.
Office Communication, dated Jul. 17, 2009, for U.S. Appl. No. 11/274,908, filed Nov. 14, 2005, 12 pages.
Office Communication, dated Jun. 29, 2006, for U.S. Appl. No. 11/318,207, filed Dec. 22, 2005, 4 pages.
Office Communication, dated Jul. 1, 2008, for U.S. Appl. No. 11/318,207, filed Dec. 22, 2005, 7 pages.
Office Communication, dated Dec. 30, 2008, for U.S. Appl. No. 11/318,207, filed Dec. 22, 2005, 10 pages.
Office Communication, dated Oct.15, 2010, for U.S. Appl. No. 11/318,207, filed Dec. 22, 2005, 9 pages.

English language abstract for JP 2002-65692, published Mar. 5, 2002, data supplied from espacenet, 1 page.
Beer, E., "Removal of Neoplasms of the Urinary Bladder," *JAMA*, Sep. 9, 1983, vol. 250, No. 10, pp. 1324-1325.
Carter, J.E., "Suture? Staple? Electrosugery? How to Decide What is Best For You," *JSLS*, 1997, pp. 171-174.
Matek, W. et al., "Modified Electrocoagulation and Its Possibilities in the Control of Gastointestinal Bleeding," *Endoscopy*, 1979 pp. 253-258.
Mittleman, R.S. et al., "Use of the Saline Infusion Electrode Catheter for Improved Energy Delivery and Increased Lesion Size in Radiofrequency Catheter Ablation," PACE, May 1995, Part I, vol. 18, pp. 1022-1027.
Sakatani, K. et al., "Isotonic mannitol and the prevention of local heat generation and tissue adherence to bipolar diathermy forceps tips during electrical coagulation", *J. Neurosurg.*, Apr. 1995, vol. 82, pp. 669-671.
Sun, W., "Ablation Pathway Currents of a Linear Phased Multi-Electrode System," *Proceedings of the 20th Annual International Conference of the IEEE Engineering in Medicine and Biology Society*, 1998, vol. 20, No. 1, pp. 248-251.
Takao, T. et al., "Effect of Cautery with Irrigation Forceps on the Remnant Liver after Hepatectomy in Rats", *Eur. Surg. Res.*, 1999, vol. 31, pp. 173-179.
*TissueLink Floating Ball™: Better Surgery By Sealing Tissue*, TissueLink Medical, Inc., Brochure No. 71-100001-001, Rev B, Copyright 2001, 4 pages.
*TissueLink Floating Ball™: Better Surgery By Sealing Tissue*, TissueLInk Medical, Inc., Brochure No. 71-100001-001, Rev C, Copyright 2001, 4 pages.
Yamamoto, Y. et al., "New Simple Technique for Hepatic Parenchymal Resection Using a Cavitron Ultrasonic Surgical Aspirator® and Bipolar Cautery Equipped with a Channel for Water Dripping", *World Journal of Surgery*, 1999, vol. 23, pp. 1032-1037.
Yasargil. M.G., *Microsurgery Applied to Neurosurgery*, New York: Academic Press, 1969, pp. 41-45.
Office Communication, dated Feb. 8, 2005, for U.S. Appl. No. 10/365,170, filed Feb. 11, 2003, 6 pages.
Office Communication, dated Oct. 4, 2005, for U.S. Appl. No. 10/365,170, filed Feb. 11, 2003, 8 pages.
Office Communication, dated Dec. 6, 2006, for U.S. Appl. No. 10/365,170, filed Feb. 11, 2003, 5 pages.
Office Communication, dated Mar. 26, 2008, for U.S. Appl. No. 10/365,170, filed Feb. 11, 2003, 9 pages.
Office Communication, dated Jan. 12, 2009, for U.S. Appl. No. 10/365,170, filed Feb. 11, 2003, 13 pages.
Office Communication, dated Nov. 9, 2010, for U.S. Appl. No. 10/365,170, filed Feb. 11, 2003, 13 pages.

* cited by examiner

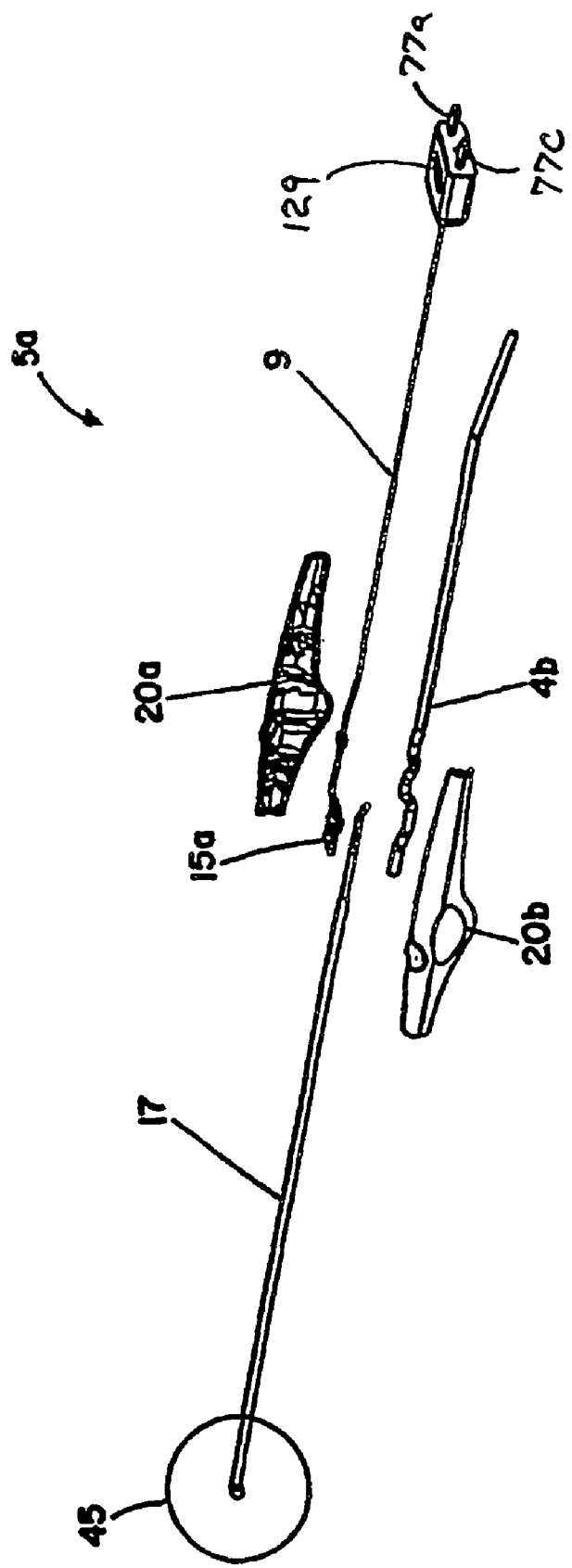

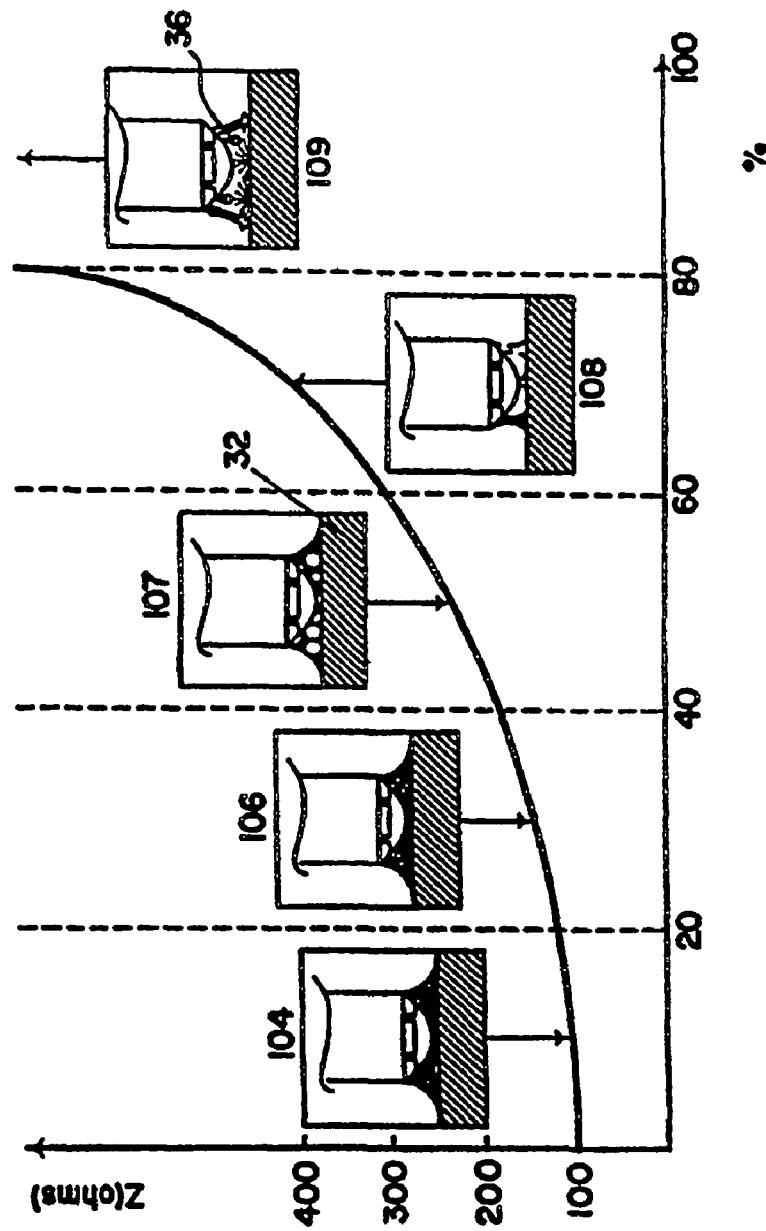

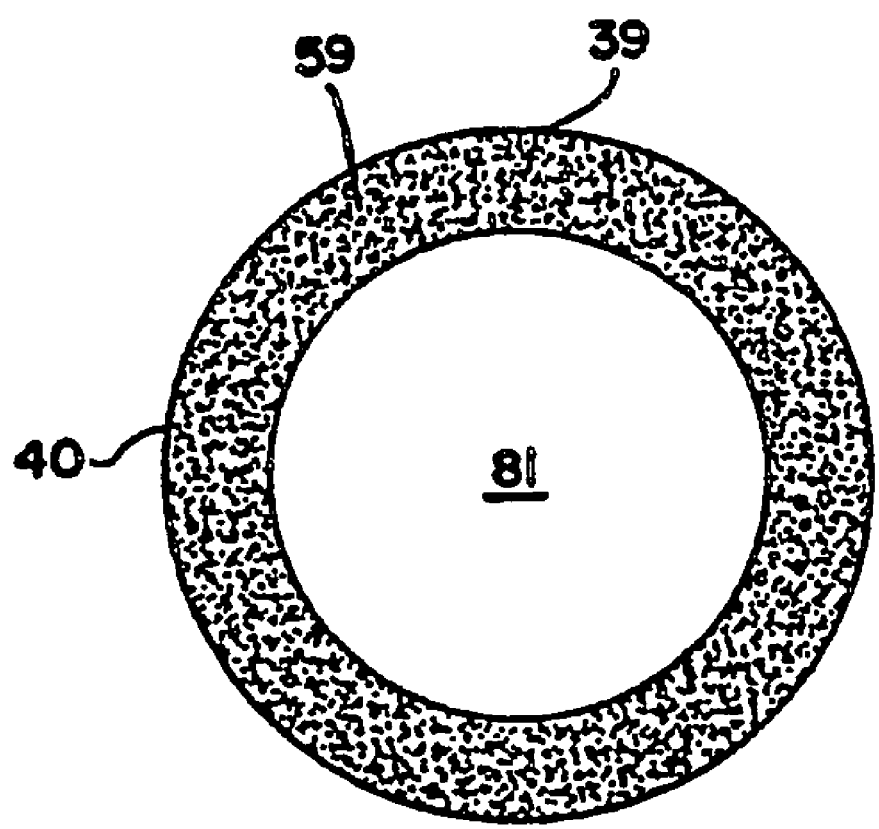

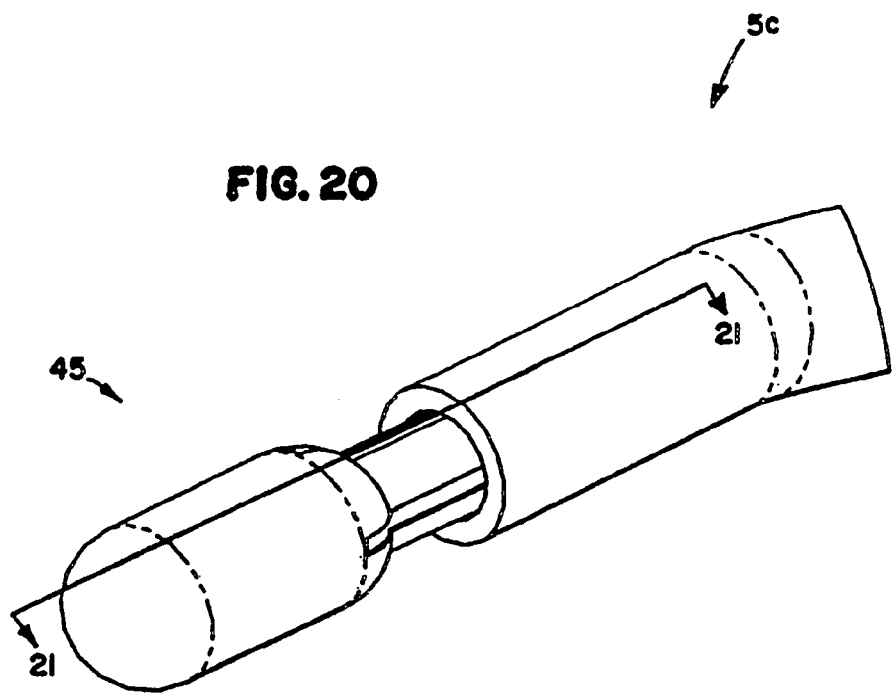
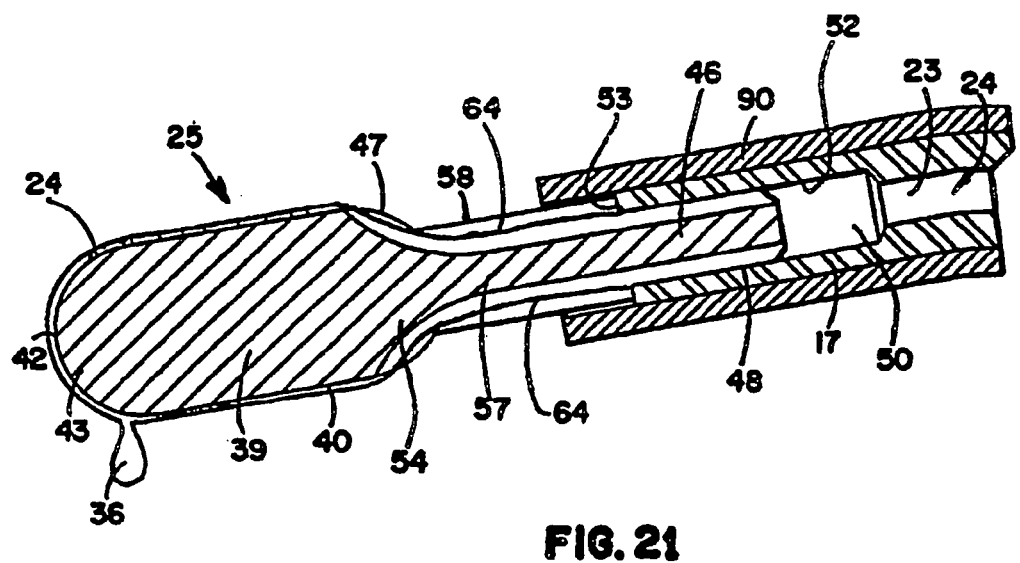

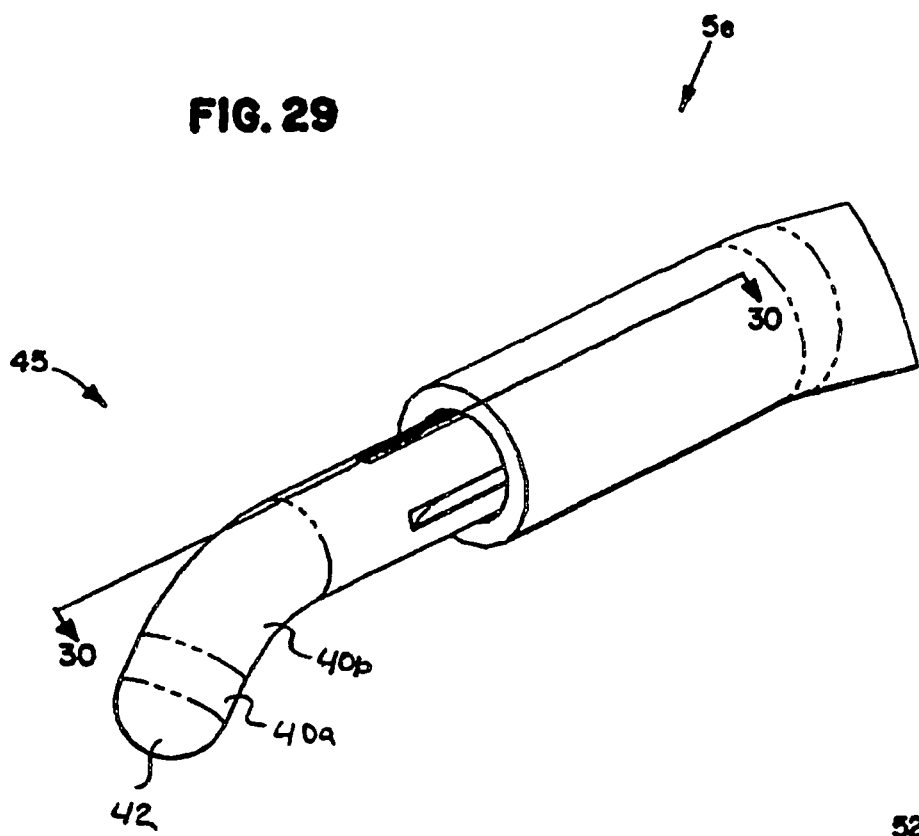
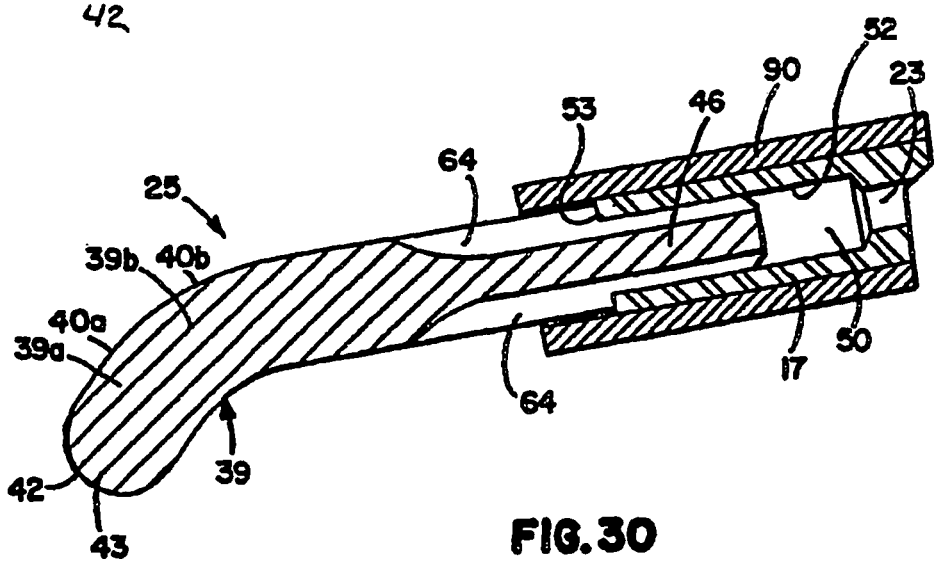

FLUID-ASSISTED MEDICAL DEVICES, SYSTEMS AND METHODS

CROSS REFERENCE TO RELATED APPLICATIONS

This patent application is a continuation of U.S. patent application Ser. No. 10/486,807, filed Sep. 15, 2004, now abandoned and PCT patent application serial no. PCT/US03/09763, filed Mar. 27, 2003, now pending, which claims priority under 35 U.S.C. §119(e) to U.S. provisional application Ser. No. 60/453,093, filed Mar. 6, 2003, to U.S. patent application Ser. No. 10/365,170, filed Feb. 11, 2003 and U.S. provisional application Ser. No. 60/368,177, filed Mar. 27, 2002.

This patent application is also a continuation-in-part of U.S. patent application Ser. No. 10/365,170, filed Feb. 11, 2003, now pending, which claims priority under 35 U.S.C. §119(e) to U.S. provisional application Ser. Nos. 60/368,177, filed Mar. 27, 2002, and 60/356,390, filed Feb. 12, 2002.

The entire disclosure of each of these patent applications is incorporated herein by reference to the extent it is consistent.

FIELD

This invention relates generally to the field of medical devices and methods for use upon a body during surgery. More particularly, the invention relates to electrosurgical devices, systems and methods for use upon tissues of a human body during surgery, particularly open surgery and minimally invasive surgery such as laparoscopic surgery.

BACKGROUND

Electrosurgical devices configured for use with a dry tip use electrical energy, often radio frequency (RF) energy, to cut tissue or to cauterize blood vessels. During use, a voltage gradient is created at the tip of the device, thereby inducing current flow and related heat generation in the tissue. With sufficiently high levels of electrical power, the heat generated is sufficient to cut the tissue and, advantageously, to stop the bleeding from severed blood vessels.

Current dry tip electrosurgical devices can cause the temperature of tissue being treated to rise significantly higher than 100° C., resulting in tissue desiccation, tissue sticking to the electrodes, tissue perforation, char formation and smoke generation. Desiccation occurs when tissue temperature exceeds 100° C. and all of the intracellular water boils away, leaving the tissue extremely dry and much less electrically conductive. Peak temperatures of target tissue as a result of dry RF treatment can be as high as 320° C., and such high temperatures can be transmitted to adjacent tissue via thermal diffusion. Consequently, this may result in undesirable desiccation and thermal damage to the adjacent tissue.

The use of saline inhibits undesirable effects such as tissue desiccation, electrode sticking, smoke production and char formation. However, an uncontrolled or abundant flow rate of saline can provide too much electrical dispersion and cooling at the electrode/tissue interface. This reduces the temperature of the target tissue being treated, and, in turn, can result in longer treatment time to achieve the desired tissue temperature for treatment of the tissue. Long treatment times are undesirable for surgeons since it is in the best interest of the patient, physician and hospital, to perform surgical procedures as quickly as possible.

RF power delivered to tissue can be less than optimal when using general-purpose generators. Most general-purpose RF generators have modes for different waveforms (e.g., cut, coagulation, or blend) and device types (e.g., monopolar, bipolar), as well as power levels that can be set in watts. However, once these settings are chosen, the actual power delivered to tissue and associated heat generated can vary dramatically over time as tissue impedance changes during the course of RF treatment. This is because the power delivered by most generators is a function of tissue impedance, with the power ramping down as impedance either decreases toward zero or increases significantly to several thousand ohms. Current dry tip electrosurgical devices are not configured to address a change in power provided by the generator as tissue impedance changes or the associated effect on tissue, and rely on the surgeon's expertise to overcome this limitation.

SUMMARY OF THE INVENTION

The invention is directed to various embodiments of electrosurgical devices, systems and methods. In one preferred embodiment, an electrosurgical device has a handle, a shaft extending from the handle having a distal end, and an electrode tip having an electrode surface with at least a portion of the electrode tip extending distally beyond the distal end of the shaft. In one embodiment, preferably the portion of the electrode tip extending distally beyond the distal end of the shaft comprises a cone shaped portion. The device also has a fluid passage being connectable to a fluid source and at least one fluid outlet opening in fluid communication with the fluid passage.

In another preferred embodiment, the electrode tip extending distally beyond the distal end of the shaft has a neck portion and an enlarged end portion with the enlarged end portion located distal to the neck portion and comprising the cone shaped portion.

In another preferred embodiment, the fluid outlet opening is arranged to provide a fluid from the fluid source to the neck portion of the electrode tip.

In yet another preferred embodiment, the fluid outlet opening is arranged to provide a fluid from the fluid source towards the enlarged end portion of the electrode tip.

In another preferred embodiment, an electrosurgical device has a handle, and an electrode tip having an electrode surface with the electrode surface and comprising a cone shaped portion. The device also has a fluid passage being connectable to a fluid source and at least one fluid outlet opening in fluid communication with the fluid passage and arranged to provide a fluid from the fluid source to the cone shaped portion of the electrode tip.

The invention is also directed to a surgical method for treating tissue. The method includes providing tissue having a tissue surface, providing radio frequency power at a power level, providing an electrically conductive fluid at a fluid flow rate, providing an surgical device configured to simultaneously provide the radio frequency electrical power and the electrically conductive fluid to tissue, providing the electrically conductive fluid to the tissue at the tissue surface, forming a fluid coupling comprising the electrically conductive fluid which couples the tissue and the surgical device, providing the radio frequency power to the tissue at the tissue surface and below the tissue surface into the tissue through the fluid coupling, coagulating the tissue without cutting the tissue, and dissecting the tissue after coagulating the tissue. Preferably, the device comprises an electrode tip having an electrode surface, and comprising a cone shaped portion and a distal end. Also preferably, coagulating the tissue is performed with the cone shaped portion and dissecting is performed with the distal end of the device. In various embodiments, the dissection may be blunt as where the distal end of the device is blunt, or sharp as where the distal end of the device is pointed.

The invention is also directed to various embodiments of an adaptor for electrically coupling between an electrosurgical generator and a bipolar electrosurgical device. In one preferred embodiment, the adaptor comprises a power input connector for coupling the adaptor with a monopolar mode power output connector of the electrosurgical generator, a ground connector for coupling the adaptor with a ground connector of the electrosurgical generator, a first and a second power output connector, each for coupling the adaptor with a first and a second bipolar mode power input connector of the bipolar electrosurgical device, respectively, a transformer coupled between the power input connector and the first and second power output connectors, a monopolar hand switch connector for coupling the adaptor with a monopolar mode hand switch connector of the electrosurgical generator, and at least one bipolar mode hand switch connector for coupling the adaptor with a bipolar mode hand switch connector of the electrosurgical device.

The invention is also directed to various embodiments of a bipolar electrosurgical device. In one preferred embodiment, the device comprises a first electrode tip and a second electrode tip with the electrode tips coupled to an impedance transformer provided with the electrosurgical device, at least one fluid delivery passage being connectable to a fluid source, at least one fluid outlet opening in fluid communication with the at least one fluid delivery passage, the electrode tips configured to paint along a tissue surface in the presence of fluid from the fluid outlet opening as the tips are moved along the tissue surface whereby the tissue surface can be coagulated without cutting upon the application of radio frequency energy from the electrodes simultaneously with fluid from the fluid outlet opening while the tips are coupled with the fluid adjacent the tissue surface and moved along the tissue surface.

The invention is also directed to various embodiments of medical kits. In one preferred embodiment, the kit has an electrosurgical device configured to provide radio frequency power and a fluid to a tissue treatment site, and a transformer. In various embodiments, the electrosurgical device and transformer may be provided as separate connectable components, or integrally as a single piece.

BRIEF DESCRIPTION OF THE DRAWINGS

FIG. 9 is a schematic exploded perspective view of an assembly of an electrosurgical device according to the present invention;

FIG. 18 is a schematic graph that describes a relationship between percentage saline boiling (%) and impedance (Z, in ohms);

FIG. 19 is schematic close-up cross-sectional view of a sleeve taken along line 19-19 of FIG. 15;

FIG. 20 is a schematic close-up perspective view of an alternative tip portion;

FIG. 21 is a schematic close-up cross-sectional side view of the tip portion of FIG. 20 taken along line 21-21 of FIG. 20;

FIG. 29 is a schematic close-up perspective view of an alternative tip portion;

FIG. 30 is a schematic close-up cross-sectional side view of the tip portion of FIG. 29 taken along line 30-30 of FIG. 29;

DETAILED DESCRIPTION

Figure 1:
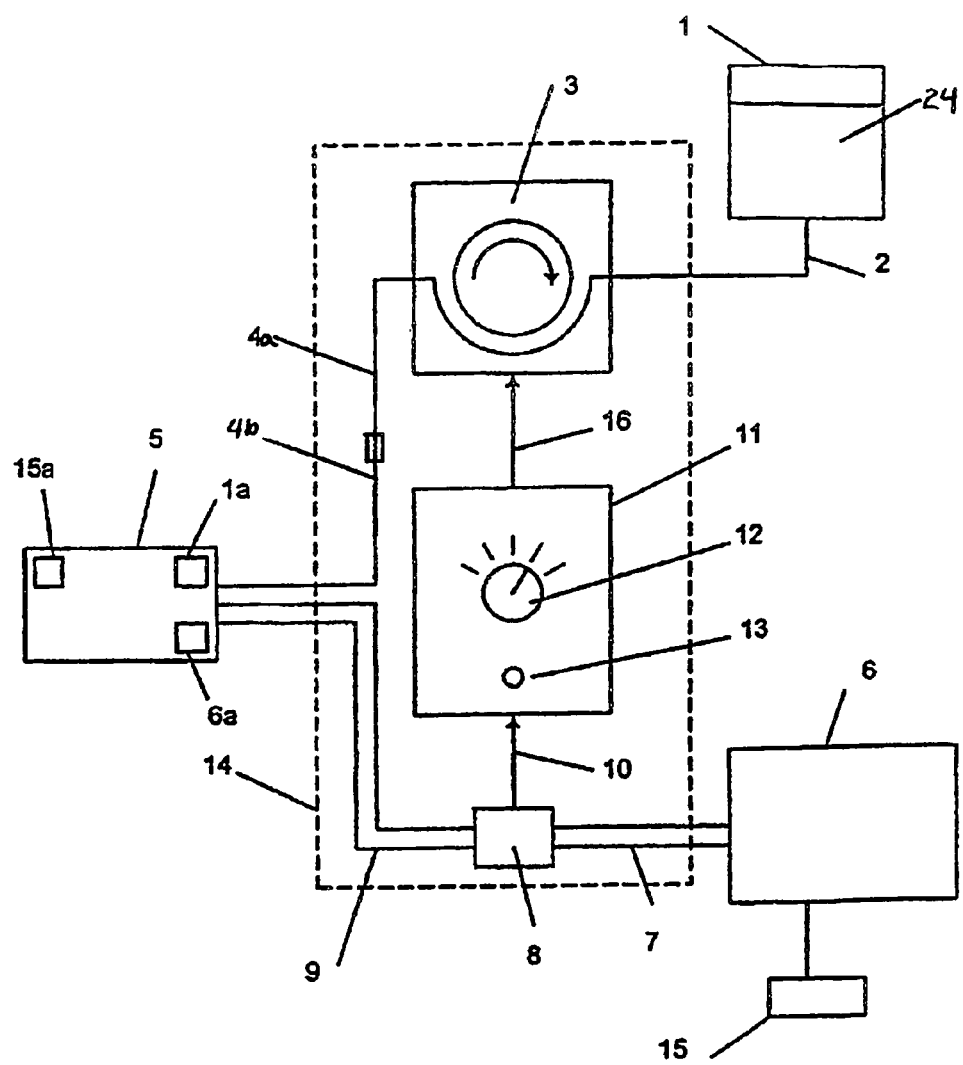
FIG. 1 is a block diagram showing one embodiment of a control system of the invention, and an electrosurgical device.

Throughout the description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this specification as suitable. In other words; features between the various exemplary embodiments described herein are interchangeable as suitable, and not exclusive.

The invention provides devices, systems and methods that control tissue temperature at a tissue treatment site during a medical procedure. This is particularly useful during surgical procedures upon tissues of the body, where it is desirable to seal, coagulate and shrink tissue, to occlude lumens of blood vessels (e.g., arteries, veins), airways (e.g., bronchi, bronchioles), bile ducts and lymphatic ducts.

The invention includes electrosurgical procedures, which preferably utilize RF power and electrically conductive fluid, to treat tissue. Preferably, a desired tissue temperature range is achieved by adjusting parameters, such as fluid flow rate, to affect the temperature at the tissue/electrode interface.

In one embodiment, the invention provides a control device, the device comprising a flow rate controller that receives a signal indicating power applied to the system, and adjusts the flow rate of fluid from a fluid source to the electrosurgical device. The invention also provides a control system comprising a flow rate controller, a measurement device that measures power applied to the system, and a pump that provides fluid at a selected flow rate.

The invention will be discussed generally with reference to FIG. 1, which shows a block diagram of one exemplary embodiment of a system of the invention. Preferably, an electrically conductive fluid 24 is provided from a fluid source 1 through a fluid line 2 to a pump 3, which has an outlet fluid line 4a that is connected as an input fluid line 4b to electrosurgical device 5. In a preferred embodiment, outlet fluid line 4a and input fluid line 4b are flexible and are made from a polymeric material, such as polyvinylchloride (PVC) or polyolefin (e.g., polypropylene, polyethylene) and the conductive fluid comprises a saline solution. More preferably, the saline comprises sterile, and even more preferably, normal saline. Although the description herein will specifically describe the use of saline as the fluid 24, other electrically conductive fluids, as well as non-conductive fluids, can be used in accordance with the invention.

For example, in addition to the conductive fluid comprising physiologic saline (also known as "normal" saline, isotonic saline or 0.9% sodium chloride (NaCl) solution), the conductive fluid may comprise hypertonic saline solution, hypotonic saline solution, Ringers solution (a physiologic solution of distilled water containing specified amounts of sodium chloride, calcium chloride, and potassium chloride), lactated Ringer's solution (a crystalloid electrolyte sterile solution of distilled water containing specified amounts of calcium chloride, potassium chloride, sodium chloride, and sodium lactate), Locke-Ringer's solution (a buffered isotonic solution of distilled water containing specified amounts of sodium chloride, potassium chloride, calcium chloride, sodium bicarbonate, magnesium chloride, and dextrose), or any other electrolyte solution.

While a conductive fluid is preferred, as will become more apparent with further reading of this specification, fluid 24 may also comprise an electrically non-conductive fluid. The use of a non-conductive fluid is less preferred than a conductive fluid, however, the use of a non-conductive fluid still provides certain advantages over the use of a dry electrode including, for example, reduced occurrence of tissue sticking to the electrode of device 5 and cooling of the electrode and/or tissue. Therefore, it is also within the scope of the invention to include the use of a non-conducting fluid, such as, for example, deionized water.

Returning to FIG. 1, energy to heat tissue is provided from an energy source, such as an electrical generator 6 which preferably provides RF alternating current via a cable 7 to an energy source output measurement device, such as a power measurement device 8 that measures the RF alternating current electrical power. In one exemplary embodiment, preferably the power measurement device 8 does not turn the power off or on, or alter the power in any way. A power switch 15 connected to generator 6 is preferably provided by the generator manufacturer and is used to turn generator 6 on and off. The power switch 15 can comprise any switch to turn the power on and off, and is commonly provided in the form of a footswitch or other easily operated switch, such as a switch 15a mounted on electrosurgical device 5. The power switch 15 or 15a may also function as a manually activated device for increasing or decreasing the power provided from device 5. Alternatively, internal circuitry and other components of generator 6 may be used for automatically increasing or decreasing the power provided from device 5. A cable 9 preferably provides RF power from power measurement device 8 to electrosurgical device 5. Power, or any other energy source output, is preferably measured before it reaches electrosurgical device 5.

When capacitation and induction effects are negligibly small, from Ohm's law, power P, or the rate of energy delivery (e.g., joules/sec), may be expressed by the product of current times voltage (i.e., I×V), the current squared times resistance (i.e., $I^2 \times R$), or the voltage squared divided by the resistance (i.e., $V^2/R$); where the current I may be measured in amperes, the voltage V may be measured in volts, the electrical resistance R may be measured in ohms, and the power P may be measured in watts (joules/sec). Given that power P is a function of current I, voltage V, and resistance R as indicated above, it should be understood, that a change in power P is reflective of a change in at least one of the input variables. Thus, one may alternatively measure changes in such input variables themselves, rather than power P directly, with such changes in the input variables mathematically corresponding to a changes in power P as indicated above.

Heating of the tissue is preferably performed by electrical resistance heating. That is, the temperature of the tissue increases as a result of electric current flow through the tissue, with the electrical energy being absorbed from the voltage and transformed into thermal energy (i.e., heat) via accelerated movement of ions as a function of the tissue's electrical resistance.

Referring again to FIG. 1, a flow rate controller 11 preferably includes a selection switch 12 that can be set to achieve desired levels of percentage fluid boiling (for example, 100%, 98%, 80% boiling). Preferably, flow rate controller 11 receives an input signal 10 from power measurement device 8 and calculates an appropriate mathematically predetermined fluid flow rate based on percentage boiling indicated by the selection switch 12. In a preferred embodiment, a fluid switch 13 is provided so that the fluid system can be primed (e.g., air eliminated) before turning on generator 6. The output signal 16 of flow rate controller 11 is preferably sent to pump 3 motor to regulate the flow rate of fluid, and thereby provide an appropriate fluid flow rate which corresponds to the amount of power being delivered.

In one embodiment, flow rate controller 11 is configured and arranged to be connected to a source of RF power (e.g., generator 6), and a source of fluid (e.g., fluid source 1), for example, a source of conductive fluid. The device of the invention receives information about the level of RF power applied to electrosurgical device 5, and adjusts the flow rate of fluid 24 to electrosurgical device 5, thereby controlling temperature at the tissue treatment site.

In another embodiment, elements of the system are physically included together in one electronic enclosure. One such embodiment is shown by enclosure within the outline box 14 of FIG. 1. In the illustrated embodiment, pump 3, flow rate controller 11, and power measurement device 8 are enclosed within an enclosure, and these elements are connected through electrical connections to allow signal 10 to pass from power measurement device 8 to flow rate controller 11, and signal 16 to pass from flow rate controller 11 to pump 3. Other elements of a system can also be included within one enclosure, depending upon such factors as the desired application of the system, and the requirements of the user.

Pump 3 can be any suitable pump to provide saline or other fluid at a desired flow rate. Preferably, pump 3 is a peristaltic pump. With a rotary peristaltic pump, typically a fluid 24 is conveyed within the confines of a flexible tube (e.g., 4a) by waves of contraction placed externally on the tube which are produced mechanically, typically by rotating rollers which intermittently squeeze the flexible tubing against a support with a linear peristaltic pump, typically a fluid 24 is conveyed within the confines of a flexible tube by waves of contraction placed externally on the tube which are produced mechanically, typically by a series of compression fingers or pads which sequentially squeeze the flexible tubing against a support. Peristaltic pumps are generally preferred, as the electromechanical force mechanism (e.g., rollers driven by electric motor) does not make contact the fluid 24, thus reducing the likelihood of inadvertent contamination.

Similar pumps can be used in connection with the invention, and the illustrated embodiments are exemplary only. The precise configuration of pump 3 is not critical to the invention. For example, pump 3 may include other types of infusion and withdrawal pumps. Furthermore, pump 3 may comprise pumps which may be categorized as syringe pumps, piston pumps, rotary vane pumps (e.g., axial impeller, centrifugal impeller), cartridge pumps and diaphragm pumps. In some embodiments, pump 3 can be substituted with any type of flow controller, such as a manual roller clamp used in conjunction with an IV bag, or combined with the flow controller to allow the user to control the flow rate of conductive fluid to the device. Alternatively, a valve configuration can be substituted for pump 3.

Fluid 24, such as conductive fluid, is preferably provided from an intravenous (IV) bag full of saline (e.g., fluid source 1) that flows by gravity. Fluid 24 may flow directly to electrosurgical device 5, or first to pump 3 located there between. Alternatively, fluid 24 from a fluid source 1 such as an IV bag can be provided through an IV flow controller that may provide a desired flow rate by adjusting the cross sectional area of a flow orifice (e.g., lumen of the connective tubing with the electrosurgical device 5) while sensing the flow rate with a sensor such as an optical drop counter. Furthermore, fluid 24 from a fluid source 1 such as an IV bag can be provided through a manually or automatically activated device such as a flow controller, such as a roller clamp, which also adjusts the cross sectional area of a flow orifice and may be adjusted manually by, for example, the user of the device in response to their visual observation (e.g., fluid boiling) at the tissue treatment site or a pump.

Similar configurations of the system can be used in connection with the invention, and the illustrated embodiments are exemplary only. For example, the fluid source 1, pump 3, generator 6, power measurement device 8 or flow rate controller 11, or any other components of the system not expressly recited above, may be present as a part of the electrosurgical device 5. For example, fluid source 1 may be a compartment of the electrosurgical device 5 which contains fluid 24, as indicated at reference character 1a. In another exemplary embodiment, the compartment may be detachably connected to electrosurgical device 5, such as a canister which may be attached via threaded engagement with device 5. In yet another embodiment, the compartment may be configured to hold a pre-filled cartridge of fluid 24, rather than the fluid directly.

Also for example, with regards to alternatives for the generator 6, an energy source, such as a direct current (DC) battery used in conjunction with inverter circuitry and a transformer to produce alternating current at a particular frequency, may comprise a portion of the electrosurgical device 5, as indicated at reference character 6a. In one embodiment the battery element of the energy source may comprise a rechargeable battery. In yet another exemplary embodiment, the battery element may be detachably connected to the electrosurgical device 5, such as for recharging.

Use of the components of the system will now be described in further detail. From the specification, it should be clear that any use of the terms "distal" and "proximal" are made in reference from the user of the device, and not the patient.

Figure 2:
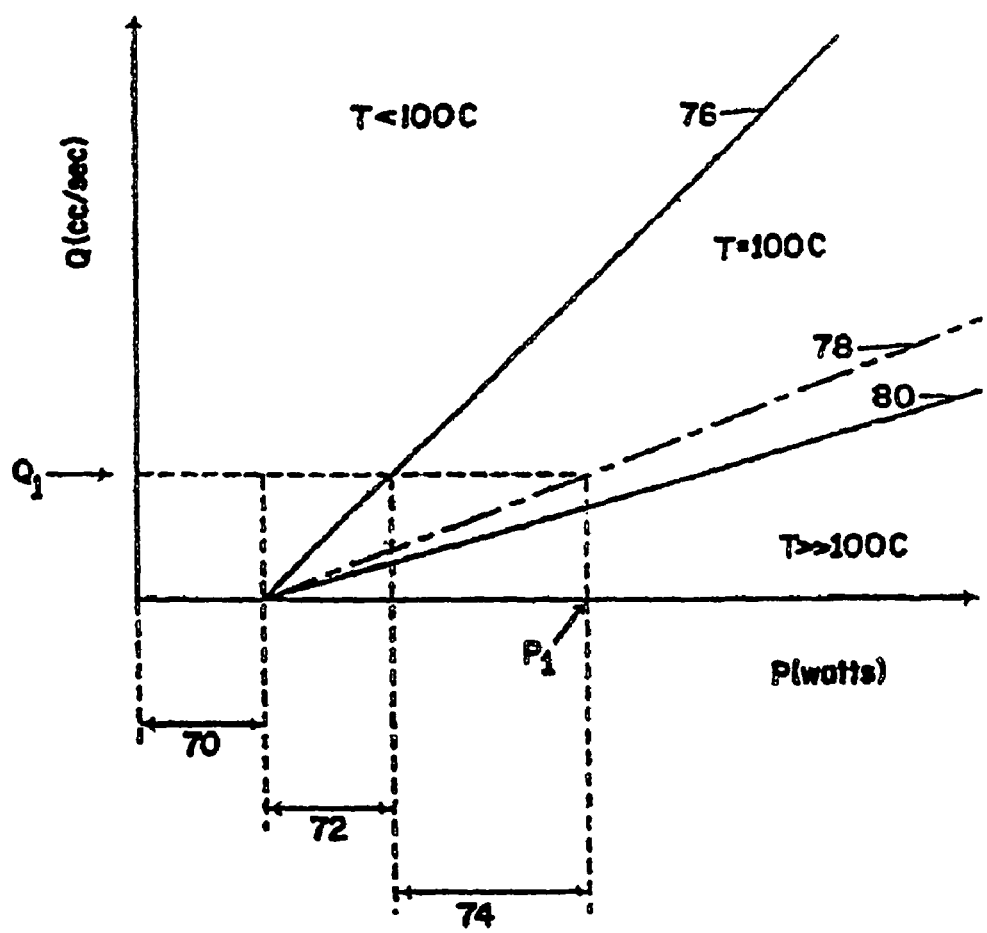
FIG. 2 is a schematic graph that describes a relationship between RF power to tissue (P, in watts), flow rate of saline (Q, in cc/sec.), and tissue temperature (T, in ° C.) when heat conduction to adjacent tissue is considered.

Flow rate controller 11 controls the rate of flow from the fluid source 1. Preferably, the rate of fluid flow from fluid source 1 is based upon the amount of RF power provided from generator 6 to electrosurgical device 5. Referring to FIG. 2, there is illustrated a relationship between the rate of fluid flow Q and the RF power P. More precisely, as shown in FIG. 2, the relationship between the rate of fluid flow Q and RF power P may be expressed as a direct, linear relationship. The flow rate Q of conductive fluid 24, such as saline, interacts with the RF power P and various modes of heat transfer to transfer heat away from the target tissue, as described herein.

Throughout this disclosure, when the terms "boiling point of saline", "vaporization point of saline", and variations thereof are used, what is actually referenced for explanation purposes, is the boiling point of the water (i.e., 100° C.) in the saline solution given that the difference between the boiling point of normal saline (about 100.16° C.) and the boiling point of water is negligible.

FIG. 2 shows the relationship between the flow rate of saline, RF power to tissue, and regimes of boiling as detailed below. Based on a simple, one-dimensional, lumped parameter model of the heat transfer, the peak tissue temperature can be estimated, and once tissue temperature is estimated, it follows directly whether it is hot enough to boil saline. The total RF electrical power P that is converted into heat can be defined as:

$$P = \Delta T/R + \rho c_\rho Q_1 \Delta T + \rho Q_b h_v \quad (1)$$

where P=the total RF electrical power that is converted into heat.

Conduction. The first term [$\Delta T/R$] in equation (1) is heat conducted to adjacent tissue, represented as 70 in FIG. 2, where:
$\Delta T = (T - T_\infty)$ the difference in temperature (° C.) between the peak tissue temperature (T) and the normal temperature ($T_\infty$) of the body tissue; normal temperature of the body tissue is generally 37° C.; and
R=Thermal resistance of surrounding tissue, the ratio of the temperature difference to the heat flow (° C./watt).

This thermal resistance can be estimated from published data gathered in experiments on human tissue (see for example, Phipps, J. H., "Thermometry studies with bipolar diathermy during hysterectomy," *Gynaecological Endoscopy*, 3:5-7 (1994)). As described by Phipps, Kleppinger bipolar forceps were used with an RF power of 50 watts, and the peak tissue temperature reached 320° C. For example, using the energy balance of equation (1), and assuming all the RF heat put into tissue is conducted away, then R can be estimated:

$$R = \Delta T/P = (320 - 37)/50 = 5.7 \approx 6° C./watt$$

However, it is undesirable to allow the tissue temperature to reach 320° C., since tissue will become desiccated. At a temperature of 320° C., the fluid contained in the tissue is typically boiled away, resulting in the undesirable tissue effects described herein. Rather, it is preferred to keep the peak tissue temperature at no more than about 100° C. to inhibit desiccation of the tissue. Assuming that saline boils at about 100° C., the first term in equation (1) ($\Delta T/R$) is equal to (100−37)/6=10.5 watts. Thus, based on this example, the maximum amount of heat conducted to adjacent tissue without any significant risk of tissue desiccation is 10.5 watts.

Referring again to FIG. 2, RF power to tissue is represented on the X-axis as P (watts) and flow rate of saline (cc/min) is represented on the Y-axis as Q. When the flow rate of saline equals zero (Q=0), there is an "offset" RF power that shifts the origin of the sloped lines 76, 78, and 80 to the right. This offset is the heat conducted to adjacent tissue. For example, using the calculation above for bipolar forceps, this offset RF power is about 10.5 watts. If the power is increased above this level with no saline flow, the peak tissue temperature can rise well above 100° C., resulting in tissue desiccation from the boiling off of water in the cells of the tissue.

Convection. The second term [$\rho c_\rho Q_1 \Delta T$] in equation (1) is heat used to warm up the saline without boiling the saline, represented as 72 in FIG. 2, where:
$\rho$=Density of the saline fluid that gets hot but does not boil (approximately 1.0 gm/cm$^3$);
$c_\rho$=Specific heat of the saline (approximately 4.1 watt-sec/gm-° C.);
$Q_1$=Flow rate of the saline that is heated (cm$^3$/sec); and
$\Delta T$=Temperature rise of the saline. Assuming that the saline is heated to body temperature before it reaches the electrode, and that the peak saline temperature is similar to the peak tissue temperature, this is the same $\Delta T$ as for the conduction calculation above.

The onset of boiling can be predicted using equation (1) with the last term on the right set to zero (no boiling), i.e. $\rho Q_b h_v = 0$, and solving equation (1) for $Q_1$ leads to:

$$Q_1 = [P - \Delta T/R]/\rho c_\rho \Delta T \quad (2)$$

This equation defines the line shown in FIG. 2 as the line of onset of boiling 76.

Boiling. The third term [$\rho Q_b h_v$] in equation (1) relates to heat that goes into converting the water in liquid saline to water vapor, and is represented as 74 in FIG. 2, where:
$Q_b$=Flow rate of saline that boils (cm$^3$/sec); and
$h_v$=Heat of vaporization of saline (approximately 2,000 watt-sec/gm).

A flow rate of only 1 cc/min will absorb a significant amount of heat if it is completely boiled, or about $\rho Q_b h_v = (1)(1/60)(2,000) = 33.3$ watts. The heat needed to warm this flow rate from body temperature to 100° C. is much less, or $\rho c_\rho Q_1 \Delta T = (1)(4.1)(1/60)(100-37) = 4.3$ watts. In other words, the most significant factor contributing to heat transfer from a wet electrode device can be fractional boiling. The present invention recognizes this fact and exploits it.

Fractional boiling can be described by equation (3) below:

$$Q_1 = \frac{\{P - \Delta T / R\}}{\{\rho c_p \Delta T + \rho h_v Q_b / Q_l\}} \quad (3)$$

If the ratio of $Q_b/Q_1$ is 0.50 this is the 50% boiling line 78 shown in FIG. 2. If the ratio is 1.0 this is the 100% boiling line 80 shown in FIG. 2.

As indicated previously in the specification, use of a fluid to couple energy to tissue inhibits undesirable effects such as tissue desiccation, electrode sticking, char formation and smoke production. Tissue desiccation, which occurs if the tissue temperature exceeds 100° C. and all the intracellular water boils away, is particularly undesirable as it leaves the tissue extremely dry and much less electrically conductive.

As shown in FIG. 2, one control strategy or mechanism which can be employed for the electrosurgical device 5 is to adjust the power P and flow rate Q such that the power P used at a corresponding flow rate Q is equal to or less than the power P required to boil 100% of the fluid, and does not exceed the power P required to boil 100% of the fluid. This control strategy targets using the electrosurgical device 5 in the regions of FIG. 2 identified as T<100° C. and T=100° C., and includes the 100% boiling line 80. That is, this control strategy targets not using the electrosurgical device 5 only in the region of FIG. 2 identified as T>>100° C.

Another control strategy that can be used for the electrosurgical device 5 is to operate device 5 in the region T<100° C., but at high enough temperature to shrink tissue containing Type I collagen (e.g., walls of blood vessels, bronchi, bile ducts, etc.), which shrinks when exposed to about 85° C. for an exposure time of 0.01 seconds, or when exposed to about 65° C. for an exposure time of 15 minutes. An exemplary target temperature/time for tissue shrinkage is about 75° C. with an exposure time of about 1 second. A determination of the high end of the scale (i.e., when the fluid reaches 100° C.) can be made by the phase change in the fluid from liquid to vapor. However, a determination at the low end of the scale (e.g., when the fluid reaches, for example, 75° C. for 1 second) requires a different mechanism as the temperature of the fluid is below the boiling temperature and no such phase change is apparent.

In order to determine when the fluid reaches a temperature that will facilitate tissue shrinkage, for example 75° C., a thermochromic material, such as a thermochromic dye (e.g., leuco dye), may be added to the fluid. The dye can be formulated to provide a first predetermined color to the fluid at temperatures below a threshold temperature, such as 75° C., then, upon heating above 75° C., the dye provides a second color, such as clear, thus turning the fluid clear (i.e., no color or reduction in color). This color change may be gradual, incremental, or instant. Thus, a change in the color of the fluid, from a first color to a second color (or lack thereof) provides a visual indication to the user of the electrosurgical device 5 as to when a threshold fluid temperature below boiling has been achieved. Thermochromic dyes are available, for example, from Color Change Corporation, 1740 Cortland Court, Unit A, Addison, Ill. 60101.

It is also noted that the above mechanism (i.e., a change in the color of the fluid due to a dye) may also be used to detect when the fluid reaches a temperature which will facilitate tissue necrosis; this generally varies from about 60° C. for an exposure time of 0.01 seconds and decreasing to about 45° C. for an exposure time of 15 minutes. An exemplary target temperature/time for tissue necrosis is about 55° C. for an exposure time of about 1 second.

In order to reduce time, use of the electrosurgical device 5 in the region T=100° C. of FIG. 2 is preferable to use of the electrosurgical device 5 in the region T<100° C. Consequently, as shown in FIG. 2, another control strategy which may be employed for the electrosurgical device 5 is to adjust the power P and flow rate Q such that the power P used at a corresponding flow rate Q is equal to or more than the power P required to initiate boiling of the fluid, but still less than the power P required to boil 100% of the fluid. This control strategy targets using the electrosurgical device 5 in the region of FIG. 2 identified as T=100° C., and includes the lines of the onset of boiling 76 and 100% boiling line 80. That is, this control strategy targets using the electrosurgical device 5 on or between the lines of the onset of boiling 76 and 100% boiling line 80, and not using the electrosurgical device 5 in the regions of FIG. 2 identified as T<100° C. and T>>100° C.

For consistent tissue effect, it is desirable to control the saline flow rate so that it is always on a "line of constant % boiling" as, for example, the line of the onset of boiling 76 or the 100% boiling line 80 or any line of constant % boiling located in between (e.g., 50% boiling line 78) as shown in FIG. 2. Consequently, another control strategy that can be used for the electrosurgical device 5 is to adjust power P and flow rate Q such that the power P used at a corresponding flow rate Q targets a line of constant % boiling.

It should be noted, from the preceding equations, that the slope of any line of constant % boiling is known. For example, for the line of the onset of boiling 76, the slope of the line is given by $(\rho c_p \Delta T)$, while the slope of the 100% boiling line 80 is given by $1/(\rho c_p \Delta T + \rho h_v)$. As for the 50% boiling line 78, for example, the slope is given by $1/(\rho c_p \Delta T + \rho h_v 0.5)$.

If, upon application of the electrosurgical device 5 to the tissue, boiling of the fluid is not detected, such indicates that the temperature is less than 100° C. as shown by the area T<100° C. of FIG. 2, and the flow rate Q must be decreased to initiate boiling if the power remains unchanged. The flow rate Q may be decreased until boiling of the fluid is first detected, at which time the line of the onset of boiling 76 is transgressed and the point of transgression on the line 76 is determined. From the determination of a point on the line of the onset of boiling 76 for a particular power P and flow rate Q, and the known slope of the line 76 as outlined above (i.e., $1/\rho c_p \Delta T$), it is also possible to determine the heat conducted to adjacent tissue 70.

Conversely, if upon application of the electrosurgical device 5 to the tissue, boiling of the fluid is detected, such indicates that the temperature is approximately equal to 100° C. as shown by the area T=100° C. of FIG. 2, and the flow rate Q must be increased to reduce boiling until boiling stops, at which time the line of the onset of boiling 76 is transgressed and the point of transgression on the line 76 determined. As with above, from the determination of a point on the line of the onset of boiling 76 for a particular power P and flow rate Q, and the known slope of the line 76, it is also possible to determine the heat conducted to adjacent tissue 70.

With regards to the detection of boiling of the fluid, preferably such is physically detected by the user (e.g., visually by the naked eye) in the form of either bubbles or steam evolving from the fluid coupling at the electrode/tissue interface. Alternatively, such a phase change (i.e., from liquid to vapor or vice-versa) may be measured by a sensor which preferably senses either an absolute change (e.g., existence or non-existence of boiling with binary response such as yes or no) or a change in a physical quantity or intensity and converts the change into a useful input signal for an information-gathering system. For example, the phase change associated with the onset of boiling may be detected by a pressure sensor, such as a pressure transducer, located on the electrosurgical device 5. Alternatively, the phase change associated with the onset of boiling may be detected by a temperature sensor, such as a thermistor or thermocouple, located on the electrosurgical device 5, such as adjacent to the electrode. Also alternatively, the phase change associated with the onset of boiling may be detected by a change in the electric properties of the fluid itself. For example, a change in the electrical resistance of the fluid may be detected by an ohm meter; a change in the amperage may be measured by an amp meter; a change in the voltage may be detected by a volt meter; and a change in the power may be determined by a power meter.

Figure 3:
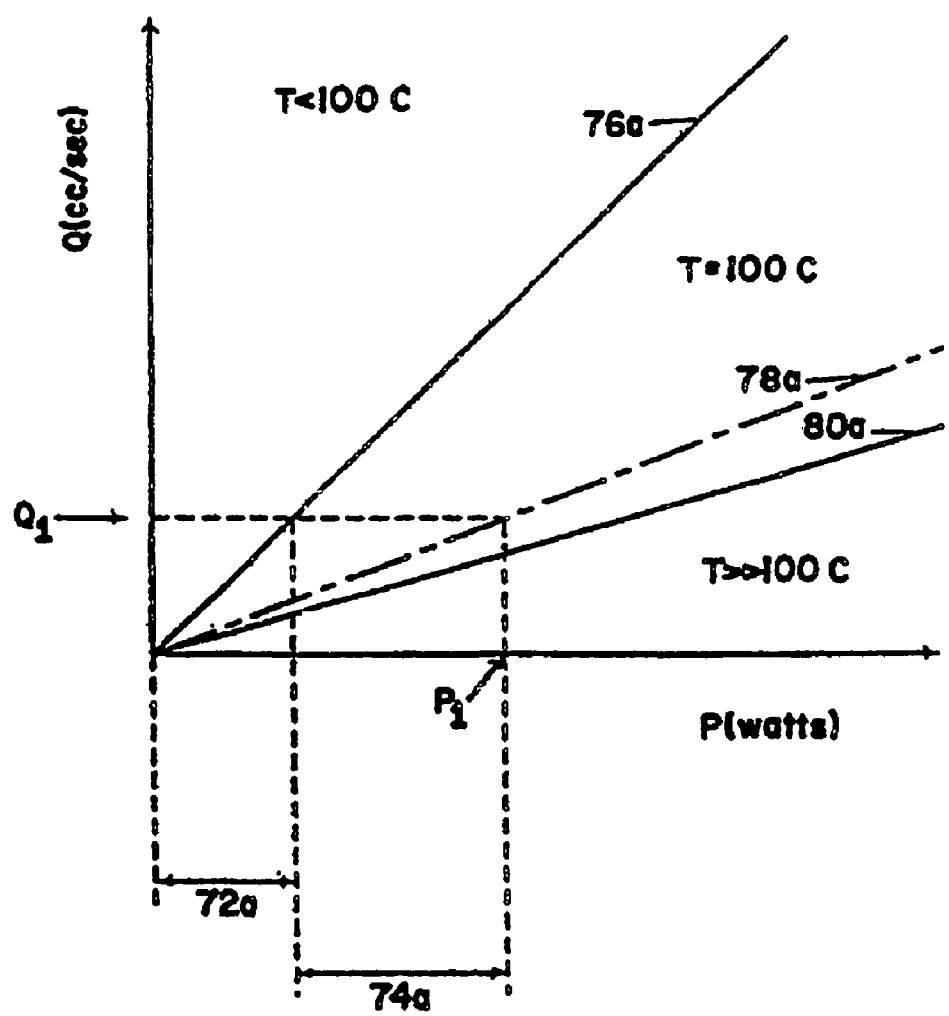
FIG. 3 is schematic graph that describes a relationship between RF power to tissue (P, in watts), flow rate of saline (Q, in cc/sec.), and tissue temperature (T, in ° C.) when heat conduction to adjacent tissue is neglected.

Yet another control strategy which may be employed for the electrosurgical device 5 is to eliminate the heat conduction term 70 of equation (1) (i.e., $\Delta T/R$). Since the amount of heat conducted away to adjacent tissue can be difficult to precisely predict, as it may vary, for example, by tissue type, it may be preferable, from a control point of view, to assume the worst case situation of zero heat conduction, and provide enough saline so that if necessary, all the RF power could be used to heat up and boil the saline, thus providing that the peak tissue temperature will not go over 100° C. significantly. This is shown in the schematic graph of FIG. 3.

Stated another way, if the heat conducted to adjacent tissue 70 is overestimated, the power P required to intersect the 100% boiling line 80 will, in turn, be overestimated and the 100% boiling line 80 will be transgressed into the T>>100° C. region of FIG. 2, which is undesirable as established above. Thus, assuming the worse case situation of zero heat conduction provides a "safety factor" to avoid transgressing the 100% boiling line 80. Assuming heat conduction to adjacent tissue 70 to be zero also provides the advantage of eliminating the only term from equation (1) which is tissue dependent, i.e., depends on tissue type. Thus, provided $\rho$, $c_p$, $\Delta T$, and $h_v$ are known as indicated above, the equation of the line for any line of constant % boiling is known. Thus, for example, the 98% boiling line, 80% boiling line, etc. can be determined in response to a corresponding input from selection switch 12. In order to promote flexibility, it should be understood that the input from the selection switch preferably may comprise any percentage of boiling. Preferably the percentage of boiling can be selected in single percent increments (i.e., 100%, 99%, 98%, etc.).

Upon determination of the line of the onset of boiling 76, the 100% boiling line 80 or any line of constant % boiling there between, it is generally desirable to control the flow rate Q so that it is always on a particular line of constant % boiling for consistent tissue effect. In such a situation, flow rate controller 11 will adjust the flow rate Q of the fluid 24 to reflect changes in power P provided by the generator 6, as discussed in greater detail below. For such a use flow rate controller 11 may be set in a line of constant boiling mode, upon which the % boiling is then correspondingly selected.

As indicated above, it is desirable to control the saline flow rate Q so that it is always on a line of constant % boiling for consistent tissue effect. However, the preferred line of constant % boiling may vary based on the type of electrosurgical device 5. For example, if with use of the device 5, shunting through saline is not an issue, then it can be preferable to operate close to or directly on, but not over the line of the onset of boiling, such as 76a in FIG. 3. This preferably keeps tissue as hot as possible without causing desiccation. Alternatively, if with use of the device 5 shunting of electrical energy through excess saline is an issue, then it can be preferable to operate along a line of constant boiling, such as line 78a in FIG. 3, the 50% line. This simple proportional control will have the flow rate determined by equation (4), where K is the proportionality constant:

$$Q_l = K \times P \qquad (4)$$

In essence, when power P goes up, the flow rate Q will be proportionately increased. Conversely, when power P goes down, the flow rate Q will be proportionately decreased.

The proportionality constant K is primarily dependent on the fraction of saline that boils, as shown in equation (5), which is equation (3) solved for K after eliminating P using equation (4), and neglecting the conduction term ($\Delta T/R$):

$$K = \frac{1}{\{\rho c_p \Delta T + \rho h_v Q_b / Q_l\}} \qquad (5)$$

Thus, the present invention provides a method of controlling boiling of fluid, such as a conductive fluid, at the tissue/electrode interface. In a preferred embodiment, this provides a method of treating tissue without use of tissue sensors, such as temperature or impedance sensors. Preferably, the invention can control boiling of conductive fluid at the tissue/electrode interface and thereby control tissue temperature without the use of feedback loops.

In describing the control strategy of the present invention described thus far, focus has been drawn to a steady state condition. However, the heat required to warm the tissue to the peak temperature (T) may be incorporated into equation (1) as follows:

$$P = \Delta T/R + \rho c_p Q_l \Delta T + \rho Q_b h_v + \rho c_p V \Delta T / \Delta t \qquad (6)$$

where $\rho c_p V \Delta T / \Delta t$ represents the heat required to warm the tissue to the peak temperature (T) 68 and where:
  p=Density of the saline fluid that gets hot but does not boil (approximately 1.0 gm/cm³);
  $c_p$=Specific heat of the saline (approximately 4.1 watt-sec/gm-° C.);
  V=Volume of treated tissue;
  $\Delta T$=(T−T$_\infty$) the difference in temperature (° C.) between the peak tissue temperature (T) and the normal temperature (T$_\infty$) of the body tissue; normal temperature of the body tissue is generally 37° C.; and
  $\Delta t$ (t−t$_\infty$) the difference in time to achieve peak tissue temperature (T) and the normal temperature (T$_\infty$) of the body tissue (° C.).

Figure 4:
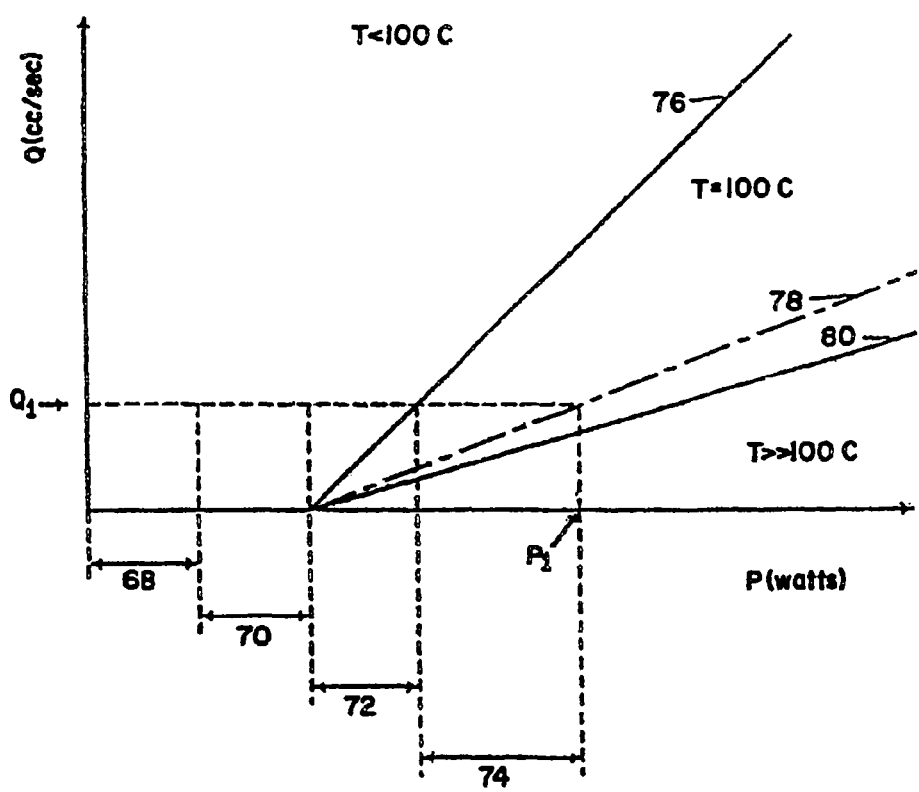
FIG. 4 is a schematic graph that describes a relationship between RF power to tissue (P, in watts), flow rate of saline (Q, in cc/sec.), and tissue temperature (T, in ° C.) when the heat required to warm the tissue to the peak temperature (T) is considered.

The inclusion of the heat required to warm the tissue to the peak temperature (T) in the control strategy is graphically represented at 68 in FIG. 4. With respect to the control strategy, the effects of the heat required to warm the tissue to the peak temperature (T) 68 should be taken into account before flow rate Q adjustment being undertaken to detect the location of the line of onset of boiling 76. In other words, the flow rate Q should not be decreased in response to a lack of boiling before at least a quasi-steady state has been achieved as the location of the line of onset of boiling 76 will continue to move during the transitory period. Otherwise, if the flow rate Q is decreased during the transitory period, it may be possible to decrease the flow Q to a point past the line of onset of boiling 76 and continue past the 100% boiling line 80 which is undesirable. In other words, as temperature (T) is approached the heat 68 diminishes towards zero such that the lines of constant boiling shift to the left towards the Y-axis.

Figure 5:
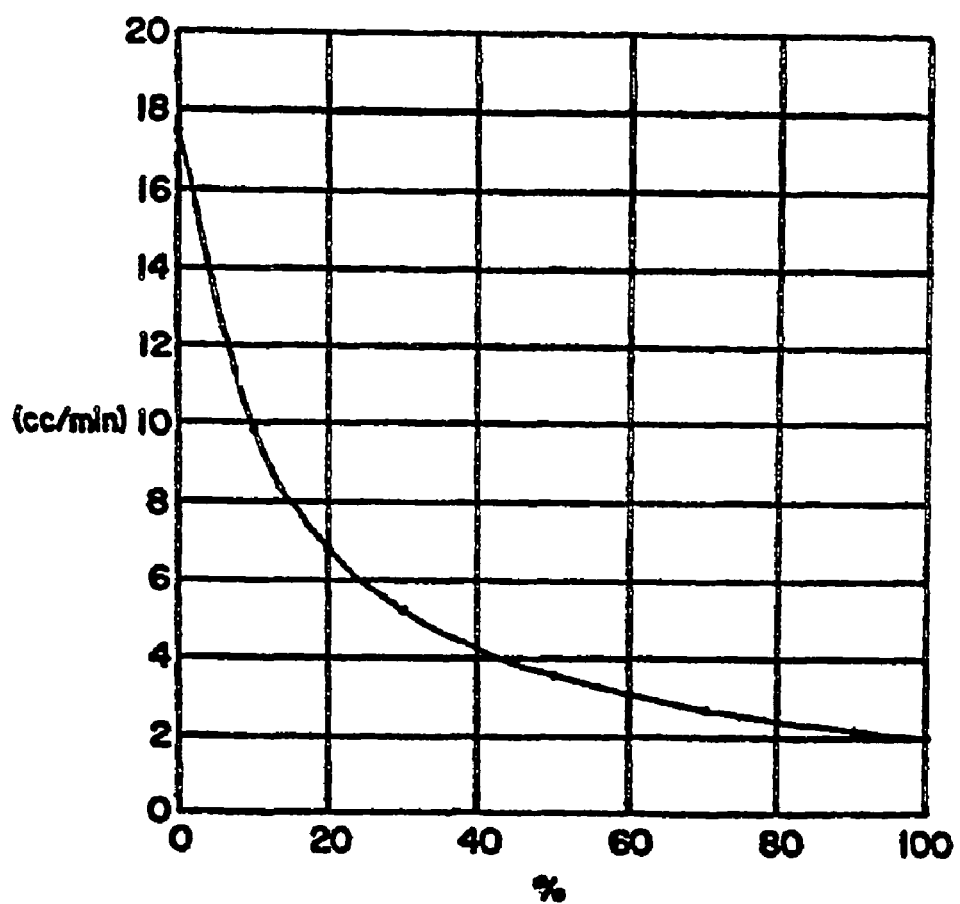
FIG. 5 is a graph that describes a relationship between percentage saline boiling (%) and saline flow rate (Q, in cc/min) for an exemplary RF generator output setting of 75 watts.

FIG. 5 is an exemplary graph of flow rate Q versus % boiling for a situation where the RF power P is 75 watts. The percent boiling % is represented on the X-axis, and the saline flow rate Q (cc/min) is represented on the Y-axis. According to this example, at 100% boiling the most desirable predetermined saline flow rate Q is 2 cc/min. Also according to this example, flow rate Q versus % boiling at the remaining points of the graft illustrates a non-linear relationship as follows:

TABLE 1

| % Boiling and Flow Rate Q (cc/min) at RF Power P of 75 watts | |
|---|---|
| 0% | 17.4 |
| 10% | 9.8 |
| 20% | 6.8 |
| 30% | 5.2 |
| 40% | 4.3 |
| 50% | 3.6 |
| 60% | 3.1 |
| 70% | 2.7 |
| 80% | 2.4 |
| 90% | 2.2 |
| 100% | 2.0 |

Typical RF generators used in the field have a monopolar power selector switch to 300 watts of power, and on occasion some have been found to be selectable up to 400 watts of power. In conformance with the above methodology, at 0% boiling with a corresponding power of 300 watts, the calculated flow rate Q is 69.7 cc/min and with a corresponding power of 400 watts the calculated flow rate Q is 92.9 cc/min. Thus, when used with typical RF generators in the field, a fluid flow rate Q of about 100 cc/min or less with the present invention is expected to suffice for the vast majority of applications.

Figure 6:
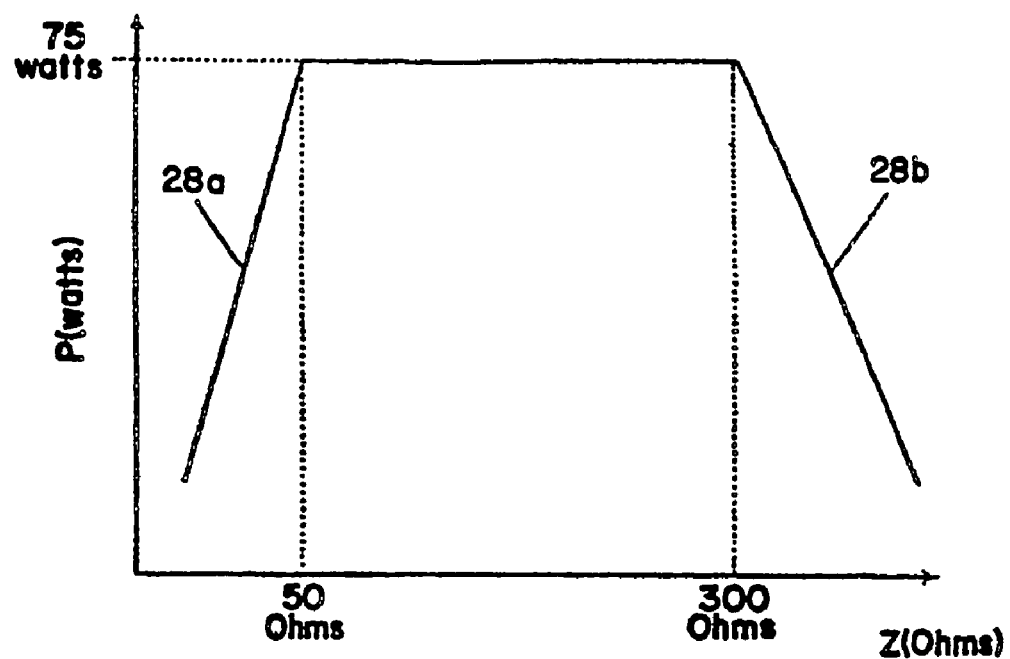
FIG. 6 is a schematic graph that describes a relationship between load impedance (Z, in ohms) and generator output power (P, in watts), for an exemplary RF generator output setting of 75 watts in a bipolar mode.

As discussed herein, RF power delivery to tissue can be unpredictable and vary with time, even though the generator has been "set" to a fixed wattage. The schematic graph of FIG. 6 shows the general trends of the output curve of a typical general-purpose generator, with the output power changing as load impedance Z changes. Load impedance Z (in ohms) is represented on the X-axis, and generator output power P (in watts) is represented on the Y-axis. In the illustrated embodiment, the electrosurgical power (RF) is set to 75 watts in a bipolar mode. As shown in the figure, the power will remain constant as it was set as long as the impedance Z stays between two cut-offs, low and high, of impedance, that is, for example, between 50 ohms and 300 ohms in the illustrated embodiment. Below load impedance Z of 50 ohms, the power P will decrease, as shown by the low impedance ramp 28a. Above load impedance Z of 300 ohms, the power P will decrease, as shown by the high impedance ramp 28b. This change in output is invisible to the user of the generator and not evident when the generator is in use, such as in an operating room.

Figure 7:
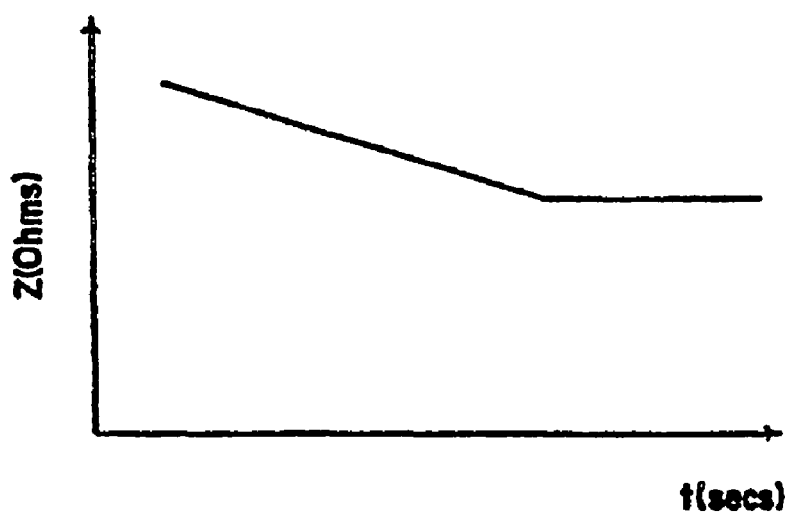
FIG. 7 is a schematic graph that describes a relationship between time (t, in seconds) and tissue impedance (Z, in ohms) after RF activation.

FIG. 7 shows the general trend of how tissue impedance generally changes with time for saline-enhanced electrosurgery. As tissue heats up, the temperature coefficient of the tissue and saline in the cells is such that the tissue impedance decreases until a steady-state temperature is reached upon which time the impedance remains constant. Thus, as tissue heats up, the load impedance Z decreases, potentially approaching the impedance Z cut-off of 50 ohms. If tissue is sufficiently heated, such that the low impedance cut-off is passed, the power P decreases along the lines of the low impedance ramp 28a of FIG. 6.

Combining the effects shown in FIG. 6 and FIG. 7, it becomes clear that when using a general-purpose generator set to a "fixed" power, the actual power delivered can change dramatically over time as tissue heats up and impedance drops. Looking at FIG. 6, if the impedance Z drops from 100 to 75 ohms over time, the power output would not change because the curve is "flat" in that region of impedances. If, however, the impedance Z drops from 75 to 30 ohms one would transgress the low impedance cut-off and "turn the corner" onto the low impedance ramp 28a portion of the curve and the power output would decrease dramatically.

According to one exemplary embodiment of the invention, the control device, such as flow rate controller 11, receives a signal indicating the drop in actual power delivered to the tissue and adjusts the flow rate Q of saline to maintain the tissue/electrode interface at a desired temperature. In a preferred embodiment, the drop in actual power P delivered is sensed by the power measurement device 8 (shown in FIG. 1), and the flow rate Q of saline is decreased by flow rate controller 11 (also shown in FIG. 1). Preferably, this reduction in saline flow rate Q allows the tissue temperature to stay as hot as possible without desiccation. If the control device was not in operation and the flow rate Q allowed to remain higher, the tissue would be over-cooled at the lower power input. This would result in decreasing the temperature of the tissue at the treatment site and lead to longer treatment time.

Flow rate controller 11 of FIG. 1 can include a delay mechanism, such as a timer, to automatically keep the saline flow on for several seconds after the RF is turned off to provide a post-coagulation cooling of the tissue or "quench," which can increase the strength of the tissue seal. Flow rate controller 11 can also include a delay mechanism, such as a timer, to automatically turn on the saline flow several seconds before the RF is turned on to inhibit the possibility of undesirable effects as tissue desiccation, electrode sticking, char formation and smoke production. Optionally, flow rate controller 11 can include a low level flow standby mechanism, such as a valve, which continues the saline flow at a standby flow level (which prevents the flow rate from going to zero when the RF power is turned off) below the surgical flow level ordinarily encountered during use of the electrosurgical device 5.

An exemplary electrosurgical device of the present invention which may be used in conjunction with the system of the present invention is shown at reference character 5a in FIG. 9, and more particularly in FIGS. 9-13. While various electrosurgical devices of the present invention are described with reference to use with the remainder of the system of the invention, it should be understood that the description of the combination is for purposes of illustrating the remainder of the system of the invention only. Consequently, it should be understood that the electrosurgical devices of the present invention can be used alone, or in conjunction with the remainder of the system of the invention, or that a wide variety of electrosurgical devices can be used in connection with the remainder of the system of the invention. The electrosurgical devices disclosed herein are preferably further configured for both open and minimally invasive surgery, such as laparoscopic surgery. For laparoscopic surgery, the devices are preferably configured to fit through either a 5 mm or 12 mm trocar cannula.

Figure 8:
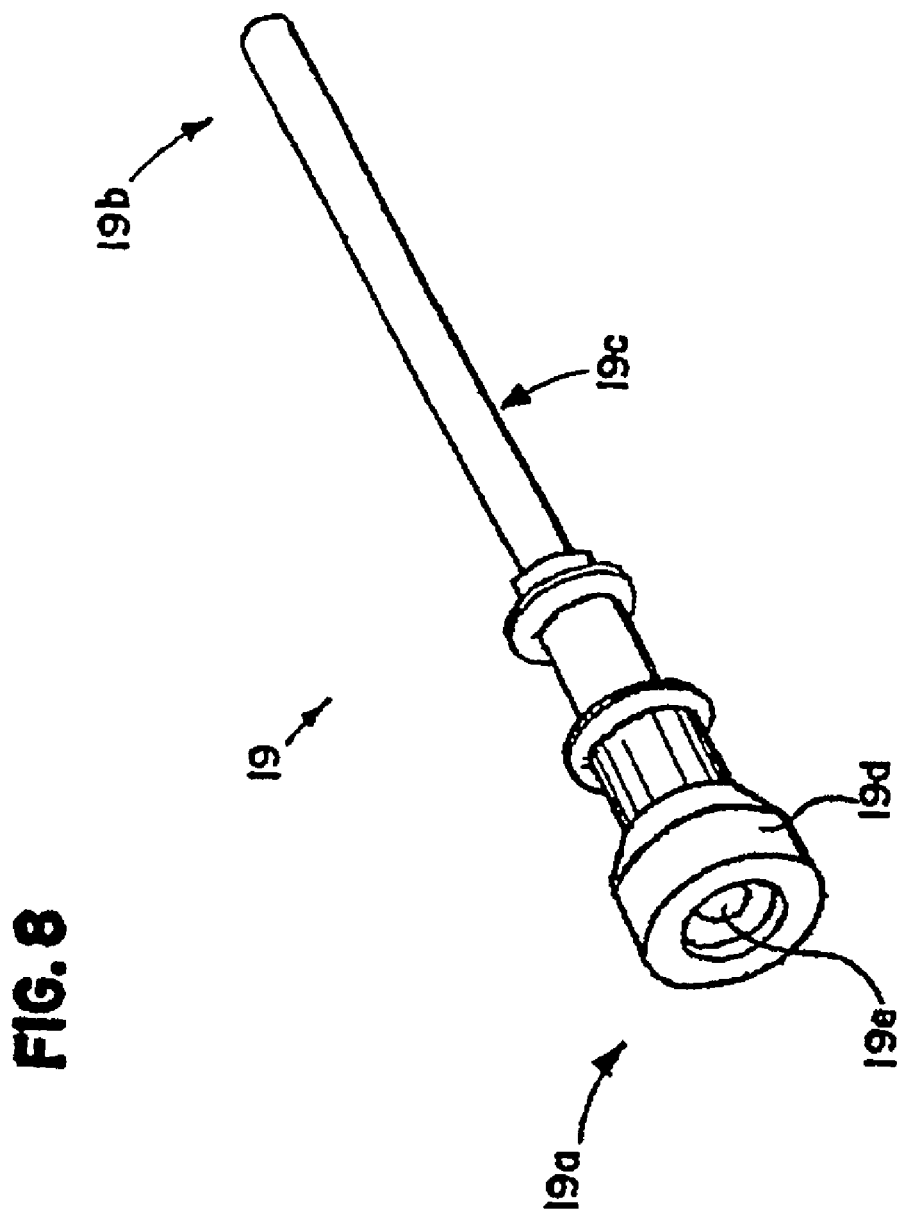
FIG. 8 is a schematic perspective view of a cannula which may be used with an electrosurgical device according to the present invention.

As shown in FIG. 8, electrosurgical device 5a may be used in conjunction with a cannula as illustrated at reference character 19, during laparoscopic surgery such as, for example, a laparoscopic cholecystectomy. Cannula 19 comprises a proximal portion 19a separated from a distal portion 19b by an elongated rigid shaft portion 19c. Proximal portion 19a of cannula 19 preferably comprises a head portion 19d connected to rigid shaft portion 19c, preferably by threaded engagement. Most importantly, cannula 19 has a working channel 19e which extends through head portion 19d and shaft portion 19c from proximal portion 19a to distal portion 19b of cannula 19. In one particular embodiment, during insertion into cannula 19, electrosurgical device 5a is configured to enter the proximal end of working channel 19e, move along the channel 19e distally, and then be extended from the distal end of the working channel 19e. In the same embodiment, during retraction from cannula 19, electrosurgical device 5a is configured to enter the distal end of working channel 19e, move along the channel 19e proximally, and then be removed from the proximal end of working channel 19e.

Figure 11:
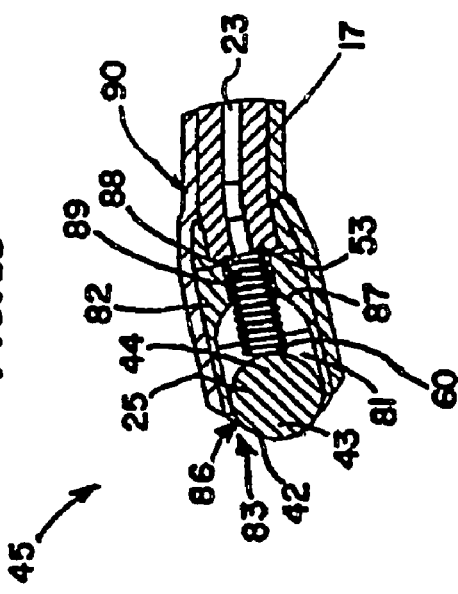
FIG. 11 is a schematic close-up longitudinal cross-sectional side view of the tip portion of the device bounded by circle 45 shown in FIG. 10 taken along line 10-10 of FIG. 12.
Figure 10:
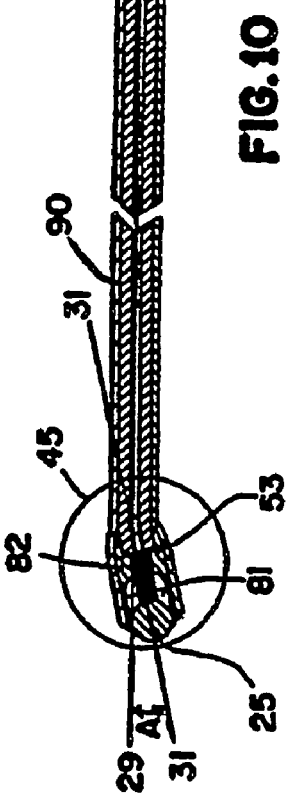
FIG. 10 is a schematic longitudinal cross-sectional side view of the tip and shaft of the device of FIG. 9 taken along line 10-10 of FIG. 12.

Referring back to FIG. 9, as shown electrosurgical device 5a is a monopolar electrosurgical device. Electrosurgical device 5a preferably includes a rigid, self-supporting, hollow shaft 17, a proximal handle comprising mating handle portions 20a, 20b and a tip portion as shown by circle 45. Handle 20a, 20b is preferably made of a sterilizable, rigid, non-conductive material, such as a polymer (e.g., polycarbonate). As shown in FIGS. 10 and 11, tip portion 45 includes a contact element preferably comprising an electrode 25 which, as shown, comprises a solid ball having a smooth, uninterrupted surface. Tip portion 45 also comprises a sleeve 82 having a uniform diameter along its longitudinal length, a spring 88 and a distal portion of shaft 17. As shown in FIG. 10, the longitudinal axis 31 of the tip portion 45 may be configured at an angle A relative to the longitudinal axis 29 of the proximal remainder of shaft 17. Preferably, angle A is about 5 degrees to 90 degrees, and more preferably, angle A is about 8 degrees to 45 degrees.

As shown in FIGS. 10 and 11, for electrosurgical device 5a, electrode 25 generally has a spherical shape with a corresponding spherical surface, a portion 42 of which is exposed to tissue 32 at the distal end of device 5a. When electrode 25 is in the form of a sphere, the sphere may have any suitable diameter. Typically, the sphere has a diameter in the range between and including about 1 mm to about 7 mm, although it has been found that when a sphere is larger than about 4 mm or less than about 2 mm tissue treatment can be adversely effected particularly tissue treatment time) due to an electrode surface that is respectively either to large or to small. Thus, preferably the sphere has a diameter in the range between and including about 2.5 mm to about 3.5 mm, more preferably, about 3 mm.

It is understood that shapes other than a sphere can be used for the contact element. Examples of such shapes include oblong or elongated shapes. However, as shown in FIGS. 10 and 11, preferably a distal end surface of electrosurgical device 5a provides a blunt, rounded surface which is non-pointed and non-sharp as shown by electrode 25.

As shown in FIGS. 10 and 11, electrode 25, is preferably located in a cavity 81 of a cylindrical sleeve 82 providing a receptacle for electrode 25. Among other things, sleeve 82 guides movement of electrode 25. Among other things, sleeve 82 also functions as a housing for retaining electrode 25.

Also as shown in FIG. 11, a portion 44 of electrode 25, is retained within cavity 81 while another portion 43 extends distally through the fluid outlet opening provided by circular fluid exit hole 26. Also as shown, sleeve 82 is connected, preferably via welding with silver solder, to the distal end 53 of shaft 17. For device 5a, electrode 25, sleeve 82 and shaft 17 preferably include, and more preferably are made at least almost essentially of, an electrically conductive metal, which is also preferably non-corrosive. A preferred material is stainless steel. Other suitable metals include titanium, gold, silver and platinum. Shaft 17 preferably is stainless steel hypotubing.

As for cavity 81, the internal diameter of cavity 81 surrounding electrode 25 is preferably slightly larger than the diameter of the sphere, typically by about 0.25 mm. This permits the sphere to freely rotate within cavity 81. Consequently, cavity 81 of sleeve 82 also preferably has a diameter in the range of about 1 mm to about 7 mm.

Figure 12:
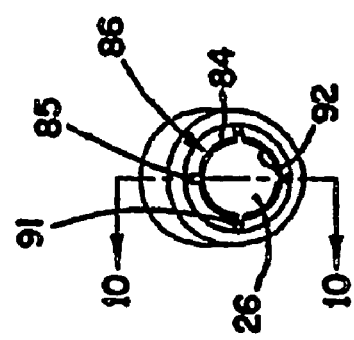
FIG. 12 is a schematic distal end view of the tip portion of the device bounded by circle 45 shown in FIG. 10.

As best shown in FIGS. 11 and 12, in order to retain electrode 25, within the cavity 81 of sleeve 82, preferably the fluid exit hole 26, which ultimately provides a fluid outlet opening, of cavity 81 at its distal end 83 comprises a distal pinched region 86 which is reduced to a size smaller than the diameter of electrode 25, to inhibit escape of electrode 25 from sleeve 82. More preferably, the fluid exit hole 26 has a diameter smaller than the diameter of electrode 25.

As best shown in FIG. 12, fluid exit hole 26 preferably has a diameter smaller than the diameter of electrode 25, which can be accomplished by at least one crimp 84 located at the distal end 83 of sleeve 82 which is directed towards the interior of sleeve 82 and distal to the portion 44 of electrode 25 confined in cavity 81. Where one crimp 84 is employed, crimp 84 may comprise a single continuous circular rim pattern. In this manner, the contact element portion extending distally through the fluid outlet opening (i.e., electrode portion 43) provided by fluid exit hole 26 has a complementary shape to the fluid outlet opening provided by fluid exit hole 26, here both circular.

As shown in FIG. 12, crimp 84 may have a discontinuous circular rim pattern where crimp 84 is interrupted by at least one rectangular hole slot 85 formed at the distal end 83 of sleeve 82. Thus, the fluid outlet opening located at the distal end of the device 5a may comprise a first portion (e.g., the circular fluid exit hole portion 26) and a second portion (e.g., the slot fluid exit hole portion 85). As shown in FIG. 12, preferably, crimp 84 comprises at least four crimp sections forming a circular rim pattern separated by four discrete slots 85 radially located there between at 90 degrees relative to one another and equally positioned around the fluid outlet opening first portion. Slots 85 are preferably used to provide a fluid outlet opening or exit adjacent electrode 25, when electrode 25 is fully seated (as discussed below) and/or when electrode 25 is not in use (i.e., not electrically charged) to keep surface portion 42 of the electrode surface of electrode 25 wet. Preferably, slots 85 have a width in the range between and including about 0.1 mm to 1 mm, and more preferably about 0.2 mm to 0.3 mm. As for length, slots 85 preferably have a length in the range between and including about 0.1 mm to 1 mm, and more preferably bout 0.4 mm to 0.6 mm.

As shown in FIG. 12, the contact element portion extending distally through the fluid outlet opening (i.e., electrode portion 43) extends distally through the fluid outlet opening first portion (e.g., the circular fluid exit hole portion 26) and does not extend distally through the fluid outlet opening second portion (e.g., the slot fluid exit hole portion 85). In this manner an edge 91 of slot 85 remains exposed to tissue 32 to provide a tissue separating edge as discussed below.

It should be understood that the particular geometry of fluid outlet opening provided by the fluid exit hole located at the distal end of device 5a to the electrode is not critical to the invention, and all that is required is the presence of a fluid exit hole which provides fluid 24 as required. For example, fluid exit hole 26 may have an oval shape while electrode 25 has a different shape, such as a round shape.

As shown in FIG. 12, in addition to slot 85 providing a fluid exit, at least one edge 91 of slot 85 may provide a tissue separating edge adjacent a blunt surface (e.g., surface portion 42 of electrode 25) which may be used for blunt dissection when the electrosurgical device 5a is manipulated, particularly by rotating (e.g., twirling), abrading or impacting. When edge 91 is used in such regard, it is preferred that the edge comprise a sharp edge with a sharp angle which has not been rounded by, for example, a fillet.

Turning to the proximal end of the tip (comprising electrode 25, spring 88 and sleeve 82) of the device 5a, as shown in FIG. 11, preferably the portion of sleeve 82 proximal to electrode 25, also has a proximal pinched region 87 which retains electrode 25 in the cavity 81 of sleeve 82 and inhibits escape of electrode 25 from the cavity 81 of sleeve 82, such as a diameter smaller than the diameter of electrode 25.

While distal pinched region 86 and proximal pinched region 87 may be used solely to support electrode 25, in its position of use, the electrode may be further supported by a compression spring 88 as shown in FIG. 11. The use of spring 88 is preferred to provide a variable length support within the working length of the spring 88 for overcoming manufacturing tolerances (e.g., length) between the fixed supports (i.e., pinched regions 86 and 87) of sleeve 82. As for maintaining proper location of the spring 88, sleeve 82 also comprises a lumen 89 as shown in FIG. 11, which, in addition to providing a direct passage for fluid, provides a guide tube for spring 88. Furthermore, the surface portion 60 of electrode 25, which contacts spring 88 may have a flat surface rather than a curvilinear surface to better seat the spring against electrode 25.

In addition to the above, spring 88 provides a multitude of functions and advantages. For example, the configuration of the distal pinched region 86, proximal pinched region 87 and spring 88 offers the ability to move electrode 25 distally and proximally within sleeve 82. As shown in FIG. 11, spring 88 is located proximal to electrode 25 between a first load bearing surface comprising the electrode surface 60 and a second load bearing surface comprising the distal end 53 of shaft 17. In this manner, spring 88 can be configured to provide a decompression force to seat electrode 25 against the distal pinched region 86, in this case the perimeter edge 92 of crimp 84, prior to use of electrosurgical device 5a.

Conversely, upon application of electrode 25 against surface 22 of tissue 32 with sufficient force to overcome the compression force of the spring 88, spring 88 compresses and electrode 25 retracts proximally away from distal pinched region 86, in this case perimeter edge 92 of crimp 84, changing the position thereof. In the above manner, the contact element comprising electrode 25 is retractable into the cavity 81 of the housing provided by sleeve 82 upon the application of a proximally directed force against surface 42 of the portion 43 of electrode 25 extending distally beyond the distal opening 26 located at the distal end 83 of the housing and spring 88 functions as a retraction biasing member.

By making electrode 25 positionable in the above manner via spring 88, electrosurgical device 5a can be provided with a damper mechanism which dampens the force of electrode 25 on tissue 32 being treated.

Furthermore, electrode 25 which can be positioned as outlined above can comprise a fluid flow rate adjustment mechanism which incrementally increases the area of fluid exit hole 26 and the corresponding fluid flow rate in response to the incremental proximal retraction of electrode 25. In such an instance, electrode 25 functions as a valve by regulating flow of fluid 24 through fluid exit hole 26.

In various embodiments, spring 88 may be used in conjunction with the distal pinched region 86 (e.g., crimp 84 comprising a single continuous circular pattern) to provide a fluid seal between electrode 25 and the distal pinched region 86 which stops fluid flow from the electrosurgical device 5a. In this manner, the electrosurgical device 5a may be used to provide both a wet electrode and dry electrode (i.e., when the fluid flow is on and off, respectively) with the energy and fluid provided sequentially as opposed to simultaneously.

Furthermore, in various embodiments of electrosurgical device 5a, an electrode 25 which can be positioned as outlined above can include a declogging mechanism. Such a mechanism can retract to provide access for unclogging fluid exit holes (e.g., 26 and 85), which may become flow restricted as a result of loose debris (e.g., tissue, blood, coagula) becoming lodged therein. For example, when a biasing force, such as from a handheld cleaning device (e.g., brush) or from pushing the distal tip against a hard surface such as a retractor, is applied to surface 42 of electrode 25 which overcomes the compression force of the spring 88 causing the spring 88 to compress and electrode 25 to retract, the tip of the handheld cleaning device may by extended into the fluid exit hole 26 for cleaning the fluid exit hole 26, perimeter edge 92, slot 85 and edge 91. Stated another way, electrode 25, which can be positioned as outlined, provides a methodology for declogging a fluid exit hole by increasing the cross-sectional area of the fluid exit hole to provide access thereto.

Additionally, in various embodiments of device 5a, spring 88 comprises an electrical conductor, particularly when electrode 25, is retracted to a non-contact position (i.e., not in contact) with sleeve 82.

In other embodiments, proximal pinched region 87 may comprise one or more crimps similar to distal pinched region 86, such that electrode 25 is retained in sleeve 82 both distally and proximally by the crimps. Also, in other embodiments, sleeve 82 may be disposed within shaft 17 rather than being connected to the distal end 53 of shaft 17. Also, in still other embodiments, sleeve 82 may be formed unitarily (i.e., as a single piece or unit) with shaft 17 as a unitary piece.

As best shown in FIGS. 10 and 11, electrode 25 is retained in sleeve 82 with a portion 43 of electrode 25 extending distally beyond distal end 83 of sleeve 82. As shown, preferably the surface 42 of this exposed portion 43 of electrode 25 is blunt and does not have any sharp corners. Also, the portion 43 of electrode 25 which extends distally beyond the distal end 83 of sleeve 82 is controlled by the shape of the fluid exit hole 26 in sleeve 82 in relation to the shape of electrode 25. In other words, the portion 43 of electrode 25 that extends distally beyond distal end 83 of sleeve 82 is controlled by the contact of the electrode surface with the edge 92.

In locations where shaft 17 and sleeve 82 are electrically conductive (for device 5a, preferably shaft 17 and sleeve 82 are completely electrically conductive and do not comprise non-conductive portions) an electrical insulator 90 (i.e., comprising non-conductive or insulating material) preferably surrounds shaft 17 and sleeve 82 along substantially its entire exposed length (e.g., the portion outside the confines of the handle 20), terminating a short distance (e.g., at the proximal onset of crimp 84 or less than about 3 mm) from distal end 83 of sleeve 82. Insulator 90 preferably comprises a shrink wrap polymer tubing.

As with the other electrosurgical devices described within, a input fluid line 4b and a power source, preferably comprising generator 6 preferably providing RF power via cable 9, are preferably fluidly and electrically coupled, respectively, to the tip portion 45 of the electrosurgical device 5a.

As indicated above, device 5a comprises a monopolar device. For electrosurgical device 5a, electrode 25 provides an active electrode, while a ground pad dispersive electrode 125 (shown in FIG. 45) located on the patient, typically on the back or other suitable anatomical location, provides a return electrode. Preferably, both electrodes are electrically coupled to generator 6 to form an isolated electrical circuit. Preferably the active electrode is coupled to generator 6 via a wire conductor from insulated wire cable 9 to the outer surface 18 of shaft 17 within the confines of handle 20a, 20b, typically through a switch such as 15a.

Switch 15a preferably comprises a dome switch having two electrical contacts. The contacts preferably comprise upper and lower contacts disposed on a platform in overlying relationship. Preferably the upper contact comprises a dome shaped configuration overlying and spaced from the lower contact which is flat. Preferably the contacts are spaced from one another by virtue of the domed configuration of the upper contact when the switch 15a is in an undepressed position, thus creating an open control circuit relative to switch 15a. However, when the upper contact is pressed into a depressed position, the upper contact comes into contact with the lower contact thus closing the hand switch control circuit. The presence of the closed control circuit is then sensed by generator 6 which then provides power to the electrode 25.

When a depression force is removed from the upper contact, the contact returns to its undepressed domed position as a result of its resiliency or elastic memory, thus returning switch 15a to its undepressed position and reopening the hand control circuit. The presence of the open control circuit is then sensed by the generator which then stops providing power to electrode 25.

In some embodiments, shaft 17 may be made of an electrical non-conducting material except for a portion at its distal end 53 that comes in contact with sleeve 82. This portion of shaft 17 that contacts sleeve 82 should be electrically conducting. In this embodiment, the wire conductor from insulated wire cable 9 extends to this electrically conducting portion of shaft 17. In still other embodiments, shaft 17 may completely comprise a non-conducting material as where the wire conductor from insulated wire cable 9 extends directly to sleeve 82.

With respect to the fluid coupling, fluid 24 from the fluid source 1 preferably is communicated from fluid source 1 through a flexible, polyvinylchloride (PVC) outlet fluid line 4a to a flexible, polyvinylchloride (PVC) inlet fluid line 4b connected to electrosurgical device 5a. Outlet fluid line 4a and inlet fluid line 4b are preferably connected via a male and female mechanical fastener configuration; a preferred such connection is a Luer-Lok® connection from Becton, Dickinson and Company. The lumen of the inlet line is then preferably interference fit over the outside diameter of shaft 17 to provide a press fit seal there between. An adhesive may be used there between to strengthen the seal. Fluid 24 is then communicated down lumen 23 of shaft 17 through lumen 89 and cavity 81 of sleeve 82 where it is expelled from around and on the exposed surface 42 of electrode 25. This provides a wet electrode for performing electrosurgery.

Figure 13:
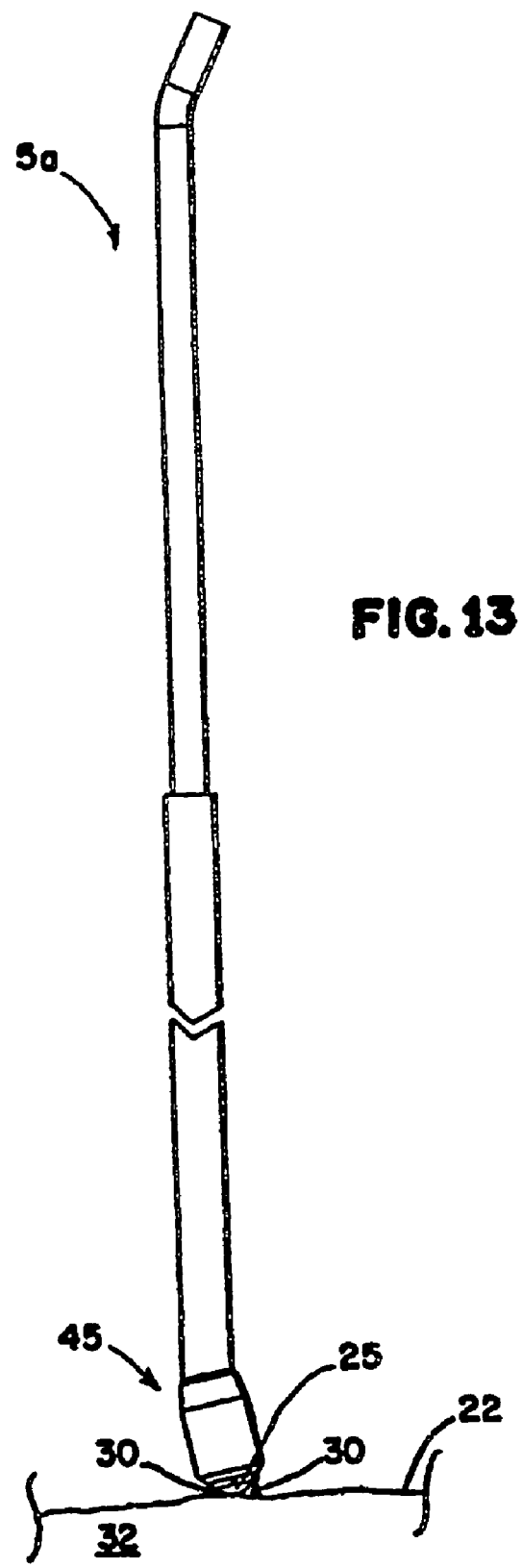
FIG. 13 is a schematic side view of the of the tip and shaft of the device of FIG. 9 with a fluid coupling to a tissue surface of tissue.

As shown in FIG. 13, during use of electrosurgical device 5a, typically a fluid coupling 30 preferably comprising a discrete, localized web and more preferably comprising a triangular shaped web or bead portion providing a film of fluid 24 is provided between surface 22 of tissue 32 and electrode 25. When the user of electrosurgical device 5a places electrode 25 at a tissue treatment site and moves electrode 25 across the surface 22 of the tissue 32, fluid 24 is expelled around and on surface 42 of electrode 25 at the distal end 83 of sleeve 82 and onto the surface 22 of the tissue 32 via coupling 30. The fluid 24, in addition to providing an electrical coupling between electrosurgical device 5a and tissue 32, lubricates surface 22 of tissue 32 and facilitates the movement of electrode 25 across surface 22 of tissue 32. During movement of electrode 25, electrode 25 typically slides across surface 22 of tissue 32, but also may rotate as electrode 25 moves across surface 22 of tissue 32. Typically the user of the electrosurgical device 5a slides the electrode across surface 22 of tissue 32 back and forth with a painting motion while using fluid 24 as, among other things, a lubricating coating. Preferably the thickness of the fluid 24 between the distal end surface of electrode 25 and surface 22 of tissue 32 at the outer edge of the coupling 30 is in the range between and including about 0.05 mm to 1.5 mm, more preferably in the range between and including about 0.1 mm to 0.3 mm. Also preferably, in certain embodiments, the distal end tip of electrode 25 contacts surface 22 of tissue 32 without any fluid 24 in between.

Figure 15:
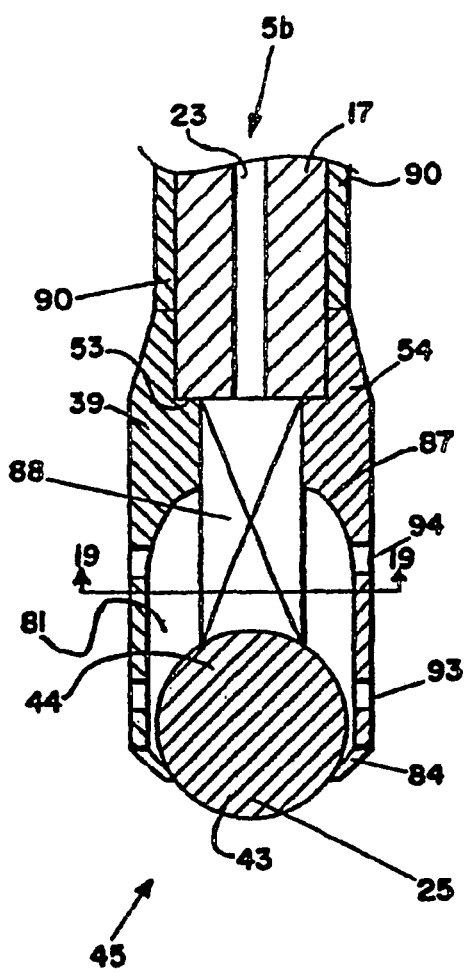
FIG. 15 is a schematic close-up cross-sectional side view of the tip portion of FIG. 14 taken along line 15-15 of FIG. 14.
Figure 14:
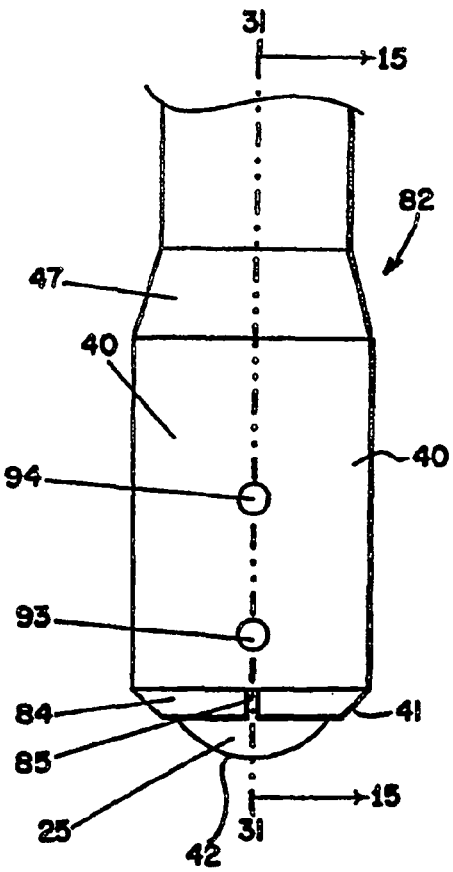
FIG. 14 is a schematic close-up side view of an alternative tip portion.
Figure 16:
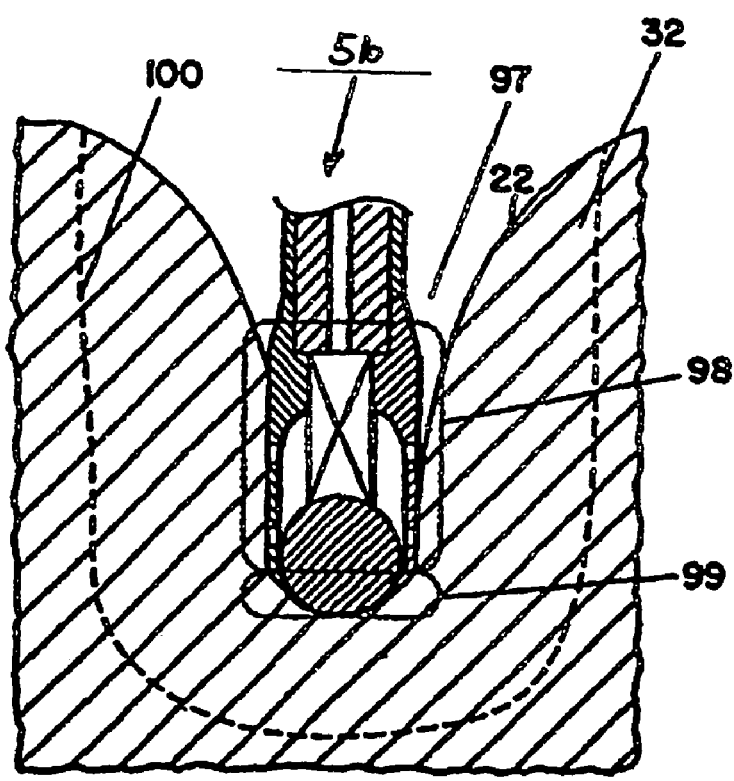
FIG. 16 is a schematic close-up cross-sectional side view of the tip portion of FIG. 14 disposed in a tissue crevice.

Another exemplary electrosurgical device is shown at reference character 5b in FIGS. 14-16. In this embodiment, electrical insulator 90 preferably terminates proximally to sleeve 82 where sleeve 82 is connected to the distal end 53 of shaft 17. In certain embodiments where sleeve 82 is formed unitary shaft 17, electrical insulator 90 preferably terminates proximally to proximal pinched region 87. In this manner, in addition to the spherical surface portion 42 of electrode 25 and the narrowing surface portion 41, here conical, of sleeve 82 being used for treating tissue 32 when exposed thereto, a cylindrical surface 40 of a cylindrical portion 39 of sleeve 82 and a broadening surface portion 47 of broadening portion 54, here both conical, of sleeve 82 also function as electrode surfaces for treating tissue. Thus, the electrode exposed to tissue 32 now comprises a cylindrical surface portion 40 and a broadening surface portion 47 in addition to the spherical surface portion 42 and the narrowing surface portion 41, with the cylindrical surface portion 40 substantially increasing the surface area of the electrode. As a result, electrode 25 has surfaces which are parallel and perpendicular to the longitudinal axis 31 of tip portion 45, and more particularly, sleeve 82 of electrosurgical device 5b. In the above manner, front end use (e.g., surfaces 41 and 42), sideways use (e.g., surface 40 and 47), or oblique use (e.g., surfaces 40, 41 and 42) of electrosurgical device 5b is facilitated.

In the above manner, tip portion 45 now includes a first tissue treating surface (e.g., distal end spherical surface 42) and a second tissue treating surface (e.g., side surface 40). As discussed above, preferably the first tissue treating surface is configured for blunt dissection while the second tissue treating surface is configured for coagulation. Additionally, tip portion 45 also has a third tissue treating surface (e.g., surface 41) located between the first tissue treating surface (e.g., surface 42) and a second tissue treating surface (e.g., surface 40). Furthermore, tip portion 45 also has a fourth tissue treating surface (e.g., surface 47) located proximal and adjacent to surface 40.

With device 5a, when electrode 25 is placed directly in contact with surface 22 of tissue 32, tissue 32 may occlude fluid flow from fluid exit holes 26, 85 located at the distal end of device 5a. Consequently, for device 5b fluid exit holes 93, 94 may be located in the cylindrical side portion 39 of sleeve 82, either proximal or adjacent to electrode 25, and either in addition to or as an alternative to fluid exit holes 26, 85.

As shown in FIGS. 14 and 15, at least one fluid exit hole 93 is preferably formed in the cylindrical longitudinal side surface 40 and through the wall of side portion 39 of sleeve 82 adjacent to electrode 25 when electrode 25 is fully seated. Furthermore, preferably at least one fluid exit hole 94 is formed in the cylindrical side portion 39 of sleeve 82 proximal to electrode 25 when electrode 25 is fully seated.

Preferably, holes 93, 94 each comprise more than one hole which are equally spaced radially in a circular pattern around the longitudinal axis 31 of tip portion 45, and more particularly sleeve 82. More preferably, holes 93, 94 each comprise four discrete holes equally spaced 90 degrees around the cylindrical side portion 39 of sleeve 82. Preferably holes 93, 94 have a diameter in the range between and including about 0.1 mm to 1.0 mm, and more preferably have a length in the range between and including about 0.2 mm to 0.6 mm.

Electrode 25, which can be positioned as outlined above, can comprise not only a valve for regulating fluid flow from the fluid exit holes, such as fluid exit hole 26, but also comprise a valve which, while opening one fluid flow exit, simultaneously closes another fluid flow exit. For example, as electrode 25 retracts proximally, fluid exit hole 26 is opened while fluid exit hole 93 is closed. Stated another way, an electrode 25 which can be positioned as outlined above can provide a mechanism for altering the size and/or location of the fluid exit holes during use of electrosurgical device 5b which may be necessary, for example, to direct fluid to a particular tissue location or balance fluid flow among the fluid exit outlets.

Thus, as shown in FIGS. 14 and 15, surfaces 40, 41 and 47 of sleeve 82, and surface 42 of electrode 25 are all active electrode surfaces and can provide electrical energy to tissue 32. Portions of this combined electrode surface can be wet by fluid flow from holes 26, 94 or 93, as well as from the hole slots 85 in crimp 84 adjacent electrode 25.

The holes 94, 93 in the cylindrical sleeve 82 of the overall electrode surface are intended to assure that fluid 24 is provided to the smooth, less rough, atraumatic sides of the electrode that may be predominately used for tissue coagulation and hemostasis (e.g., surfaces 40 and 47) rather than blunt dissection (e.g., surfaces 41 and 42). The most distal portion of the device may have a more rough, but also wetted, electrode surface that can blunt dissect as well as coagulate tissue.

The electrode configuration shown in FIGS. 14 and 15 is particularly useful to a surgeon performing a liver resection. Once the outer capsule of the liver is scored with a dry bovie blade along the planned line of resection the distal tip of tip portion 45 is painted back and forth along the line, resulting in coagulation of the liver parenchyma beneath the scored capsule. As the tissue is coagulated under and around the electrode surfaces 40, 41 and 42, the electrode is used to blunt dissect into the coagulated parenchyma, with edge 91 of slots 85 around crimp 84 providing roughness elements that aid in disrupting the tissue 32 and enabling the parting of tissue 32.

As shown in FIG. 16, the device 5b can be used in a crevice 97 of tissue 32 to blunt dissect tissue 32 and coagulate it at the same time. Blunt dissection is preferred over sharp dissection, such as with a blade or scissors, since blunt dissection is less likely to tear or damage the larger blood vessels or other vessels. Once identified by blunt dissection, very large vessels can be safely clipped, tied with suture or sealed with some other device. If the larger vessels are not thus first "skeletonized" without being damaged by blunt dissection, they may bleed profusely and require much more time to stop the bleeding. The device can also be used to coagulate first without simultaneous blunt dissection, and then blunt dissect in a separate step.

This technique can also be used on other parenchymal organs such as the pancreas, the kidney, and the lung. In addition, it may also be useful on muscle tissue and subcutaneous fat. It's use can also extend to benign tumors, cysts or other tissue masses found in the urological or gynecological areas. It would also enable the removal of highly vascularized tumors such as hemangiomas.

In FIG. 16 the zone 99 identifies the part of the electrode that has the ability to blunt dissect and coagulate, and the zone 98 identifies the part that is intended primarily for coagulation and hemostasis. The line 100 indicates the depth of the zone of tissue that is coagulated, typically from 3 mm to 5 mm deep.

Figure 17:
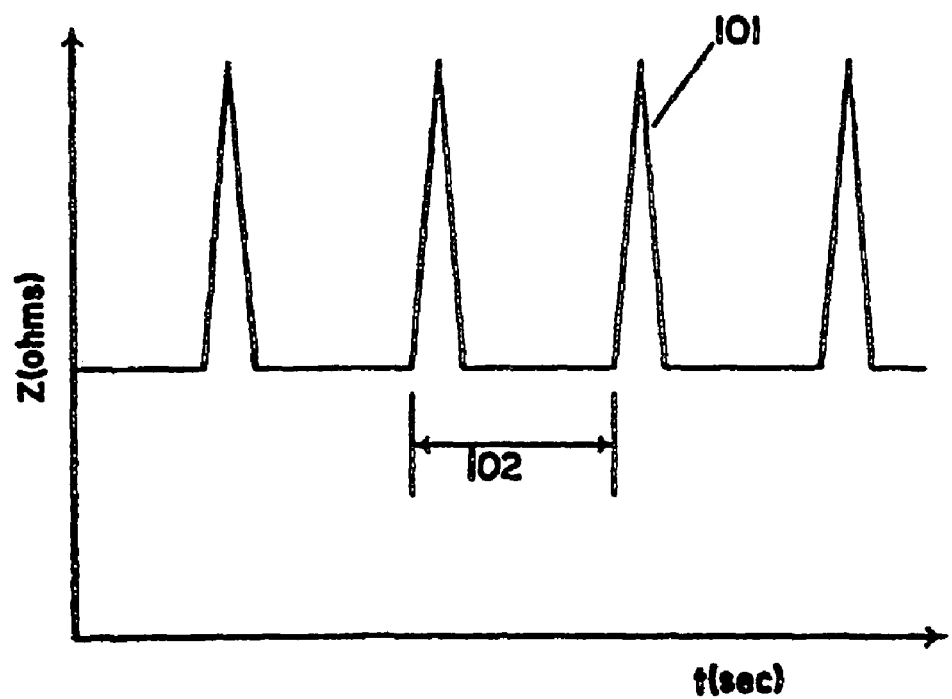
FIG. 17 is a schematic graph that describes a relationship between time (t, in seconds) and changes in impedance (Z, in ohms) represented by impedance spikes.

For the devices disclosed herein, the presence of various fractions of boiling can be visually estimated by the naked eye, or by detecting changes in electrical impedance. FIG. 17 shows a graph of electrical impedance Z versus time t. The impedance spikes 101 shown in FIG. 17 occur at a frequency of about 1 cycle per second and with an amplitude that is on the same order as the baseline impedance. This frequency is shown in FIG. 17 as the interval 102 between successive impedance spikes. Impedance is directly measurable by dividing the voltage by the current as previously described. The use of electrical impedance to detect the onset of tissue dessication when impedance rises dramatically as a result of being heated to the point of smoking and charring, but not to detect the presence of boiling, is described above.

Shown in FIG. 18 is the qualitative nature of the boiling as the % boiling increases, indicated by the small figures for each of five exemplary "regimes" of boiling. In each small figure a portion of the tip of the tip portion 45 of device 5a is shown in close proximity to tissue 32. As boiling begins in regime 104, there are few small bubbles 37 of vapor in the conductive fluid 24, here saline, of coupling 30. As the percentage of boiling increases at regime 106 there are a larger number of small bubbles 37. As the percentage boiling increases further at regime 107, the bubbles 37 become much larger. At even higher percentage boiling at regime 108 intermittent threads of saline form and are quickly boiled off. Finally, at the highest level of regime 109, drops 36 of saline are instantly boiled upon contacting the hot surface 22 of tissue 32 and arcing occurs from the metal to tissue 32.

Returning to FIGS. 14 and 15, fluid outlet openings are provided by substantially linear through holes 93, 94 which provide conductive fluid 24 to the treatment site. However, in an alternative embodiment, as shown in FIG. 19, fluid outlet openings in sleeve 82 may be provided by holes in the form of tortuous and interconnected pathways 59, which are formed in a material pervious to the passage of fluid 24, therethrough, such as a porous material. The discrete, linear through holes 93, 94 may be either supplemented with or replaced by a plurality of tortuous, interconnected pathways 59 formed in the porous material which, among other things, provides porous surfaces 40, 41 and 47 to more evenly distribute fluid flow and provide the conductive fluid 24 to tissue 32 at the treatment site. According to the invention, all or a portion of sleeve 82 may comprise a material pervious to the passage of fluid 24 therethrough as disclosed herein.

In certain embodiments, the contact element, here electrode 25 may also comprise a material pervious to the passage of fluid 24, therethrough, such as a porous material (e.g., metal, polymer or ceramic) to provide the tortuous pathways 59. In these embodiments, the porous structure of electrode 25 allows fluid 24 to not only pass around electrode 25 on the outer porous surface 42 to be expelled, but also allows fluid 24 to pass through electrode 25, to be expelled. According to the invention, all or a portion of the electrodes or any particular electrodes for treating tissue 32 may comprise a material pervious to the passage of fluid 24 therethrough as disclosed herein.

Where the contact element and sleeve provide electrodes for treating tissue and compromise a porous material, preferably the porous material further comprises porous metal. Porous sintered metal is available in many materials (such as, for example, 316L stainless steel, titanium, Ni-Chrome) and shapes (such as cylinders, discs, plugs) from companies such as Porvair, located in Henderson, N.C.

While the electrode provided by contact element and/or sleeve preferably comprises an electrically conductive material such as metal, a non-electrically conductive porous contact element and/or sleeve, such as porous polymers and ceramics, can be used to replace an electrically conductive contact element and/or sleeve. While the porous polymers and ceramics are generally non-conductive, they may also be used to conduct the RF energy through the porous polymer and ceramic thickness and porous surface to the tissue to be treated by virtue of conductive fluid 24 contained within the plurality of interconnected tortuous pathways 59.

Preferably the porous material provides for the wicking (i.e., drawing in of fluid by capillary action or capillarity) of the fluid 24 into the pores of the porous material. In order to promote wicking of the fluid 24 into the pores of the porous material, preferably the porous material, and in particular the surface of the tortuous pathways, is hydrophilic. The porous material may be hydrophilic with or without post treating (e.g., plasma surface treatment such as hypercleaning, etching or micro-roughening, plasma surface modification of the molecular structure, surface chemical activation or crosslinking), or made hydrophilic by a coating provided thereto, such as a surfactant.

Though not preferable, it is not necessary that fluid coupling 30 of fluid 24 be present in between the metal electrode surfaces (e.g., 40, 41, 42) and tissue 32 at all locations of tissue treatment and there may be points of direct tissue contact by the electrode surfaces without any fluid coupling 30 therebetween. In such an instance, the convective cooling of the metal electrode by flowing saline is often sufficient to keep the metal electrode and tissue contacting the metal electrode at or below a temperature of 100° C. In other words, heat may be also first dissipated from tissue 32 to the electrodes by conduction, then dissipated from the electrodes to the fluid 24 by convection.

Preferably the relationship between the material for electrodes particularly their surfaces (e.g., 40, 41, 42, 47), and fluid 24 throughout the various embodiments should be such that the fluid 24 wets the surface of the electrodes to form a continuous thin film coating thereon (for example, see FIG. 21) and does not form isolated rivulets or circular beads (e.g., with a contact angle, θ greater than 90 degrees) which freely run off the surface of the electrode. Contact angle, θ, is a quantitative measure of the wetting of a solid by a liquid. It is defined geometrically as the angle formed by a liquid at the three phase boundary where a liquid, gas and solid intersect. In terms of the thermodynamics of the materials involved, contact angle θ involves the interfacial free energies between the three phases given by the equation $\gamma_{LV} \cos \theta = \gamma_{SV} - \gamma_{SL}$ where $\gamma_{LV}$, $\gamma_{SV}$ and $\gamma_{SL}$ refer to the interfacial energies of the liquid/vapor, solid/vapor and solid/liquid interfaces, respectively. If the contact angle θ is less than 90 degrees the liquid is said to wet the solid. If the contact angle is greater than 90 degrees the liquid is non-wetting. A zero contact angle θ represents complete wetting. Thus, preferably the contact angle is less than 90 degrees.

For clarification, while it is known that the contact angle θ may be defined by the preceding equation, in reality contact angle θ is determined by a various models to an approximation. According to publication entitled "Surface Energy Calculations" (dated Sep. 13, 2001) from First Ten Angstroms (465 Dinwiddie Street, Portsmouth, Va. 23704), there are five models which are widely used to approximate contact angle θ and a number of others which have small followings. The five predominate models and their synonyms are: (1) Zisman critical wetting tension; (2) Girifalco, Good, Fowkes, Young combining rule; (3) Owens, Wendt geometric mean; (4) Wu harmonic mean; and (5) Lewis acid/base theory. Also according to the First Ten Angstroms publication, for well-known, well characterized surfaces, there can be a 25% difference in the answers provided for the contact angle θ by the models. Also for clarification, any one of the five predominate models above which calculates a contact angle θ within a particular range of contact angles θ or the contact angle θ required of a particular embodiment of the invention should be considered as fulfilling the requirements of the embodiment, even if the remaining four models calculate a contact angle θ which does not fulfill the requirements of the embodiment.

The effects of gravity and surface tension tend to wick the fluid 24, here saline, around the circumference of the cylindrical sleeve 82 to preferably cover the entire active electrode surface. More specifically, the effects of gravity and surface tension on fluid 24 which is located on the electrode surfaces may be modeled by the Bond number $N_{BO}$. Bond number $N_{BO}$ measures the relationship of gravitational forces to surface tension forces and may be expressed as:

$$N_{BO} = \rho L^2 g / \sigma \quad (7)$$

where:
ρ=Density of the saline fluid (approximately 1.0 gm/cm$^3$);
L=Droplet diameter (cm);
g=Gravitational acceleration (980 cm/s$^2$); and
σ=Surface tension (approximately 72.8 dynes/cm@20° C.)

For a Bond number $N_{BO}$=1, the droplet diameter is equal to about 0.273 cm or about 2.7 mm, which is in the same order of magnitude as the preferred size of the electrode. For the purposes of the present invention, preferably Bond number $N_{BO}$ for a droplet of fluid 24 on a surface of electrode 25 is preferably less than 1.

Another tip portion of an exemplary electrosurgical device 5c of the present invention which may be used in conjunction with the system of the present invention is shown at reference character 45 in FIGS. 20-24. As best shown in FIGS. 20 and 21, the separate sleeve 82 of embodiments 5a and 5b has been eliminated from tip portion 45 of device 5c. Consequently, the contact element, still preferably comprising an electrode 25, is assembled directly with the shaft 17. Electrode 25 is preferably assembled (e.g., mechanically connected via press fit, mechanical connector, threaded, welded, adhesively bonded) adjacent the distal end 53 of shaft 17. In certain embodiments, electrode 25 preferably is detachably assembled to the shaft 17 such that it may be removed from the shaft 17, preferably manually by human hand, so that the shaft 17 may be used with multiple different contact elements/electrodes, or the shaft 17 may be reuseable and used with disposable contact elements/electrodes.

As shown in FIGS. 20-24, electrode 25 preferably comprises an enlarged head portion comprising a spherical portion 43 and a corresponding spherical surface portion 42 located at the distal end of the device 5c which provide a smooth, blunt contour outer surface. More specifically, as shown, the spherical portion 43 and spherical surface portion 42 further provide a domed, hemisphere (i.e., less than a full sphere) and hemispherical surface portion comprising preferably about 180 degrees.

Also as shown in FIGS. 20-24, the enlarged head portion of electrode 25 preferably also comprises a cylindrical portion 39 and a corresponding cylindrical surface portion 40 located proximal and adjacent to the spherical portion 43 and spherical surface portion 42, respectively.

Further continuing with FIGS. 20-24, electrode 25 preferably comprises a connector portion, preferably comprising a shank 46, which connects the remainder of electrode 25 to the shaft 17. Among other things, the connector portion of electrode 25 is preferably configured to form a connection with a mating connector portion of the shaft 17. As shown, preferably the shank portion 46 is configured to extend into cavity 50 of shaft 17 which comprises a cylindrical receptacle and provides the mating connector portion for shank 46. More preferably, surface 48 of the shank portion 46 is configured to mate against and form an interference fit with surface 52 of cavity 50 to provide the connection.

Continuing with FIGS. 20-24, shank portion 46 is preferably cylindrical and located proximal and adjacent to a neck portion 56. As shown, neck portion 56 comprises a cylindrical portion 57 (having a corresponding cylindrical surface portion 58) and a broadening portion 54 (having a corresponding broadening surface portion 47). Here broadening portion 54 and corresponding broadening surface portion 47 are both spherical, and more specifically comprise a domed, hemisphere and hemispherical surface portion comprising preferably about 180 degrees, located proximal and adjacent to the cylindrical portion 39 and cylindrical surface portion 40.

Preferably, cylindrical portion 39 has a diameter in the range between and including about 1 mm to about 7 mm, although it has been found that when cylindrical portion 39 is larger than about 4 mm or less than about 2 mm, tissue treatment can be adversely effected (particularly tissue treatment time) due to an electrode surface that is respectively either to large or to small. Thus, preferably the cylindrical portion 39 has a diameter in the range between and including about 2.5 mm to about 3.5 mm, and more preferably, about 3 mm.

With respect to length, preferably cylindrical portion 39 has a length in the range between and including about 2 mm to about 8 mm, and more preferably has a length in the range between and including about 3 mm to about 5 mm. Even more preferably, cylindrical portion 39 has a length of about 4.5 mm.

As shown in FIGS. 20-24, the cylindrical portion 57 of neck portion 56 preferably has a cross-sectional dimension, here diameter, greater than the cross-sectional dimension, here also diameter, of the shank 46. In this manner, in certain embodiments, the proximal end of the neck portion 56 may be located adjacent and in contact with the distal end 53 of shaft 17. Preferably, cylindrical portion 57 has a diameter in the range between and including about 2 mm to about 2.5 mm and the shank 46 has a diameter in the range between and including about 1.4 mm to about 1.9 mm. More preferably, cylindrical portion 57 has a diameter of about 2.2 mm and the shank 46 has a diameter of about 1.6 mm.

With respect to length, preferably cylindrical portion 57 has a length in the range between and including about 1 mm to about 8 mm, and more preferably has a length in the range between and including about 3 mm to about 5 mm. Even more preferably, cylindrical portion 57 has a length of about 4 mm. Shank 46 preferably has a length in the range between and including about 2 mm to about 6 mm, and more preferably has a length in the range between and including about 2.5 mm to about 5 mm. Even more preferably, shank 46 has a length of about 3 mm.

Also as shown in FIGS. 20-24, electrode 25 comprises at least one recess 64 which provides an elongated fluid flow channel for the distribution of fluid 24. The use of device 5c, and in particular recesses 64, for the distribution of fluid 24 is generally preferred to the fluid exit holes 93, 94 of device 5b in particularly deep tissue crevices 97.

Figure 24:
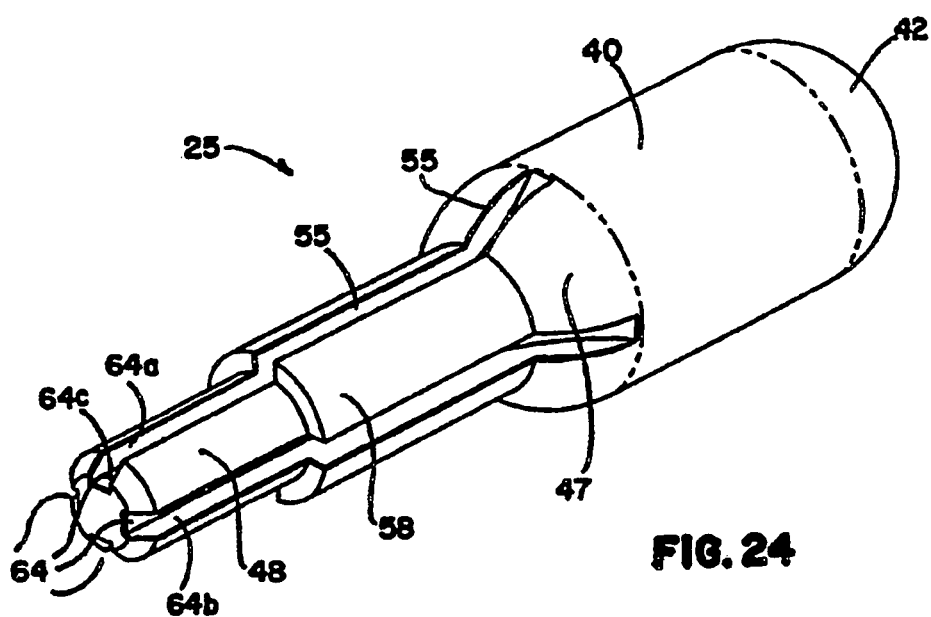
FIG. 24 is a schematic close-up rear perspective view of the electrode for the tip portion of FIG. 20.

As shown, electrode 25 preferably comprises a plurality of longitudinally directed recesses 64 and, more specifically, four recesses 64 equally spaced 90 degrees around the shank 46 and/or neck portion 56, both proximal of cylindrical portion 39. As best shown in FIG. 24, in certain embodiments, the recess 64 may comprise a first side wall 64a, a second opposing side wall 64b, and a bottom wall 64c. Preferably, recess 64 has a width in the range between and including about 0.1 mm to about 0.6 mm, and more preferably has a width of about 0.4 mm.

In use, when tissue 32 overlies and occludes the fluid outlet opening 55 of recess 64 for a portion of its longitudinal length, thus inhibiting fluid 24 from exiting therefrom, fluid 24 from recess 64 may still be expelled from the electrosurgical device 5c after flowing longitudinally in the channel 64 to a remote location where the channel 64 is unoccluded and uninhibited to fluid flow exiting therefrom.

On very rare occasion, it may be possible that the recess 64 may be occluded by tissue 32 completely along its longitudinal length, thus completely inhibiting fluid flow from exiting through opening 55. In order to overcome this problem, at least a portion of electrode 25 may comprise a material pervious to the passage of fluid 24, therethrough, such as a porous material described above.

Figure 22:
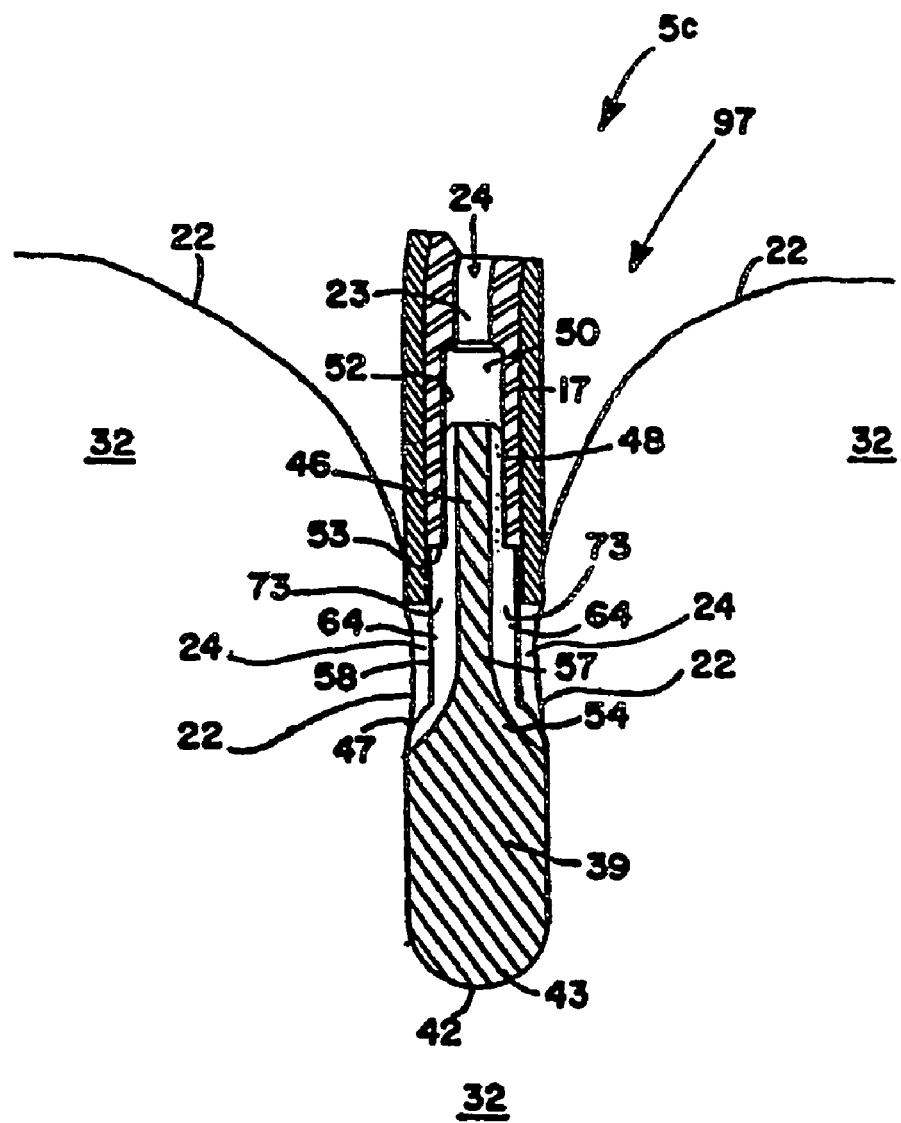
FIG. 22 is a schematic close-up cross-sectional side view of the tip portion of FIG. 20 disposed in a tissue crevice.
Figure 23:
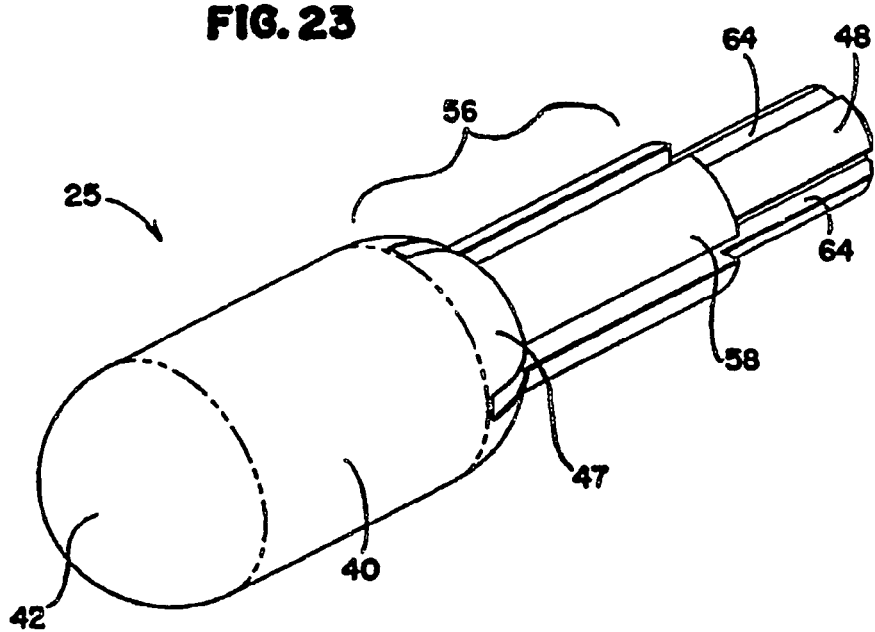
FIG. 23 is a schematic close-up front perspective view of the electrode for the tip portion of FIG. 20.

Of the monopolar devices disclosed herein, device 5c has been found to be particularly useful to a surgeon performing a liver resection. Once the outer capsule of the liver is scored with a dry bovie blade along the planned line of resection, the distal tip of tip portion 45 is painted back and forth along the line, with radio frequency power and the flow of fluid 24 on, resulting in coagulation of the liver parenchyma. Once the tissue is coagulated under and around the electrode surface 42 and, as the device 5c enters crevice 97 as shown in FIG. 22, surfaces 40 and 42 of electrode 25 are used to blunt dissect the coagulated parenchyma. Blunt dissection of the coagulated parenchyma is performed by continuous abrading or splitting apart of the parenchyma with the substantially the same back and forth motion as coagulation and with the device 5c being held substantially in the same orientation as for coagulation of the liver parenchyma. However, with blunt dissection, the surgeon typically applies more force to the tissue. In various embodiments, once the liver parenchyma is coagulated, blunt dissection may be performed with or without the radio frequency power (i.e., on or off) and/or with or without the presence of fluid 24.

Figure 25:
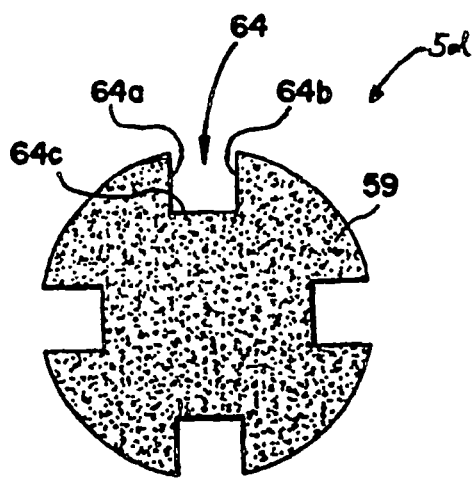
FIG. 25 is a schematic close up cross-sectional view of a porous electrode with recesses.

As shown in FIG. 25, in another embodiment of the electrosurgical device of the present invention, as shown at reference character 5d in FIG. 25, the walls 64a, 64b of recess 64, surface 48 of the shank portion 46, and/or the surfaces of the neck portion 56 of electrode 25 may be porous and connected by a plurality of tortuous pathways 59 in the porous material. Consequently, rather than flowing out of recess 64 from a direct fluid outlet opening 55, which may be occluded by tissue 32, the fluid 24 may exit indirectly from recess 64 by first flowing through tortuous pathways 59 of electrode 25 from side walls 64a, 64b of the recess 64 and then exit electrode 25 from surface 58, which may be in unoccluded by tissue 32. Alternatively, if adjacent surface 58 of electrode 25 is also occluded by tissue 32, the fluid 24 may continue to flow through tortuous pathways 59 of electrode 25 and exit electrode 25 from a surface 64a, 64b of a recess 64 or surface such as 40, 42, 47 or 58 which may be in unoccluded by tissue 32.

Where electrode 25 comprises a porous material, recess 64 may be either supplemented with or replaced by the plurality of tortuous, interconnected passages 59 formed in the porous material as shown in FIG. 25. All or a portion of the electrodes can be porous according to the invention.

Figure 27:
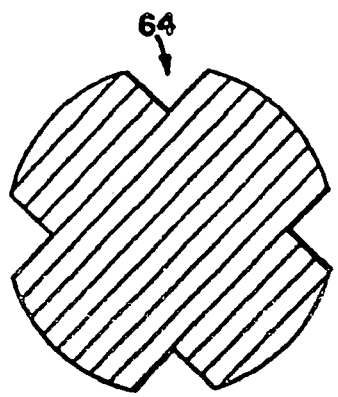
FIG. 27 is a schematic close up cross-sectional view of an electrode with V-shaped recesses.
Figure 26:
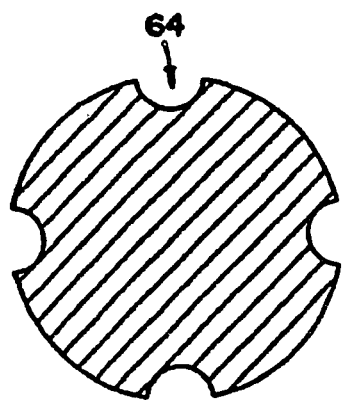
FIG. 26 is a schematic close up cross-sectional view of an electrode with semi-circular recesses.
Figure 28:
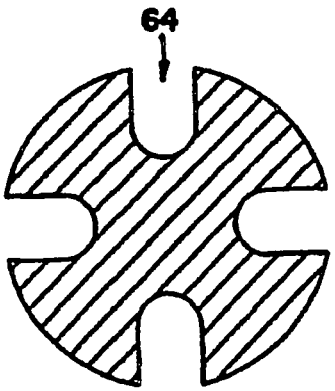
FIG. 28 is a schematic close up cross-sectional view of an electrode with U-shaped recesses.

In other embodiments of the invention, recess 64 may comprise cross-sectional shapes other than rectangular shapes. For example, as shown in FIGS. 26-28 recess 64 comprises a semi-circular shape, a V-shape, or a U-shape respectively, or any combination thereof.

Returning to FIG. 21, in order to facilitate direct fluid communication of recess 64 with lumen 23 of shaft 17, preferably recesses 64 of device 5c are initiated within the confines of shaft 17. In other words, within the cavity 50 of shaft 17 proximal to distal end 53. As indicated above, the use of device 5c, and in particular recesses 64, for the distribution of fluid 24 is generally preferred to the fluid exit holes 93, 94 of device 5b in deep tissue crevices 97 where tissue 32 can occlude fluid flow from the fluid exit holes 93, 94 located in the cylindrical portion 39 of electrode 25. Also, since holes 93, 94 are not presented with a declogging mechanism, such as provided for such as fluid exit holes 26 and 85, holes such as 93, 94 that can be simply occluded by ordinary tissue/electrode contact will sooner or later become irreversibly clogged.

As shown in FIG. 21, with device 5c fluid outlet openings 73 are provided by the structure of electrode 25 (i.e., recesses 64) at the distal end 53 of the shaft 17 which are protected and sheltered from contact and occlusion from surface 22 of tissue 32. Fluid outlet openings 73 of device 5c are protected from occlusion from surface 22 of tissue 32 as the structure of device 5c defining the openings 26 is at least partially configured for non-contact with surface 22 of tissue 32. More specifically, here the structure of the device defining the openings 73 is completely configured for non-contact with surface 22 of tissue 32. Stated another way, the openings 73 are provided on the device 5c at a location removed from the tissue surface 22. Also, as shown, openings 26 are particularly sheltered from occlusion from surface by 22 of tissue 32 by a portion of the shaft 17. Also as shown, openings 73 are formed substantially perpendicular to the surface 22 of tissue 32 and thus turned away from direct contact with surface 22 of tissue 32.

Another tip portion of an exemplary electrosurgical device 5e of the present invention which may be used in conjunction with the system of the present invention is shown at reference character 45 in FIGS. 29-30. As shown, the broadening portion 54 has been eliminated and the cylindrical portion 39 has an equal cross-sectional dimension, here diameter, with the neck portion 56. Conversely, for device 5c, the cylindrical portion 39 has a cross-sectional dimension, there also diameter, greater than the cross-sectional dimension, there also diameter, of the neck portion 56.

Also as shown, the cylindrical portion 39 further comprises a rectilinear cylindrical portion 39a having a rectilinear cylindrical surface portion 40a and a curvilinear cylindrical portion 39b having a curvilinear cylindrical surface portion 40b. As shown, device 5e comprises the shape of a hockey stick. The cylindrical portion 39 for device 5c may be similarly arranged.

Figure 31:
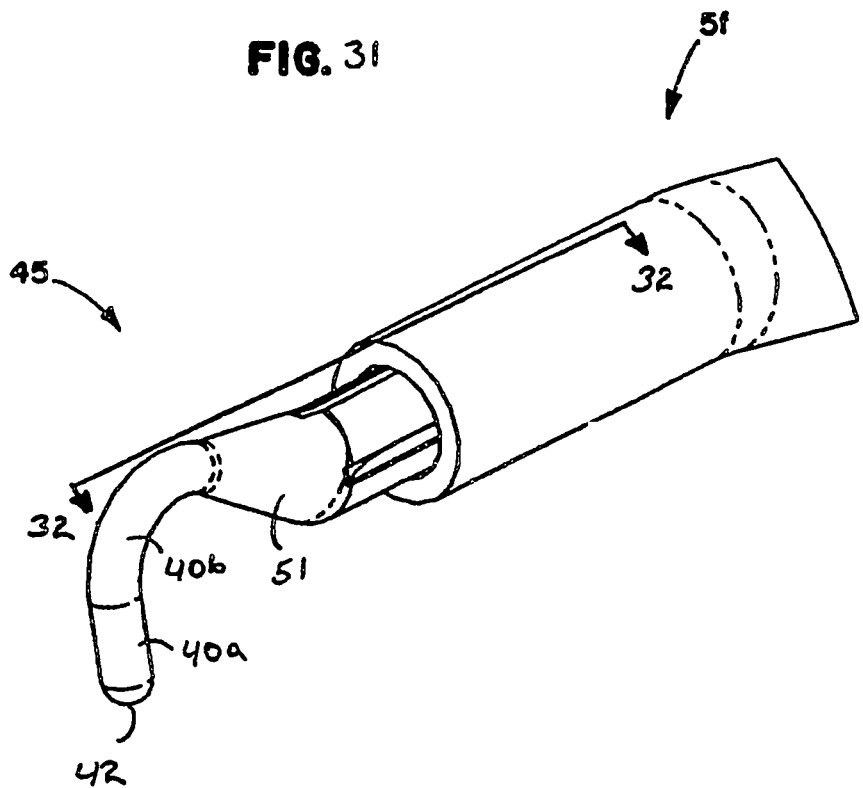
FIG. 31 is a schematic close-up perspective view of an alternative tip portion.
Figure 32:
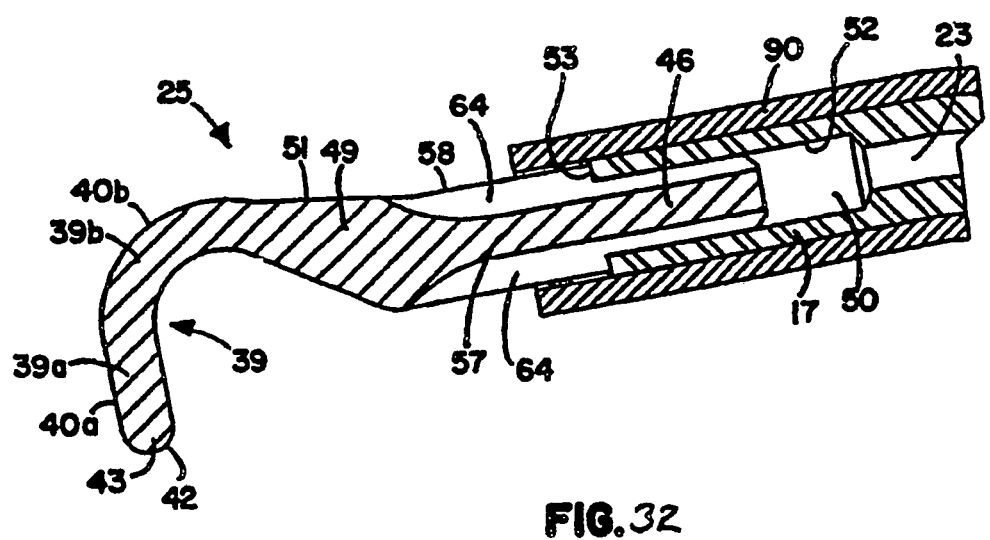
FIG. 32 is a schematic close-up cross-sectional side view of the tip portion of FIG. 31 taken along line 32-32 of FIG. 31.

Another tip portion of an exemplary electrosurgical device 5f of the present invention which may be used in conjunction with the system of the present invention is shown at reference character 45 in FIGS. 31-32. As shown, the cylindrical portion 39 has a cross-sectional dimension, here diameter, less than the cross-sectional dimension, here also diameter, of the neck portion 56. As shown the neck portion 56 includes a narrowing portion 49 with a corresponding narrowing surface portion 51, here both conical.

Also as shown, the cylindrical portion 39 further comprises a rectilinear cylindrical portion 39a having a rectilinear cylindrical surface portion 40a and a curvilinear cylindrical portion 39b having a curvilinear cylindrical surface portion 40b. Furthermore, as shown, the cylindrical portion 39, and more specifically at least one of the rectilinear cylindrical portion 39a and the curvilinear cylindrical portion 39b, comprises a portion of a hook. Preferably, as shown both the rectilinear cylindrical portion 39a and the curvilinear cylindrical portion 39b comprise portions of a hook. As shown, the hook further comprises an L-hook.

Figure 33:
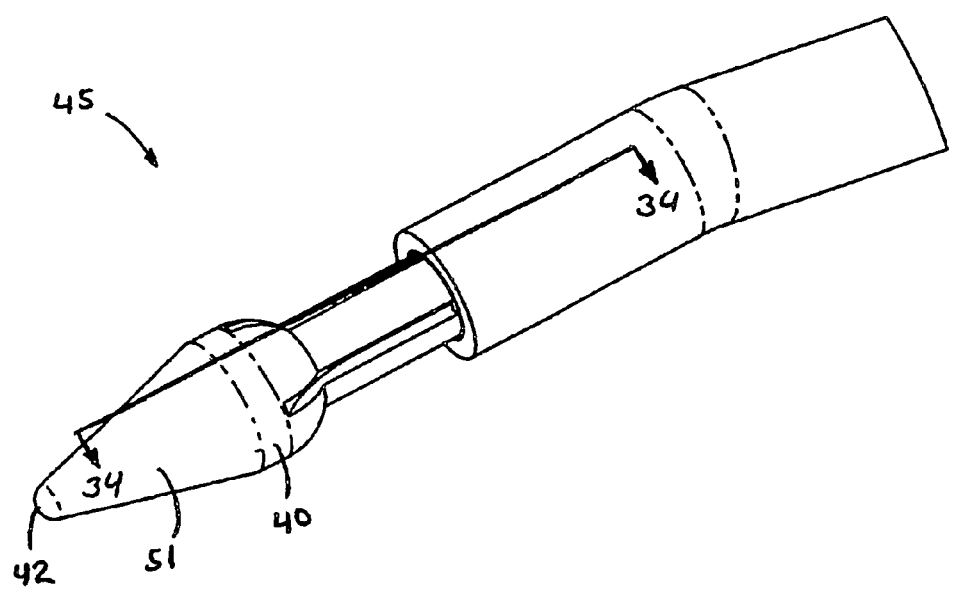
FIG. 33 is a schematic close-up perspective view of an alternative tip portion.
Figure 34:
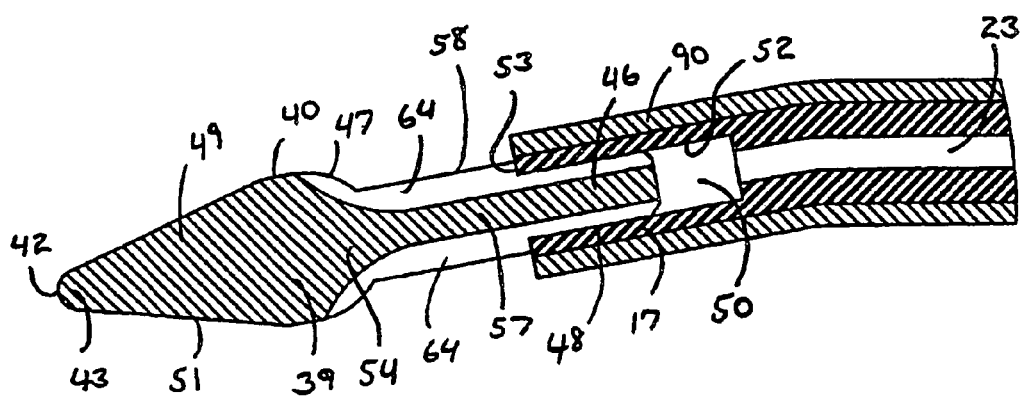
FIG. 34 is a schematic close-up cross-sectional side view of the tip portion of FIG. 33 taken along line 34-34 of FIG. 33.

Another tip portion of an exemplary electrosurgical device 5g of the present invention which may be used in conjunction with the system of the present invention is shown at reference character 45 in FIGS. 33-34. Similar to devices 5c-5f, the separate sleeve 82 of embodiments 5a and 5b has been eliminated from tip portion 45 of device 5g. Consequently, the contact element, still preferably comprising an electrode 25, is assembled directly with the shaft 17. Electrode 25 is preferably assembled (e.g., mechanically connected via a press fit, or interference fit, adjacent the distal end 53 of shaft 17.

As shown in FIGS. 33-34, electrode 25 preferably comprises a spherical portion 43 and a corresponding spherical surface portion 42 located at the distal end of the device 5g, which provided a smooth, blunt contour outer surface. More specifically, as shown, the spherical portion 43 and spherical surface portion 42 further provide a domed, hemisphere (i.e., less than a fill sphere) and hemispherical surface portion comprising preferably about 180 degrees.

Also as shown in FIGS. 33-34, electrode 25 preferably also comprises a narrowing portion 49 and a corresponding narrowing surface portion 51, here both conical, located proximal and adjacent to the spherical portion 43 and spherical surface portion 42, respectively. More preferably, as shown narrowing portion 49 and corresponding narrowing surface portion 51 comprise a conical portion in the form of a concentric cone shape, as opposed to device 5f where the conical portion provided by narrowing portion 49 and a corresponding narrowing surface portion 51 comprises an eccentric cone shape. Thus, in the above manner, spherical portion 43 and spherical surface portion 42 may provide a blunt apex to narrowing portion 49 and a corresponding narrowing surface portion 51, respectively.

Continuing with FIGS. 33-34, electrode 25 preferably also comprises a cylindrical portion 39 and a corresponding cylindrical surface portion 40 located proximal and adjacent to the narrowing portion 49 and narrowing surface portion 51, respectively.

Similar to devices 5c-5f electrode 25 preferably comprises a connector portion, preferably comprising a shank 46, which connects the remainder of electrode 25 to the shaft 17. Among other things, the connector portion of electrode 25 is preferably configured to form a connection with a mating connector portion of the shaft 17. As shown, preferably the shank portion 46 is configured to extend into cavity 50 of shaft 17 which comprises a cylindrical receptacle and provides the mating connector portion for shank 46. More preferably, surface 48 of the shank portion 46 is configured to mate against and form an interference fit with surface 52 of cavity 50 to provide the connection. Also similar to devices 5c-5f, shank portion 46 is preferably cylindrical and located proximal and adjacent to a neck portion 56.

As shown, similar to device 5c, neck portion 56 comprises a cylindrical portion 57 (having a corresponding cylindrical surface portion 58) and a broadening portion 54 (having a corresponding broadening surface portion 47). Here broadening portion 54 and corresponding broadening surface portion 47 are both spherical, and more specifically comprise a domed, hemisphere and hemispherical surface portion comprising preferably about 180 degrees, located proximal and adjacent to the cylindrical portion 39 and cylindrical surface portion 40.

Similar to devices 5c-5f, the cylindrical portion 57 of neck portion 56 of device 5g preferably has a cross-sectional dimension, here diameter, greater than the cross-sectional dimension, here also diameter, of the shank 46. In this manner, in certain embodiments, the proximal end of the neck portion 56 may be located adjacent and in contact with the distal end 53 of shaft 17.

Also similar to devices 5c-5f, preferably electrode 25 comprises at least one recess 64 which provides an elongated fluid flow channel for the distribution of fluid 24. As shown, electrode 25 preferably comprises a plurality of longitudinally directed recesses 64 and, more specifically, four recesses 64 equally spaced 90 degrees around the shank 46 and/or neck portion 56, both proximal of cylindrical portion 39.

Figure 35:
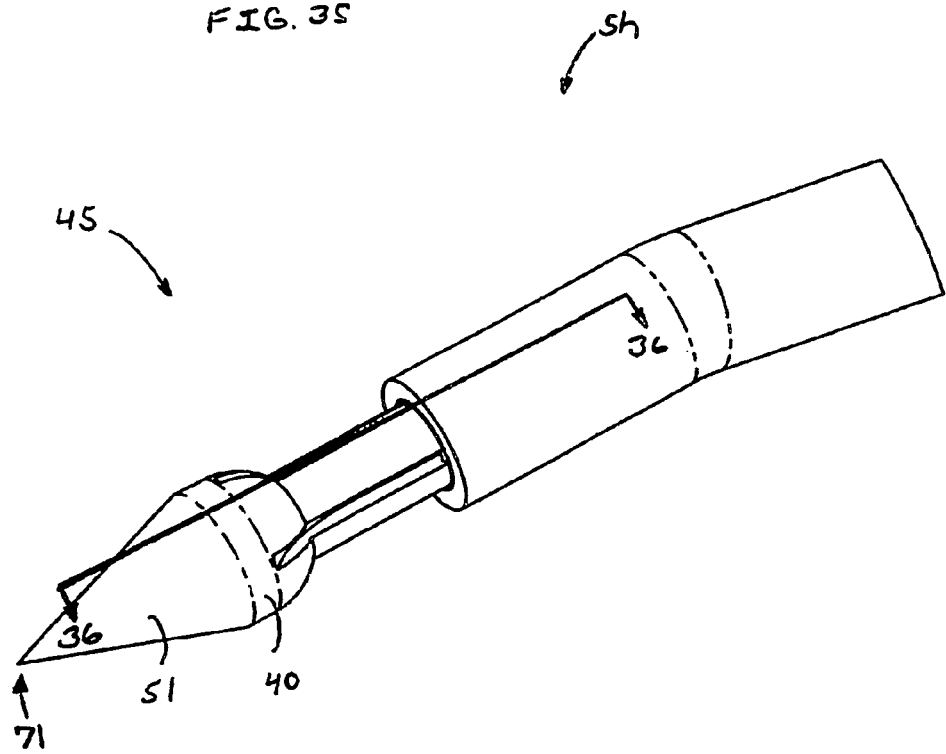
FIG. 35 is a schematic close-up perspective view of an alternative tip portion.
Figure 36:
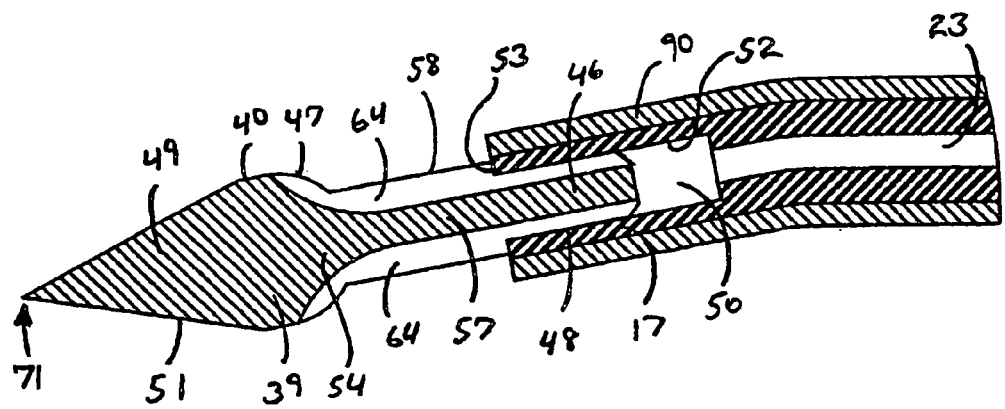
FIG. 36 is a schematic close-up cross-sectional side view of the tip portion of FIG. 35 taken along line 36-36 of FIG. 35.
Figure 37:
FIG. 37 is a schematic close up side view of an alternative cone shape portion of an electrode.
Figure 38:
FIG. 38 is a schematic close up side view of an alternative cone shape portion of an electrode.
Figure 39:
FIG. 39 is a schematic close up side view of an alternative cone shape portion of an electrode.
Figure 40:
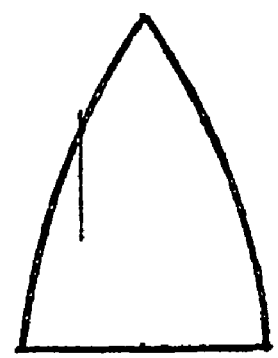
FIG. 40 is a schematic close up side view of an alternative cone shape portion of an electrode.

Another tip portion of an exemplary electrosurgical device 5h of the present invention which may be used in conjunction with the system of the present invention is shown at reference character 45 in FIGS. 35-36. Device 5h is similar to device 5g in all respects except that spherical portion 43 and spherical surface portion 42 have been eliminated and replaced with a distal end sharp point 71.

As shown in FIG. 36, the electrode 25 of device 5b comprises a simple cone. In other embodiments, electrode 25 may comprise other cone shapes. For example, as shown in FIGS. 37-40, the cone shape may comprise an ogive cone shape, an elliptical (prolate hemispheroid) cone shape, a bi-conic cone shape and parabolic series cone shapes, respectively, which all may be defined by mathematical equations as known in the art. Still other cone shapes may include power series cone shapes, Haake series cone shapes, Sears-Haake and Von Karman, which all may be defined by mathematical equations as known in the art.

Certain embodiments of the invention may be particularly configured for bipolar devices. For example, an exemplary bipolar electrosurgical device of the present invention which may be used in conjunction with the system of the present invention is shown at reference character 5i in FIGS. 41-43. With a bipolar device, the ground pad electrode located on the patient is eliminated and replaced with a second electrical pole as part of the device. An alternating current electrical circuit is then created between the first and second electrical poles of the device. Consequently, alternating current no longer flows through the patient's body to the ground pad electrode, but rather through a localized portion of tissue preferably between the poles of the bipolar device.

Figure 41:
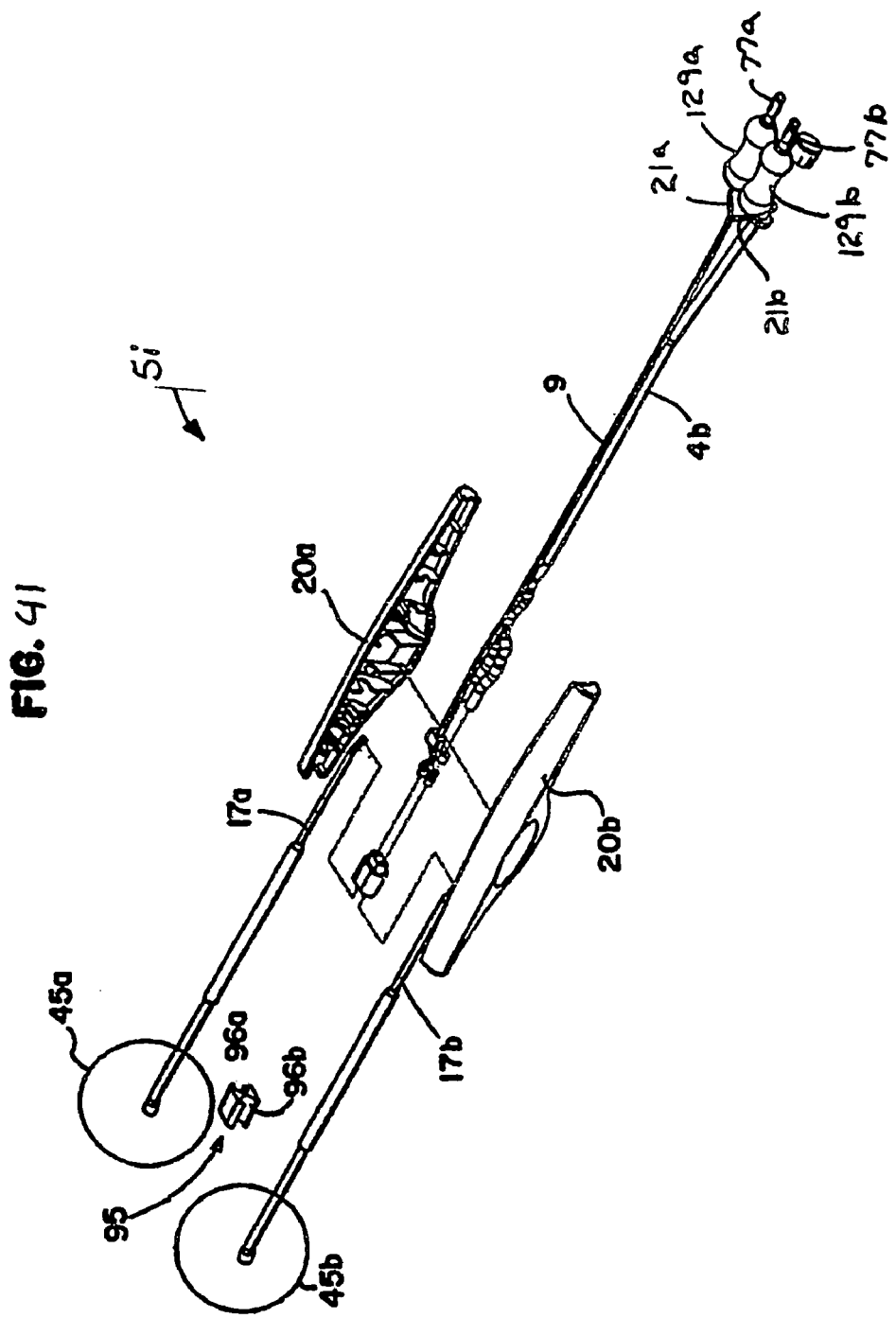
FIG. 41 is a schematic exploded perspective view of an assembly of an alternative electrosurgical device according to the present invention.

In certain embodiments, an exemplary bipolar surgical device of the present invention may comprise, among other things, multiple, substantially parallel, arms. As shown in FIG. 41, electrosurgical device 5i preferably includes two arms comprising rigid, self-supporting, hollow shafts 17a, 17b, a proximal handle comprising mating handle portions 20a, 20b and arm tip portions as shown by circles 45a, 45b. In this embodiment, shafts 17a, 17b preferably comprise thick walled hypo-tubing. In this manner, the shafts 17a, 17b have sufficient rigidity to maintain their form during use of the device without kinking or significant bending.

Preferably the arms of device 5i (comprising shafts 17a, 17b) are retained in position relative to each other by a mechanical coupling device comprising a collar 95 and inhibited from separating relative to each other. Collar 95 preferably comprises a polymer (e.g., acrylonitrile-butadiene-styrene or polycarbonate) and is preferably located on the distal portion of the arms. More preferably, the collar 95 is located proximal the distal ends 53a, 53b of the shafts 17a, 17b. Preferably the collar 95 comprises two apertures 96a, 96b, preferably comprising opposing C-shapes, configured to receive a portion of the shafts 17a, 17b which are preferably snap-fit therein. Once the collar 95 is connected to the shafts 17a, 17b, preferably by a snap-fit connection, the collar 95 may be configured to slide along the length of the shafts 17a, 17b as to adjust or vary the location of the collar 95 on the shafts 17a, 17b. Alternatively, the location of the collar 95 may be fixed relative to the shafts 17a, 17b by welding, for example.

Device 5i comprises a first arm tip portion 45a and a second arm tip portion 45b. As shown, preferably both first arm tip portion 45a and second arm tip portion 45b are each individually configured identical to tip portion 45 of device 5a. As a result, device 5i has two separate, spatially separated (by empty space) contact elements preferably comprising electrodes 25a, 25b.

Figure 42:
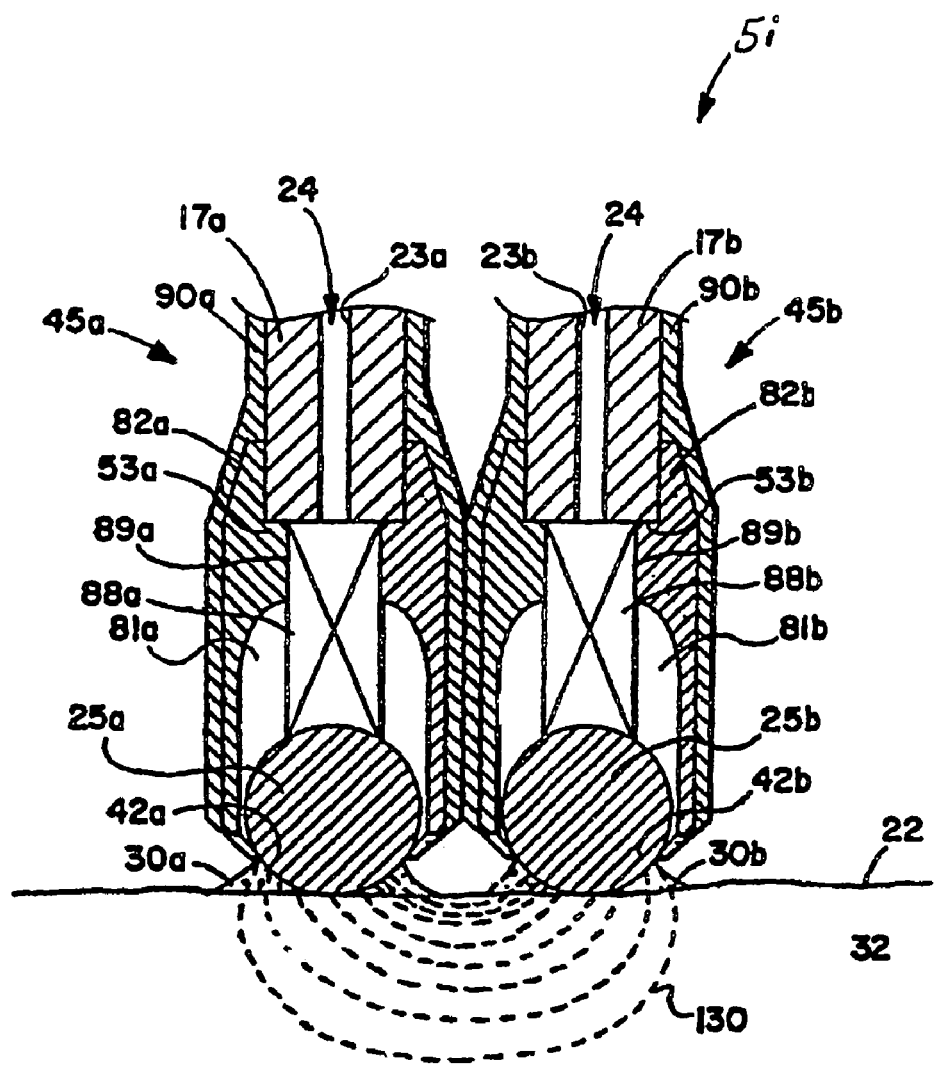
FIG. 42 is a schematic close-up cross-sectional side view of the tip portions of FIG. 41 assembled with a fluid coupling to a tissue surface of tissue.

As shown in FIG. 42, when device 5i is in use electrodes 25a, 25b are laterally spaced adjacent tissue surface 22 of tissue 32. Electrodes 25a, 25b are connected to a source of alternating electrical current and alternating current electrical field is created between electrodes 25a and 25b. In the presence of alternating current, the electrodes alternate polarity between positive and negative charges with current flow from the positive to negative charge.

Similar to device 5a, for device 5i fluid 24 is communicated from a fluid source 1 within the lumens 23a, 23b of the shafts 17a, 17b through the lumens 89a, 89b and cavities 81a, 81b of the sleeves 82a, 82b where it is expelled from around and on the surface 42a, 42b of the electrodes 25a, 25b.

As with use of device 5a, with use of device 5i fluid couplings 30a, 30b preferably comprising discrete, localized webs and more preferably comprising a triangular shaped web or bead portion providing a film of fluid 24 between surface 22 of tissue 32 and electrodes 25a, 25a. When the user of electrosurgical device 5i places electrodes 25a, 25b at a tissue treatment site and moves electrodes 25a, 25b across surface 22 of tissue 32, fluid 24 is expelled around and on surfaces 42a, 42b of electrodes 25a, 25b at the distal ends 83a, 83b of sleeves 82a, 82b and onto surface 22 of tissue 32 via couplings 30a, 30b. At the same time, RF electrical energy, shown by electrical field lines 130, is provided to tissue 32 at tissue surface 22 and below tissue surface 22 into tissue 32 through fluid couplings 25a, 25b.

As with device 5a, the fluid 24, in addition to providing an electrical coupling between the electrosurgical device 5i and tissue 32, lubricates surface 22 of tissue 32 and facilitates the movement of electrodes 25a, 25b across surface 22 of tissue 32. During movement of electrodes 25a, 25b, electrodes 25a, 25b typically slide across the surface 22 of tissue 32, but also may rotate as electrodes 25a, 25b move across surface 22 of the tissue 32. Typically the user of electrosurgical device 5i slides electrodes 25a, 25b across surface 22 of tissue 32 back and forth with a painting motion while using fluid 24 as, among other things, a lubricating coating. Preferably the thickness of the fluid 24 between the distal end surface of electrodes 25a, 25b and surface 22 of tissue 32 at the outer edge of couplings 30a, 30b is in the range between and including about 0.05 mm to 1.5 mm. More preferably, fluid 24 between the distal end surface of electrodes 25a, 25b and surface 22 of tissue 32 at the outer edge of coupling 30a, 30b is in the range between and including about 0.1 mm to 0.3 mm. Also preferably, in certain embodiments, the distal end tip of electrode 25 contacts surface 22 of tissue 32 without any fluid 24 in between.

Figure 43:
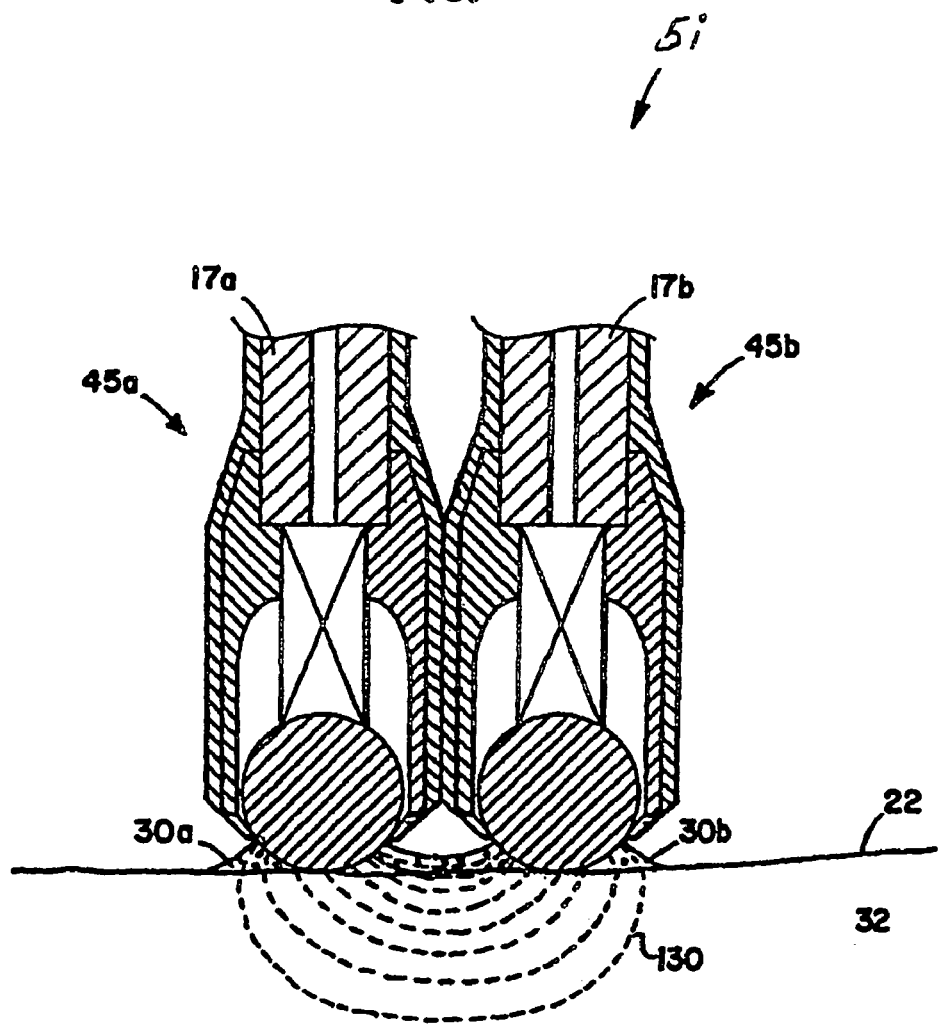
FIG. 43 is a schematic close-up cross-sectional side view of the tip portions of FIG. 41 assembled with an alternative fluid coupling to a tissue surface of tissue.

As shown in FIG. 43, the fluid coupling for device 5i may comprise a conductive fluid bridge 27 between electrodes 25a, 25b which rests on surface 22 of tissue 32 and forms a shunt between electrodes 25a, 25b. Given this scenario, a certain amount of RF energy may be diverted from going into tissue 32 and actually pass between electrodes 25a, 25b via the conductive fluid bridge 27. This loss of RF energy may slow down the process of coagulating tissue and producing the desired hemostasis or aerostasis of the tissue.

In order to counteract the loss of energy through bridge 27, once enough energy has entered bridge 27 to boil fluid 24 of bridge 27, the loss of RF energy correspondingly decreases with the loss of bridge 27. Preferably energy is provided into fluid 24 of bridge 27 by means of heat dissipating from tissue 32.

Thus, where a high % boiling of conductive fluid 24 of bridge 24 is created, the loss of RF energy through bridge 27 may either be reduced or eliminated because all the fluid 24 of bridge 27 boils off or a large fraction of boiling creates enough disruption in the continuity of bridge 27 to disrupt the electrical circuit through bridge 27. Thus, one control strategy of the present invention is to reduce the presence of a conductive fluid shunt by increasing the % boiling of the conductive fluid.

Bipolar device 5i is particularly useful as non-coaptive tissue sealer and coagulator given it does not grasp tissue. Device 5i is particularly useful to surgeons to achieve hemostasis after dissecting through soft tissue as part of hip or knee arthroplasty. The tissue treating portions can be painted over the raw, oozing surface 22 of tissue 32 to seal the tissue 32 against bleeding, or focused on individual larger bleeding vessels to stop vessel bleeding.

Bipolar device 5i is also useful to stop bleeding from the surface of cut bone tissue as part of any orthopaedic procedure that requires bone to be cut. Device 5i is particularly useful for these applications over monopolar device 5a as a much greater surface area 22 of tissue 32 may be treated in an equivalent period of time and with better controlled depth of the treatment.

As is well known, bone, or osseous tissue, is a particular form of dense connective tissue consisting of bone cells (osteocytes) embedded in a matrix of calcified intercellular substance. Bone matrix mainly contains collagen fibers and the minerals calcium carbonate, calcium phosphate and hydroxyapatite. Among the many types of bone within the human body are compact bone and cancellous bone. Compact bone is hard, dense bone that forms the surface layers of bones and also the shafts of long bones. It is primarily made of haversian systems which are covered by the periosteum. Compact bone contains discrete nutrient canals through which blood vessels gain access to the haversian systems and the marrow cavity of long bones. For example, Volkmann's canals which are small canals found in compact bone through which blood vessels pass from the periosteum and connect with the blood vessels of haversian canals or the marrow cavity. Bipolar device 5i disclosed herein may be particularly useful to treat compact bone and to provide hemostasis and seal bleeding vessels (e.g. by shrinking to complete close) and other structures associated with Volkmann's canals and Haversian systems.

In contrast to compact bone, cancellous bone is spongy bone and forms the bulk of the short, flat, and irregular bones and the ends of long bones. The network of osseous tissue that makes up the cancellous bone structure comprises many small trabeculae, partially enclosing many intercommunicating spaces filled with bone marrow. Consequently, due to their trabecular structure, cancellous bones are more amorphous than compact bones, and have many more channels with various blood cell precursors mixed with capillaries, venules and arterioles. Bipolar device 5i disclosed herein may be particularly useful to treat cancellous bone and to provide hemostasis and seal bleeding structures such as the above micro-vessels (i.e. capillaries, venules and arterioles) in addition to veins and arteries. Device 5i may be particularly useful for use during orthopedic knee, hip, shoulder and spine procedures (e.g. arthroplasty).

During a knee replacement procedure, the condyle at the distal epiphysis of the femur and the tibial plateau at the proximal epiphysis of the tibia are often cut and made more planer with saw devices to ultimately provide a more suitable support structure for the femoral condylar prosthesis and tibial prosthesis attached thereto, respectively. The cutting of these long bones results in bleeding from the cancellous bone at each location. In order to seal and arrest the bleeding from the cancellous bone which has been exposed with the cutting of epiphysis of each long bone, bipolar device 5i may be utilized. Thereafter, the respective prostheses may be attached.

Turning to a hip replacement procedure, the head and neck of the femur at the proximal epiphysis of the femur is removed, typically by cutting with a saw device, and the intertrochantic region of the femur is made more planer to provide a more suitable support structure for the femoral stem prosthesis subsequently attached thereto. With respect to the hip, a ball reamer is often used to ream and enlarge the acetabulum of the innominate (hip) bone to accommodate the insertion of an acetabular cup prosthesis therein, which will provide the socket into which the head of the femoral stem prosthesis fits. The cutting of the femur and reaming of the hip bone results in bleeding from the cancellous bone at each location. In order to seal and arrest the bleeding from the cancellous bone which has been cut and exposed, bipolar device 5i may be utilized. Thereafter, as with the knee replacement, the respective prostheses may be attached.

Bipolar device 5i may be utilized for treatment of connective tissues, such as for shrinking intervertebral discs during spine surgery. Intervertebral discs are flexible pads of fibrocartilaginous tissue tightly fixed between the vertebrae of the spine. The discs comprise a flat, circular capsule roughly an inch in diameter and about 0.25 inch thick, made of a tough, fibrous outer membrane called the annulus fibrosus, surrounding an elastic core called the nucleus pulposus.

Under stress, it is possible for the nucleus pulposus to swell and herniate, pushing through a weak spot in the annulus fibrosus membrane of the disc and into the spinal canal. Consequently, all or part of the nucleus pulposus material may protrude through the weak spot, causing pressure against surrounding nerves which results in pain and immobility.

Bipolar device 5i may be utilized to shrink protruding and herniated intervertebral discs which, upon shrinking towards normal size, reduces the pressure on the surrounding nerves and relieves the pain and immobility. Device 5i may be applied via posterior spinal access under surgeon control for either focal shrinking of the annulus fibrosus membrane.

Where a intervertebral disc cannot be repaired and must be removed as part of a discectomy, device 5i may be particularly useful to seal and arrest bleeding from the cancellous bone of opposing upper and lower vertebra surfaces (e.g. the cephalad surface of the vertebral body of a superior vertebra and the caudad surface of an inferior vertebra). Where the disc is removed from the front of the patient, for example, as part of an anterior, thoracic spine procedure, device 5i may also be particularly useful to seal and arrest bleeding from segmental vessels over the vertebral body.

Bipolar device 5i may be utilized to seal and arrest bleeding of epidural veins which bleed as a result of the removal of tissue around the dural membrane during, for example a laminectomy or other neurosurgical surgery. The epidural veins may start bleeding when the dura is retracted off of them as part of a decompression. Also during a laminectomy, device 5i may be used to seal and arrest bleeding from the vertebral arch and, in particular the lamina of the vertebral arch.

As already discuss with respect to FIG. 6, even when general-purpose generator 6 is set to a predetermined "fixed" power output, the actual power delivered from generator 6 may be significantly different if the impedance is outside the range defined by of the generator's low and high impedance cut-off limits.

Also with respect to FIG. 6, the output power is identified as being set to 75 watts in the generator's bipolar mode of operation. With respect to general-purpose generators 6 currently used in the electrosurgical industry, it has been found that a significant portion of the generators only provide an output power of 50 watts in their bipolar mode, with only a few providing an output power of 70-75 watts in bipolar mode. Above 75 watts, a very small number of generators may provide power in their bipolar mode of 100 watts.

As is well known, the maximum output power of a general-purpose generator 6 in its bipolar mode of operation is lower than the maximum output power of the generator in its monopolar mode of operation. One reason for this is that the electrodes commonly associated with a bipolar device are generally in much closer in proximity as compared to the active and return electrodes of a monopolar device, thus reducing the need for greater power. Furthermore, with additional power, use of many prior art dry tip electrosurgical devices only leads to more tissue desiccation, electrode sticking, char formation and smoke generation, thus further obviating the need for additional power.

However, as established above, bipolar device 5i of the present invention inhibits such undesirable effects of tissue desiccation, electrode sticking, char formation and smoke generation, and thus do not suffer from the same drawbacks as prior art dry tip electrosurgical devices.

It has been found that bipolar device 5i is, in certain instances, able to use significantly greater power than the output power current general-purpose generators offer in their accorded bipolar modes. For example, bipolar device 5i may use greater power to treat bone in knee, hip, shoulder and spine surgeries where blood loss would traditionally be particularly high thus necessitating a blood transfusion.

General-purpose generators may offer significantly greater output power than 75 watts when set in their monopolar modes. For example, in monopolar "cut mode", the maximum power output of the generator is typically in the range of 300 watts. However, in monopolar cut mode the voltage and preferred impedance ranges are much greater than in bipolar mode. For example, with respect to impedance, an exemplary low impedance cut-off for a monopolar cut mode is about 200 ohms while an exemplary low impedance cut-off for bipolar mode is about 25-50 ohms.

In order to reduce monopolar voltage and impedance ranges to desirable levels for bipolar use, a transformer may be placed in series circuit configuration between the electrodes of bipolar device 5i and the monopolar mode power output of the generator 6.

Figure 45:
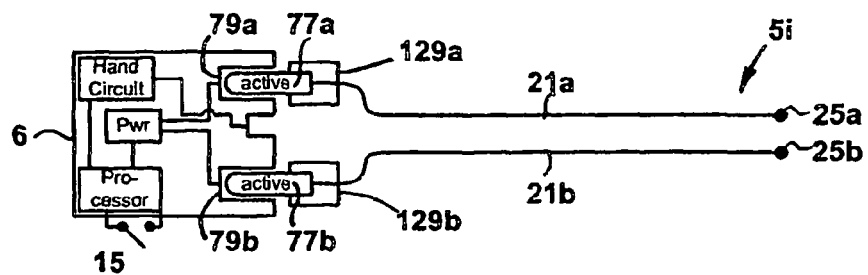
FIG. 45 is a block diagram of an electrical configuration for a generator and a bipolar device without a hand switch.

As shown in FIG. 41, without a transformer, cable 9 of bipolar device 5i may ordinarily comprise two insulated wires 21a, 21b connectable to generator 6 via two banana (male) plug connectors 77a, 77b connecting directly to (female) plug receptacles 79a, 79b of the generator 6 (shown in FIG. 45). As shown in FIG. 41, the banana plug connectors 77a, 77b are each assembled with wires 21a, 21b within individual housings 129a, 129b which are not connected relative to one another and may be referred to as "loose leads". Consequently, in this embodiment, the banana plug connectors 77a, 77b are independently movable relative to one another. An exemplary electrical configuration established between banana plug connectors 77a, 77b of device 5i and banana plug receptacle connectors 79a, 79b of generator 6 is further illustrated in FIG. 45. From the above, it should be understood that the use of plug connectors and receptacle connectors, is merely exemplary, and that other types of mating connector configurations may be employed.

Figure 57:
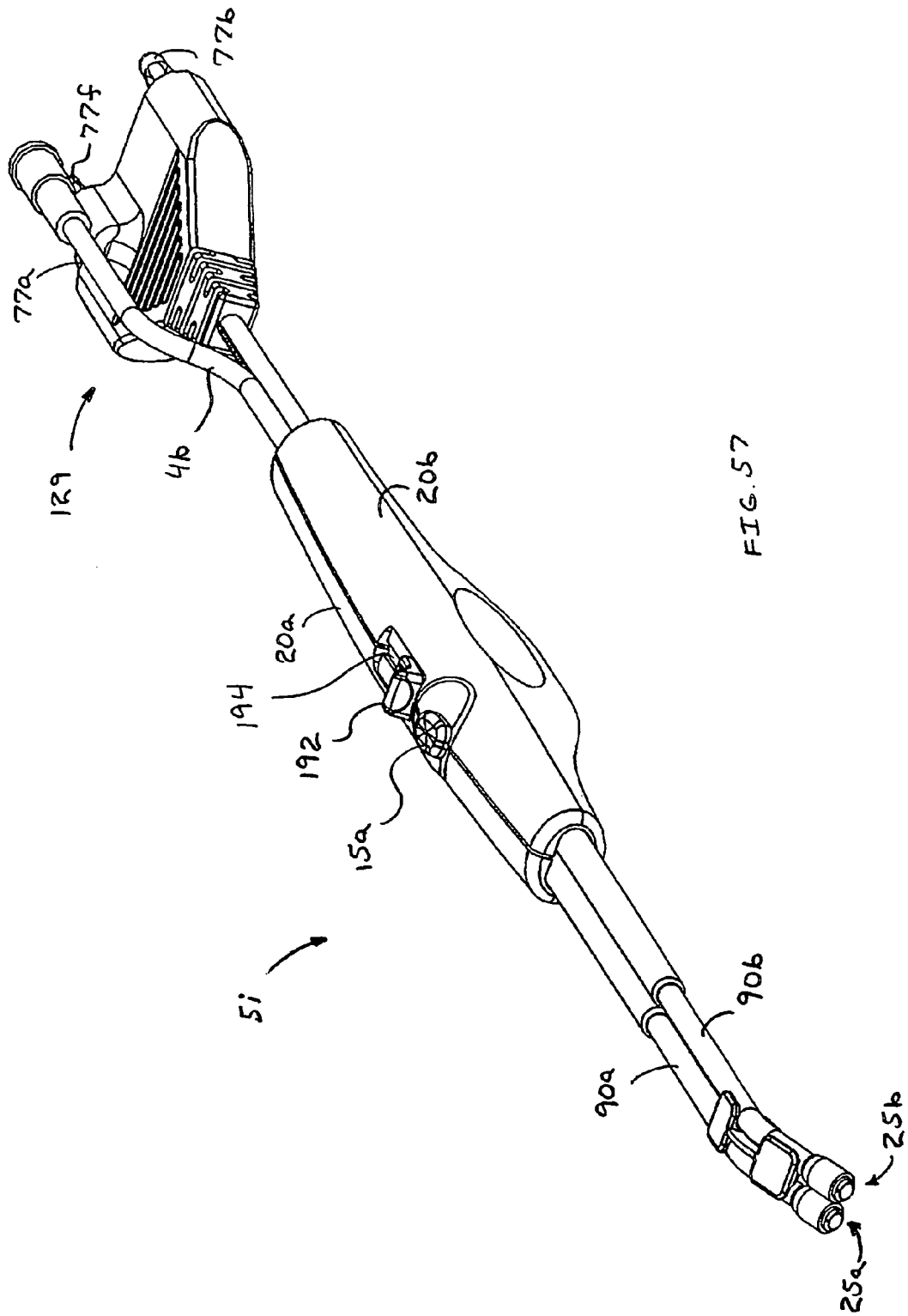
FIG. 57 is a schematic perspective view of an alternative electrosurgical device according to the present invention.

However, with the introduction of a transformer 310 to convert monopolar output power to voltage and impedance ranges associated with bipolar output power, preferably the wires 21a, 21b, plug connectors 77a, 77b and transformer 310 are all assembled and provided in a single, common housing similar to housing 129 shown in FIG. 9, and better shown in FIG. 57. In contrast to the previous embodiment, in this embodiment the plug connectors are held in a fixed, predetermined position relative to one another. In this manner, the plug connectors can be tailored to fit only those generators 6 with receptacle connectors positioned to coincide or match up with the predetermined positions of the plug connectors.

Figure 46:
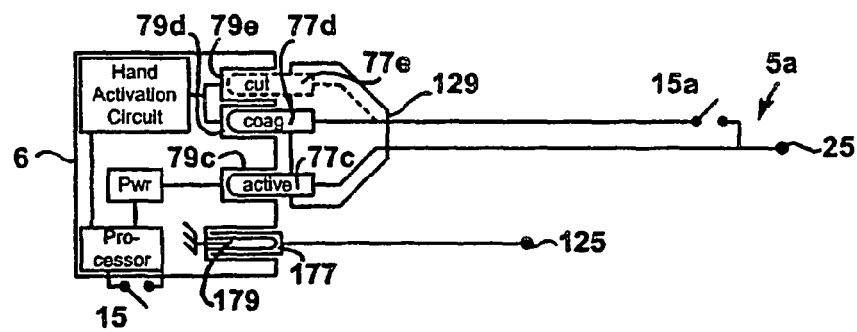
FIG. 46 is a block diagram of an electrical configuration for a generator and a monopolar device with a hand switch.

To further illustrate the above, FIG. 46 illustrates an exemplary electrical configuration which may be associated between monopolar device 5a and generator 6. As shown in FIG. 46, in this embodiment the wiring within plug housing 129 of device 5a is configured such that hand switch 15a may be electrically coupled to the "coagulation mode" hand switching circuitry of generator 6. More specifically, as shown hand switch 15a is electrically coupled to generator 6 upon the insertion of hand switch plug connector 77d of device 5a into hand switch receptacle connector 79d of generator 6.

In addition to plug connector 77d, plug housing 129 also contains power plug connector 77c which may be electrically coupled to the monopolar power receptacle connector 79c of generator 6. As shown, upon insertion of power plug connector 77c into power receptacle connector 79c, electrode 25 is now coupled to the power output of generator 6.

As shown, the finally connection of device 5a to generator 6 comprises ground pad receptacle connector 177 of ground pad 125 being inserted over ground pad plug connector 179 of generator 6.

Plug connectors 77c, 77d are provided in a single common housing 129 to better and more easily direct the plug connectors 77c, 77d to their predetermined targeted plug receptacle connectors 79c, 79d by virtue of being held in a fixed, predetermined position relative to one another by plug housing 129 such that they can only coincide with receptacle connectors 79c, 79d, respectively.

In other embodiments, as indicated by the dotted lines, the wiring within plug housing 129 of device 5a may be configured such that hand switch 15a is coupled to plug connector 77e and plug receptacle 79e, in which case hand switch 15a is now electrically coupled to the monopolar "cut mode" of generator 6 rather than the coagulation mode.

Figure 47:
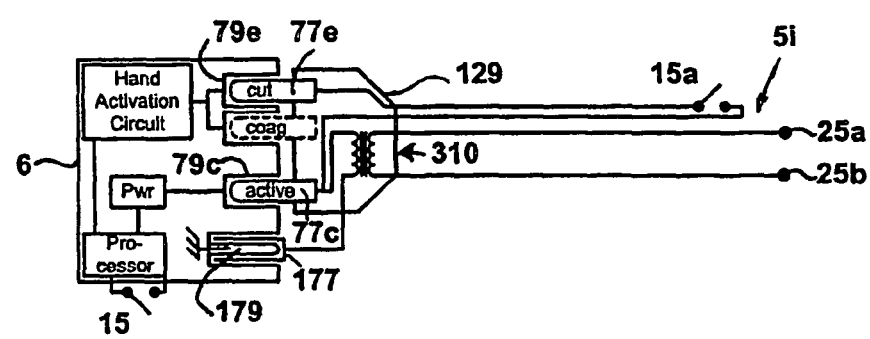
FIG. 47 is a block diagram of an electrical configuration for a generator and a bipolar device with a hand switch and a transformer.
Figure 48:
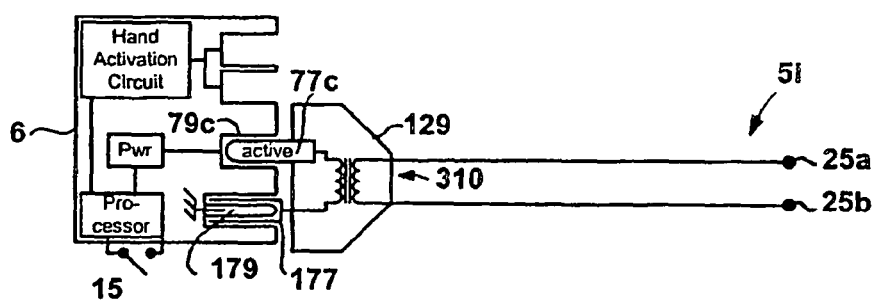
FIG. 48 is a block diagram of an electrical configuration for a generator and a bipolar device without a handswitch and with a transformer.

Now, with use of a bipolar device 5i, as shown in FIG. 47, housing 129 now includes transformer 310 and monopolar device 5a has been replaced with bipolar device 5i, now also including hand switch 15a. Furthermore, as shown, hand switch 15a is coupled to the monopolar cut mode of generator 6 by use of plug connector 77e and plug receptacle 79e. In other embodiments, the hand switch 15a may be eliminated as shown in FIG. 48 and foot switch 15 may be used alone.

The option between monoploar "coagulation mode" hand switching and monopolar "cut mode" hand switching is driven by a number of factors. However, an overriding consideration is often output power. In monopolar coagulation mode, the maximum output power of a general purpose generator is typically about 120 watts, while in monopolar cut mode the maximum output power of the same general purpose generator is typically about 300 watts. For use of the monopolar devices disclosed herein (e.g. 5a, 5c), 120 watts maximum output power associated with coagulation mode has been found to be generally sufficient, thus precluding the need for higher powers associated with cut mode. However, for the bipolar device 5i, when using power provided from the generator's monopolar output, the higher power associated with monopolar cut mode is generally more desirable than the lower power associated with monopolar coagulation mode.

Figure 44:
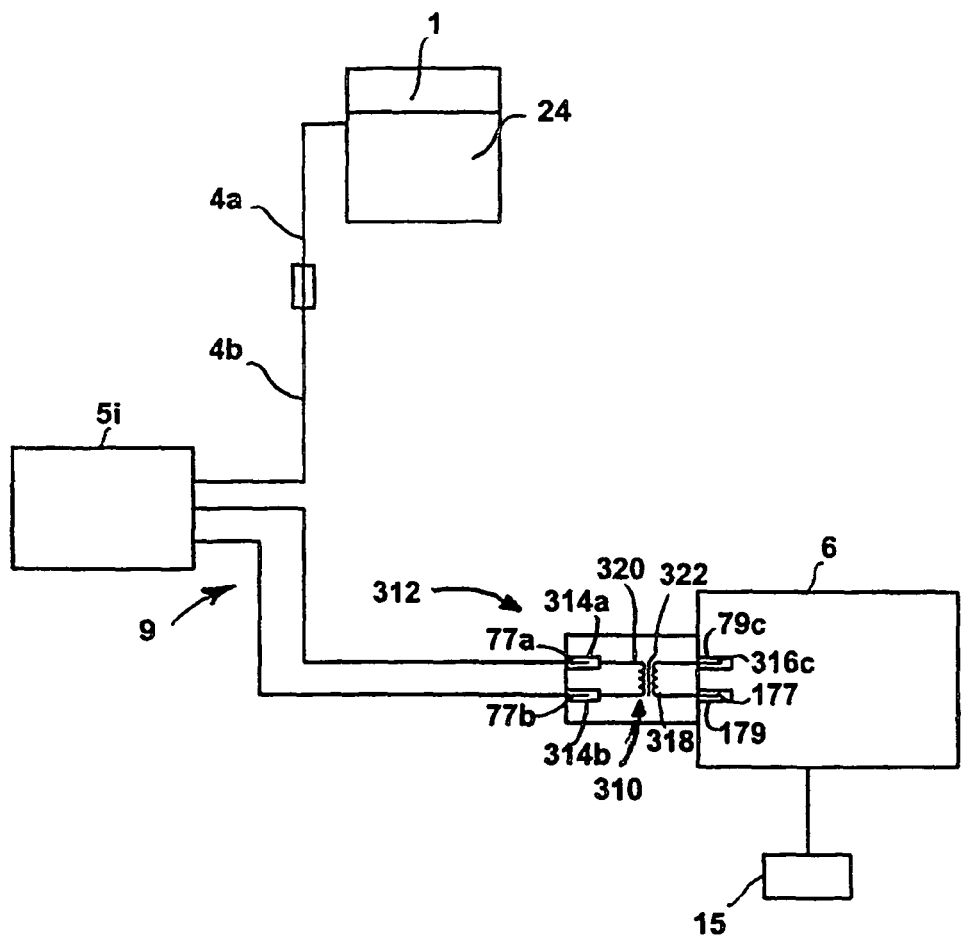
FIG. 44 is a block diagram showing another embodiment of a control system of the invention, and an electrosurgical device.
Figure 49:
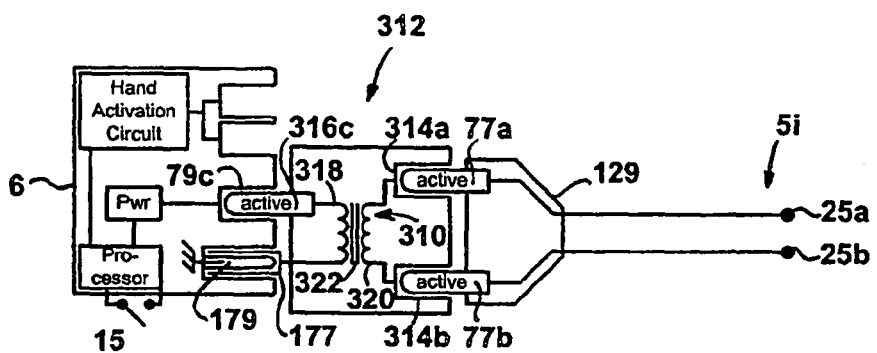
FIG. 49 is a block diagram of an electrical configuration for a generator, a bipolar device without a hand switch, and an adaptor with a transformer therebetween.

In other embodiments, the transformer 310 may be provided as part of an in-line adaptor 312, as shown in FIGS. 44 and 49. In this embodiment, preferably the adapter 312 includes its own receptacle connectors 314a, 314b on one side which are configured to receive plug connectors 77a, 77b of device 5i, and on the opposing side has its own plug connector 316c and ground pad receptacle connector 177 which are configured to connect to receptacle connector 79c and ground pad plug connector 179 of generator 6, respectively. To further illustrate the above, FIG. 49 illustrates an exemplary electrical configuration which may be associated between bipolar device 5i, adapter 312 and generator 6.

Figure 50:
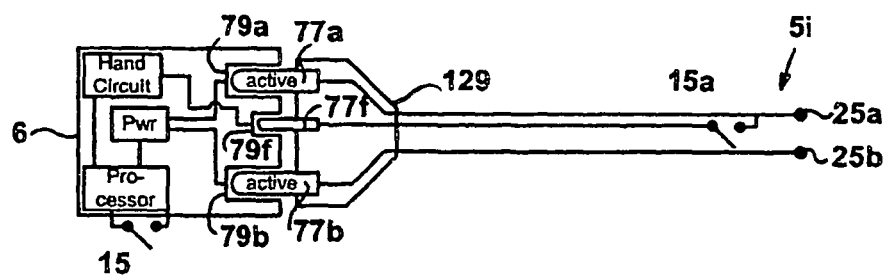
FIG. 50 is a block diagram of an electrical configuration for a generator and a bipolar device with a hand switch.

The adaptor 312 may also be configured to accommodate a bipolar device with a hand switch. Without adaptor 312, FIG. 50 shows an exemplary electrical configuration established between plug connectors 77a, 77b of device 5i and receptacle connectors 79a, 79b of generator 6. In addition, FIG. 50 shows hand switch 15a coupled to the hand switching circuitry of generator 6. More specifically, as shown hand switch 15a is electrically coupled to generator 6 upon the insertion of bipolar hand switch plug connector 77f of device 5i into bipolar hand switch receptacle connector 79f of generator 6.

Figure 51:
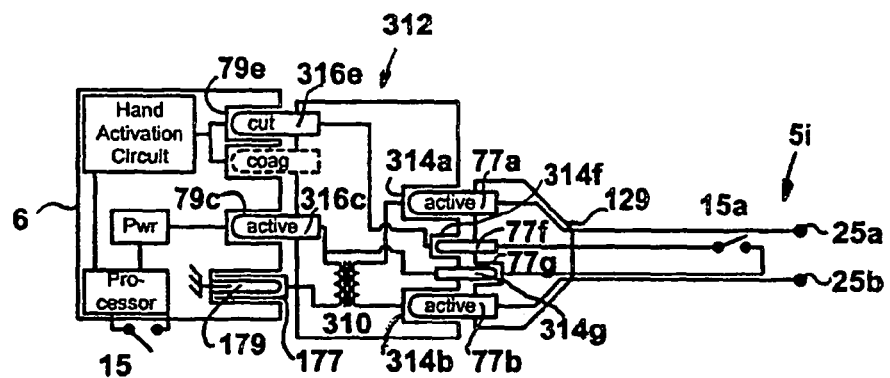
FIG. 51 is a block diagram of an electrical configuration for a generator, a bipolar device with a hand switch, and an adaptor with a transformer therebetween.
Figure 52:
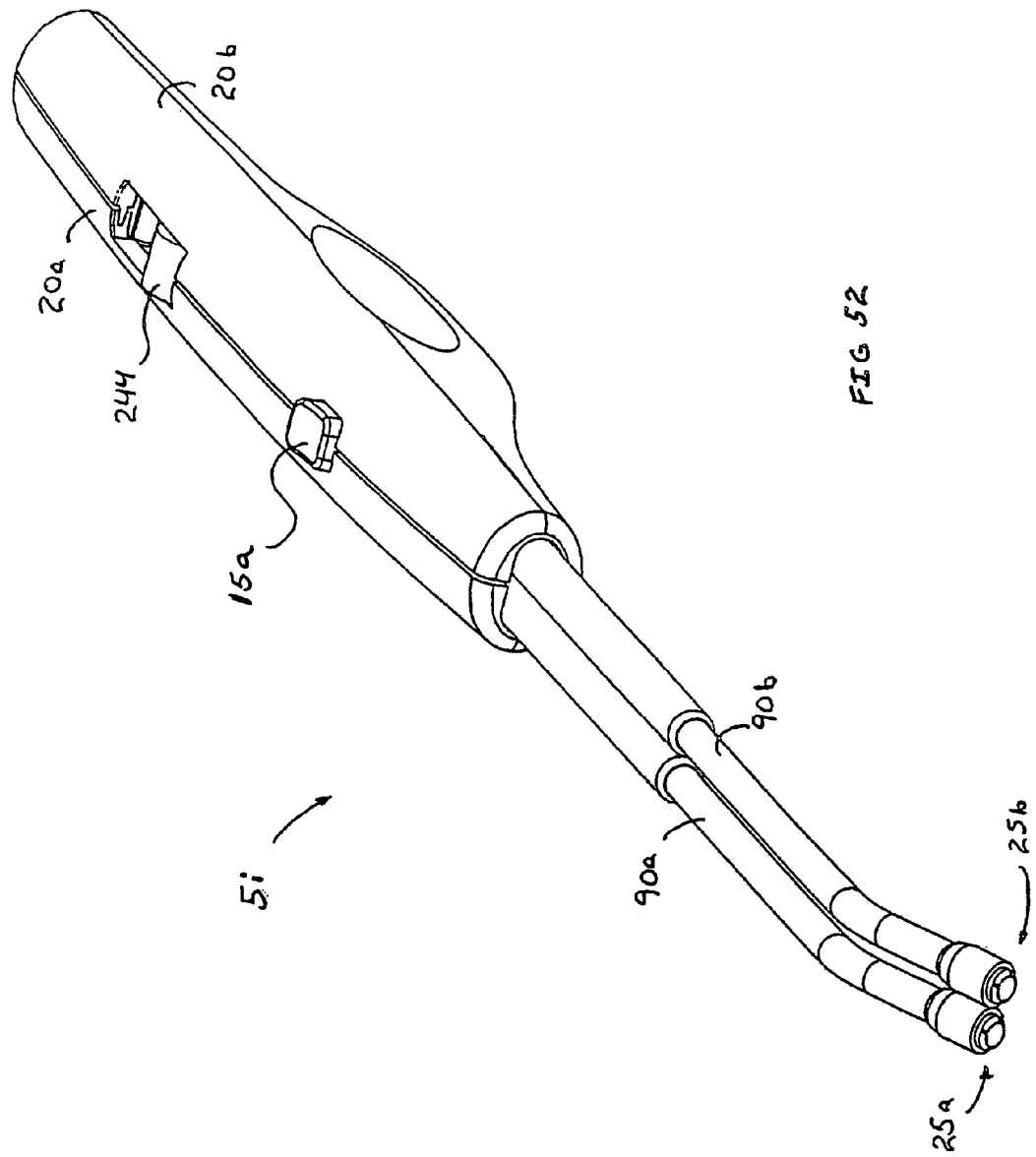
FIG. 52 is a schematic perspective view of an alternative electrosurgical device according to the present invention.
Figure 53:
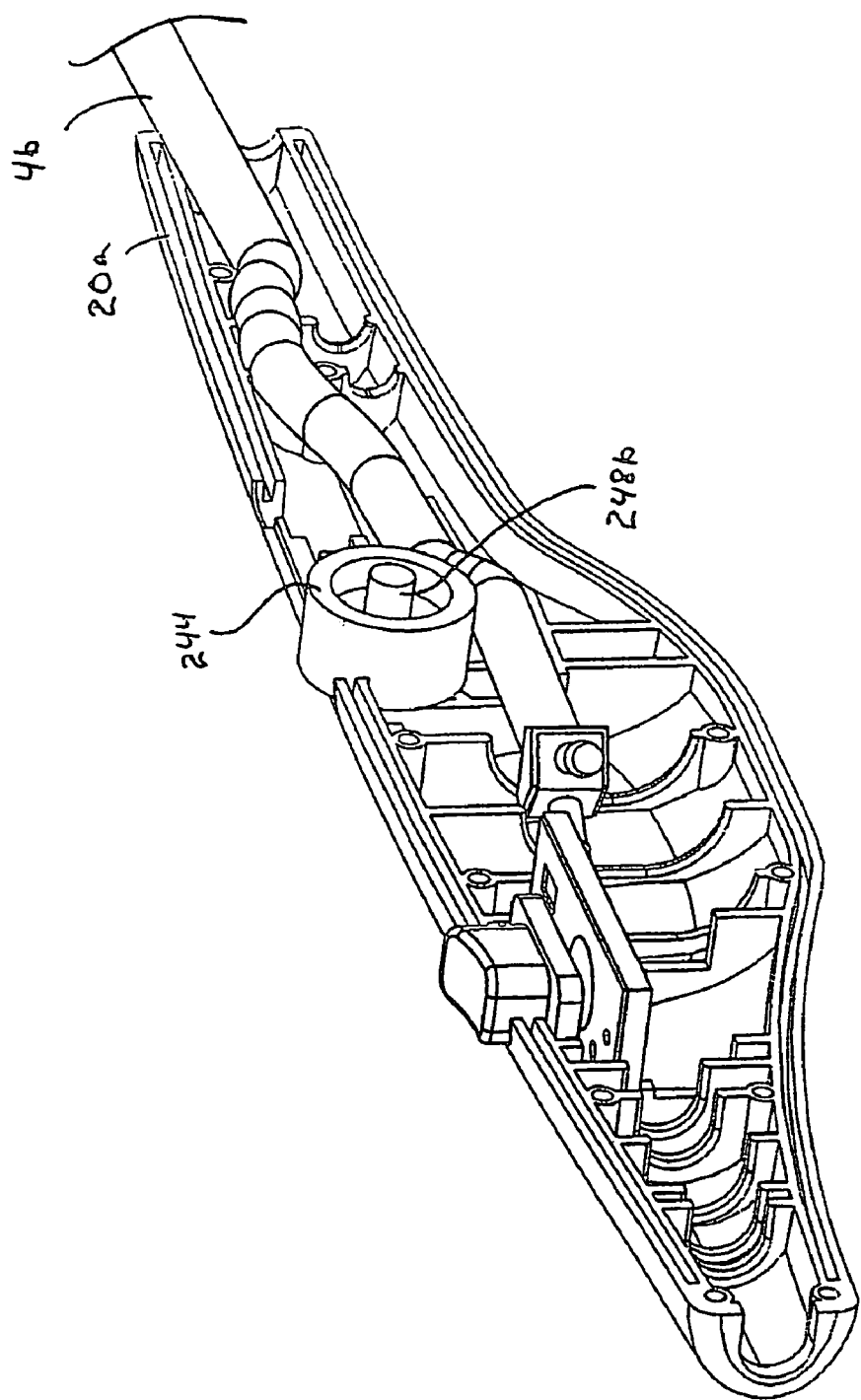
FIG. 53 is a schematic perspective view of a handle portion of the device of FIG. 52 assembled with various components.

With adaptor 312, as shown in FIG. 51 and as with the earlier embodiment, preferably the adaptor 312 includes its own receptacle connectors 314a, 314b on one side which are configured to receive plug connectors 77a, 77b of device 5i, and on the opposing side has its own plug connector 316c and ground pad receptacle connector 177 which are configured to connect to receptacle connector 79a and ground pad plug connector 179 of generator 6, respectively. Furthermore, adaptor 312 has its own bipolar hand switch receptacle connector 314f on one side configured to mate with the bipolar hand switch plug connector 77f of device 5i, and on the opposing side has its own monopolar hand switch plug connector 316e configured to connect to monopolar "cut mode" hand switch receptacle connector 79e of generator 6. Finally, in order to establish the remaining link between the hand switch circuitry and the monopolar power output, the adaptor 312 has a hand switch plug connector 314g configured to mate with hand switch receptacle connector 77g of device 5i.

As shown in FIG. 51, bipolar device 5i now includes four connectors (i.e. 77a, 77b, 77f, 77g) when adaptor 312 is used rather than just the three connectors (i.e. 77a, 77b, 77f) associated with FIG. 50. Connector 77g is added to provide a connection, when mated with connector 314g of adaptor 312, to plug connector 316c which bypasses transformer 310. This is required as the hand switch circuitry of generator 6 typically utilizes direct current (DC) rather than the alternating current (AC) associated with the power circuitry. Consequently, since continuous DC will not cross between the primary coil 318 and secondary coil 320 of transformer 310, this fourth connection is required.

Turning to the specifics of transformer 310, preferably the transformer 310 comprises primary and secondary coils 318, 320 comprising #18 magnet wire wound on a toroidal shaped, magnetic core 322. More preferably the core 322 comprises a ferromagnetic core and even more preferably a ferrite core. Preferably the ferrite has an amplitude permeability in the range of 500μ to 5,000μ and more preferably of about 2,000μ. More preferably, the ferrite comprises ferrite material no. 77. Preferably the core has a 1.4 inch outside diameter, a 0.9 inch inside diameter and a 0.5 inch thickness which is available from Coil Winding Specialists.

For a perfect transformer, that is, a transformer with a coefficient of coupling (k) equal to 1, the impedances can be described as follows:

$$Z_p = Z_s(N_p/N_s)^2 \qquad (8)$$

where:

$Z_p$=Impedance looking into the primary terminals from the power source;
$Z_s$=Impedance of load connected to secondary;
$N_p$=Number of turns (windings) for primary coil; and
$N_s$=Number of turns (windings) for secondary coil Based a primary impedance $Z_p$=200 ohms and a secondary impedance of 25-50 ohms, the transformer 310 should be a step-down transformer with a turns ratio, $N_p/N_s$, in the range between and including about 3:1-2:1, respectively, and preferably about 2.5:1. This will result in power being provided to the tissue in monopolar mode at much lower impedances (i.e. 25-50 ohms) than typically required for use of the generator's monopolar mode (i.e. 200 ohms).

Turning to voltage, the high impedance cut-off for bipolar mode at 75 watts occurs at about 300 ohms, with the power remaining substantially unchanged between 25 ohms and 300 ohms. Thus, based on Ohm's law, for 75 watts ohms and 300 ohms, the voltage before power begins to drop in bipolar mode is about 150 RMS volts. This now becomes the targeted voltage from the monopolar mode with use of the transformer 310.

The high impedance cut-off for monopolar mode at 150 watts occurs at about 1000 ohms. At 150 watts and 1000 ohms, the voltage in monopolar mode is about 387 RMS volts. With the transformer above, secondary voltage may be described as follows:

$$V_s = V_p(N_s/N_p) \qquad (8)$$

where:

$V_s$=Secondary voltage;
$V_p$=Primary voltage;
$N_p$=Number of turns (windings) for primary coil; and
$N_s$=Number of turns (windings) for secondary coil Based on a primary voltage of 387 RMS volts, and a turns ratio $N_p/N_s$ of 2.5:1, the secondary voltage is 155 RMS volts, which is only slightly greater than the targeted 150 RMS volts. With respect to the number of windings, in one embodiment preferably, the primary coil 318 comprises 40 windings while the secondary coil 320 comprises 16 windings resulting in the turns ratio of 2.5.

Figure 54:
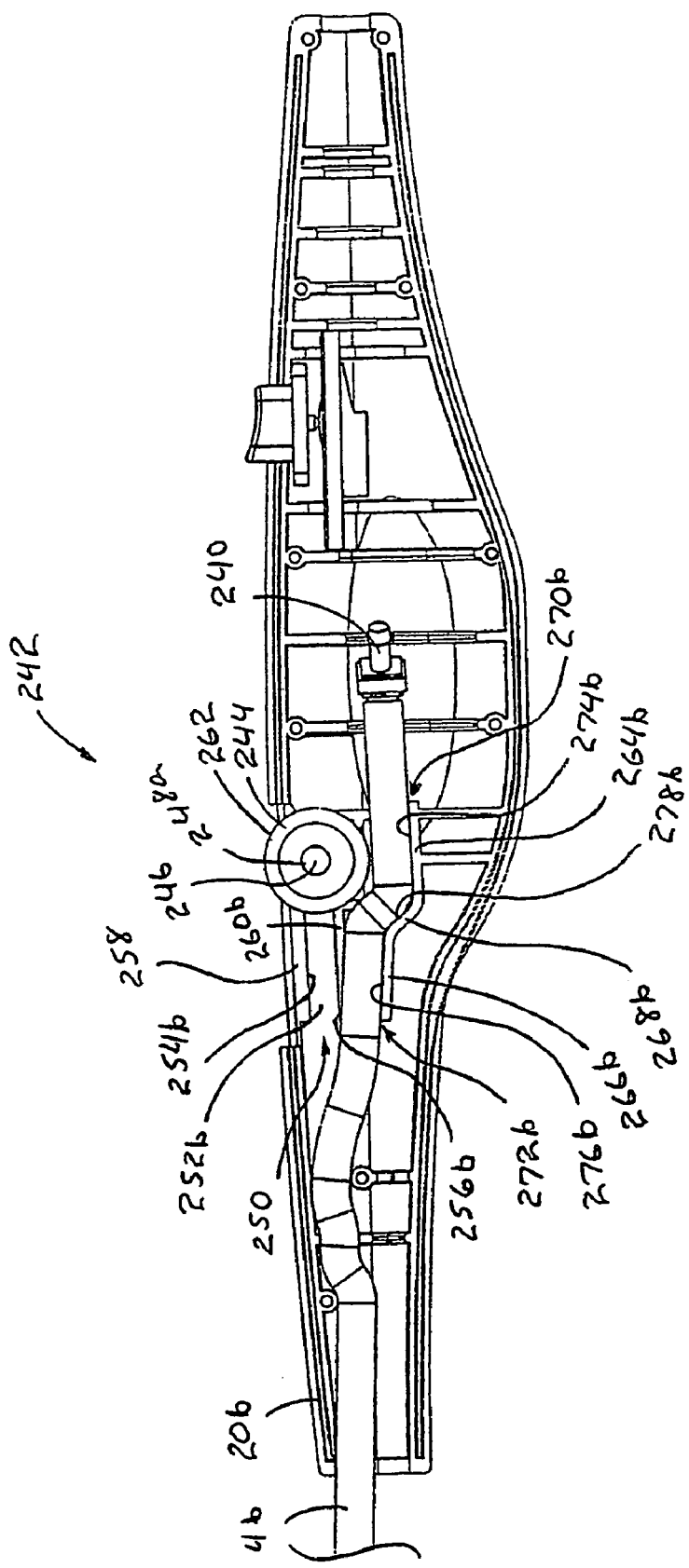
FIG. 54 is a schematic side view of a handle portion of the device of FIG. 52 assembled with various components.
Figure 55:
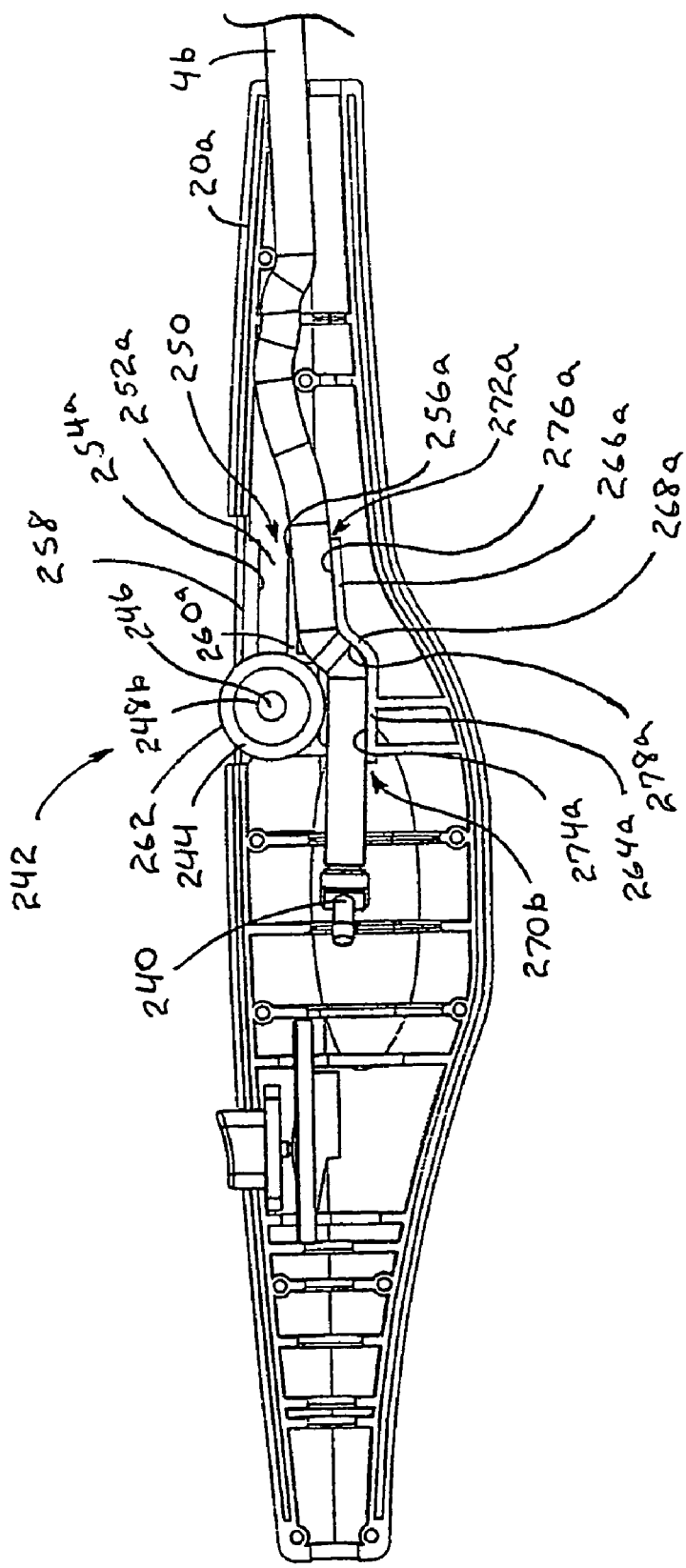
FIG. 55 is a schematic side view of a handle portion of the device of FIG. 52 assembled with various components.
Figure 56:
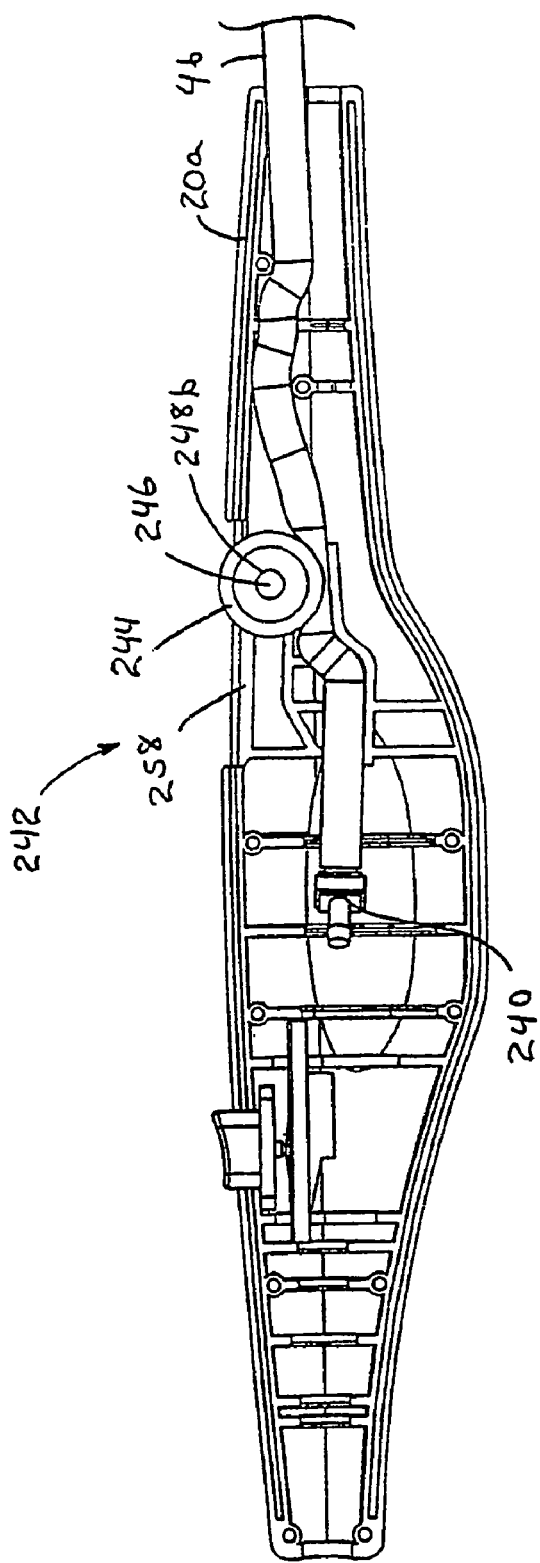
FIG. 56 is a schematic side view of a handle portion of the device of FIG. 52 assembled with various components.

In yet another embodiment, as shown in FIGS. 52-56, electrosurgical device 5i may include a fluid flow control mechanism for turning fluid flow on and off to the tissue treating portion of the device, such as a roller pinch clamp assembly. As best shown in FIGS. 54-56, device 5i includes a roller pinch clamp assembly 242 and, more specifically, an inclined ramp roller pinch clamp assembly (as opposed to a parallel acting clamp).

As best shown in FIGS. 54-55, the clamp assembly 242 includes a housing provided by handles 20a, 20b, a roller wheel 244 having a wheel center axis 246 and a guide pin hub. As shown, the guide pin hub is provided by pair of opposing, integrally formed, cylindrical trunnions 248a, 248b, but may also be provided by a separately formed pin. Trunnions 248a, 248b are contained within and move along a track 250 preferably provided and defined by opposing trunnion channels 252a, 252b formed between wheel upper guide surfaces 254a, 254b and wheel lower guide surfaces 256a, 256b extending longitudinally and parallel inward from the side wall portions of the handles 20a, 20b. As shown, wheel upper guide surfaces 254a, 254b are provided by a lip portion of the handles 20a, 20b which partially define aperture 258 through which roller wheel partially extends while wheel lower guide surfaces 256a, 256b are provided by ribs 260a, 260b.

Handles 20a, 20b also preferably provide tubing guide surfaces 272a, 272b which at least a portion of which provide a clamping surface against which plastic tubing 4b is clamped by roller 244. As best shown in FIGS. 54-55, tubing guide surfaces 272a, 272b are provided by ribs 270a, 270b. In use, fluid line 4b is externally squeezed and compressed between the outer perimeter surface 262 of roller wheel 244 and at least a portion of tubing guide surfaces 272a, 272b. In this embodiment, preferably surface 262 is serrated.

Trunnions 248a, 248b support the movement of roller wheel 244 in two opposing directions, here proximally and distally, along track 250. As best shown in FIGS. 55-56, the separation distance between the outer perimeter surface 262 of roller wheel 244 and tubing guide surfaces 272a, 272b changes throughout the proximal and distal travel of roller wheel 244 along track 250. More specifically the separation distance between the outer perimeter surface 262 of roller wheel 244 and tubing guide surfaces 272a, 272b is greater between the outer perimeter surface 262 of roller wheel 244 and distal end portions 274a, 274b of tubing guide surfaces 272a, 272b provided by distal end portions 264a, 264b of ribs 270a, 270b than between the outer perimeter surface 262 of roller wheel 244 and proximal end portions 276a, 276b of tubing guide surfaces 272a, 272b provided by proximal end portions 266a, 266b of ribs 270a, 270b.

As shown in FIGS. 54-55, when axis 246 of roller wheel 244 is opposing distal end portions 274a, 274b of tubing guide surfaces 272a, 272b, preferably the separation distance is configured such that the tubing 4b may be uncompressed and the lumen of tubing 4b completely open for full flow therethrough. Conversely, as shown in FIG. 56, when axis 246 of roller wheel 244 is opposing proximal end portions 276a, 276b of tubing guide surfaces 272a, 272b preferably the separation distance is configured such that the tubing 4b is compressed and the lumen of tubing 4b is completely blocked so that the flow of fluid through tubing 4b is prevented.

Distal end portions 274a, 274b of tubing guide surfaces 272a, 272b are separated from proximal end portions 276a, 276b of tubing guide surfaces 272a, 272b by transition surfaces 278a, 278b which are provided by transition rib portion 268a, 268b of ribs 270a, 270b. Preferably compression of tubing initially begins between transition surfaces 278a, 278b and the outer perimeter surface 262 of roller wheel 244 and increases as wheel 244 moves proximally along proximal end portions 276a, 276b of tubing guide surfaces 272a, 272b. With this configuration, consideration may be given to eliminating at least that portion of distal end portions 274a, 274b of tubing guide surfaces 272a, 272b that do not contribute to compression of the tubing 4b. However, given that of distal end portions 274a, 274b of tubing guide surfaces 272a, 272b guide tubing 4b to splitter 240, such may not be desirable.

As shown in FIGS. 54-56, both transition surfaces 278a, 278b and proximal end portions 276a, 276b of tubing guide surfaces 272a, 272b provide sloped inclining surfaces proximally along their respective lengths which decreases the separation distance between the outer perimeter surface 262 of roller wheel 244 and the tubing guide surfaces 272a, 272b as the wheel 244 moves proximally. As shown, preferably the transition surfaces 278a, 278b and proximal end portions 276a, 276b of tubing guide surfaces 272a, 272b have different slopes such that the separation distance decreases at a faster rate along transition surfaces 278a, 278b as compared to proximal end portions 276a, 276b of tubing guide surfaces 272a, 272b. In this manner, compression of tubing 4b is non-linear along the length of travel of wheel 244 with a majority of the compression occurring between roller wheel 244 and transition surfaces 278a, 278b. More preferably, the lumen of tubing 4b is completely blocked when roller wheel 244 is compressing the tubing 4b against the proximal portion of transition surfaces 278a, 278b, and the added compression of the tubing 4b along proximal end portions 276a, 276b of tubing guide surfaces 272a, 272b provides an additional safety to assure complete blocking of the lumen even where there are variations in the tubing, such as the size of the lumen.

It should be realized that, due to the slope of the transition rib portion 268a, 268b, as the roller wheel 244 moves proximally relative to transition surfaces 278a, 278b the lumen of tubing 4b is blocked incrementally. Thus, in addition to providing an on/off mechanism, the roller pinch clamp assembly 242 can also be used to regulate the fluid flow rate between two non-zero flow values. It should also be realized that the roller pinch clamp assembly 242 of the device may be used in series conjunction with another roller pinch clamp assembly which is typically provided as part of an IV set (i.e. IV bag, IV bag spike, drip chamber, connecting tubing, roller clamp, slide clamp, luer connector). When used in this manner, the roller pinch clamp assembly of the IV set may be used to achieve a primary (major) adjustment for fluid flow rate, while the roller pinch clamp assembly 242 of the device may be used to achieve a secondary (more precise minor) adjustment for the fluid flow rate.

Figure 58:
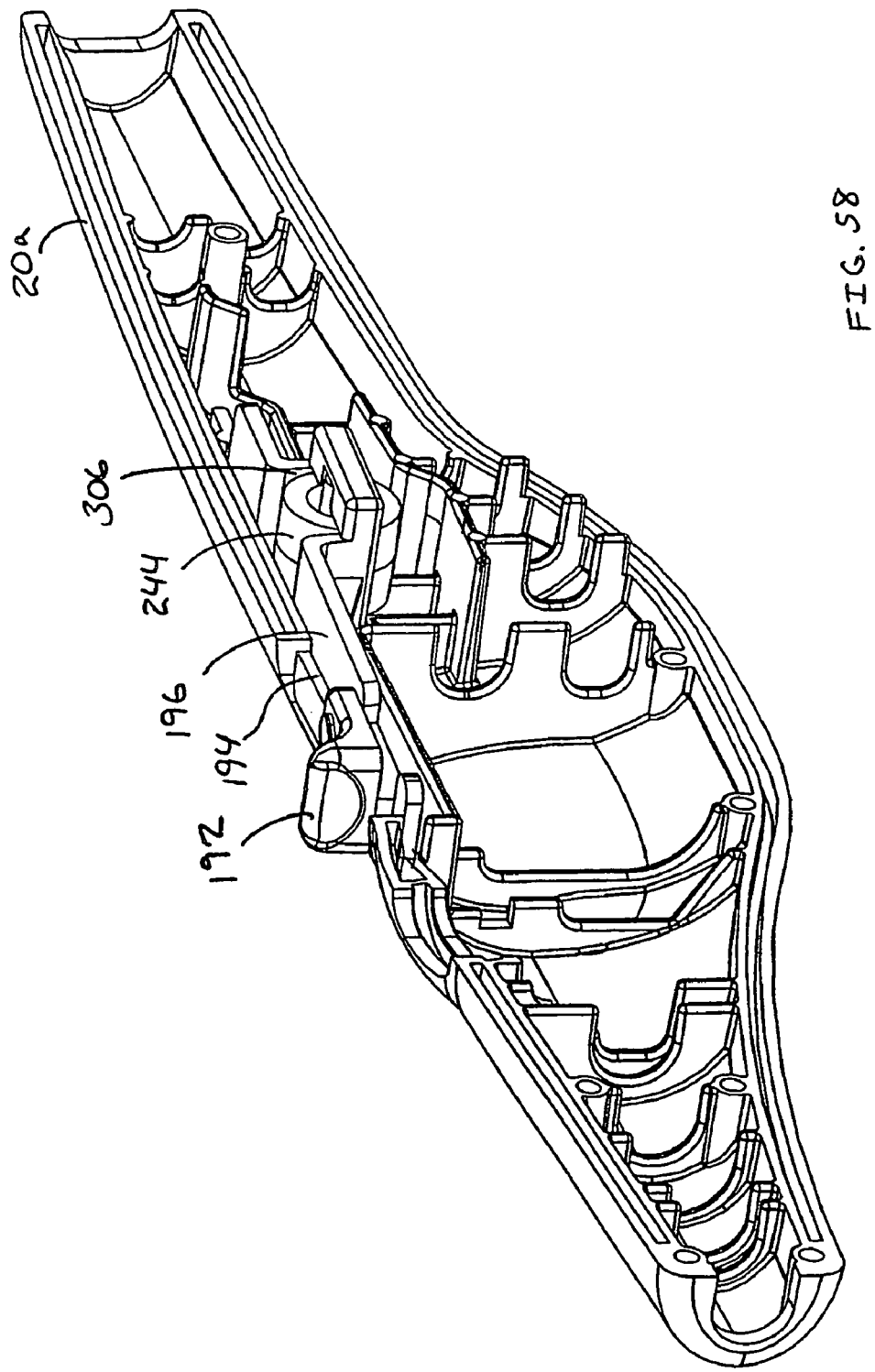
FIG. 58 is a schematic perspective view of a handle portion of the device of FIG. 57 assembled with various components.
Figure 59:
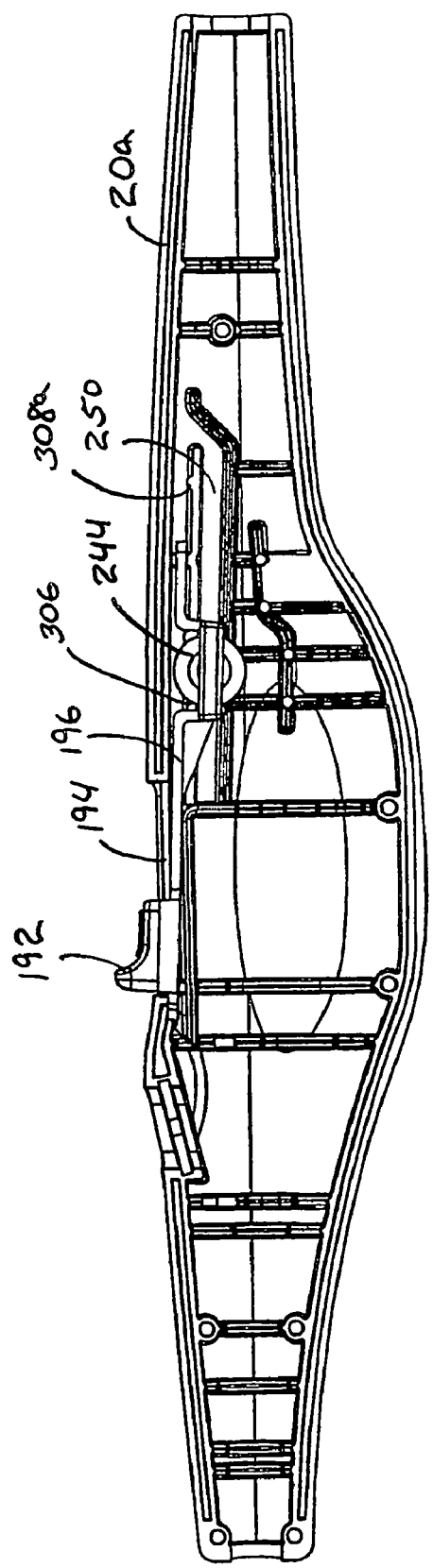
FIG. 59 is a schematic side view of a handle portion of the device of FIG. 52 assembled with various components.

In another embodiment, as shown in FIGS. 57-59 for device 5i, roller wheel 244 of roller pinch clamp assembly 242 may be concealed from view to reduce the possibility of foreign objects (e.g. practitioner's rubber gloves) from entering into the confines of handle 20a, 20b through aperture 258 and getting snagged, for example, between the trunnions 248a, 248b and track 250.

As shown in FIG. 57, roller wheel 244 is concealed from view by handle portions 20a, 20b. As shown, switch button 192 protrudes through an aperture 194 formed in handle portions 20a, 20b. Button 192 is preferably integrally connected via a single piece polymer molding to a proximally extending switch arm 196 which provides a receptacle 306 which contains and holds roller wheel 244.

With use of the fluid flow control mechanism of FIGS. 57-59, in response to button 192 being moved proximally and distally in switch button aperture 194, switch arm 196 moves proximally and distally along track 250, which correspondingly moves roller wheel 244 to compress tubing 4b as discussed above.

As best shown in FIG. 59, preferably the fluid flow control mechanism further comprises a mechanism which may hold the arm 196 in a fixed position while compressing and occluding fluid line 4b. As shown, preferably the locking mechanism comprises detents 308a, 308b (308b not shown) formed in handle portions 20a, 20b which partially receive trunnions 248a, 248b therein to hold arm 196 in a fixed position.

The devices of the present invention may provide treatment of tissue without using a temperature sensor built into the device or a custom special-purpose generator. In a preferred embodiment, there is no built-in temperature sensor or other type of tissue sensor, nor is there any custom generator. Preferably, the invention provides a means for controlling the flow rate to the device such that the device and flow rate controller can be used with a wide variety of general-purpose generators. Any general-purpose generator is useable in connection with the fluid delivery system and flow rate controller to provide the desired power; the flow rate controller will accept the power and constantly adjust the saline flow rate according to the control strategy. Preferably, the generator is not actively controlled by the invention, so that standard generators are useable according to the invention. Preferably, there is no active feedback from the device and the control of the saline flow rate is "open loop." Thus, in this embodiment, the control of saline flow rate is not dependent on feedback, but rather the measurement of the RF power going out to the device.

The use of the disclosed devices can result in significantly lower blood loss during surgical procedures such as liver resections. Typical blood loss for a right hepatectomy can be in the range of 500-1,000 cubic centimeters. Use of the devices disclosed herein to perform pre-transection coagulation of the liver can result in blood loss in the range of 50-300 cubic centimeters. Such a reduction in blood loss can reduce or eliminate the need for blood transfusions, and thus the cost and negative clinical consequences associated with blood transfusions, such as prolonged hospitalization and a greater likelihood of cancer recurrence. Use of the device can also provide improved sealing of bile ducts, and reduce the incidence of post-operative bile leakage, which is considered a major surgical complication.

For purposes of the appended claims, the term "tissue" includes, but is not limited to, organs (e.g. liver, lung, spleen, gallbladder), highly vascular tissues (e.g. liver, spleen), soft and hard tissues (connective, bone, cancellous) and tissue masses (e.g. tumors).

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes.

We claim:

1. An electrosurgical device to treat tissue in a presence of radio frequency power and a fluid provided simultaneously from a distal portion of the device, the device having a proximal end and a distal end and comprising:
a handle;
a shaft extending from the handle, the shaft supporting an electrode tip in rigid relation to the handle and having a distal end;
a fluid passage being connectable to a fluid source of the fluid;
the electrode tip comprising a single metal contact element providing an electrode having a distal portion and a proximal portion, the distal portion of the electrode extending distally beyond the distal end of the shaft, the proximal portion of the electrode being contained within the shaft;
the distal portion of the electrode comprising an electrically conductive cone shaped portion, the cone shaped portion having a circular portion which narrows towards the distal end of the device along an electrically conductive cone shaped surface; and
at least one fluid outlet opening in fluid communication with the fluid passage, wherein the at least one fluid outlet opening is located at the distal end of the shaft and is defined by the distal end of the shaft and a portion of the electrode adjacent the distal end of shaft.

2. The device according to claim 1 wherein:
the at least one fluid outlet opening is arranged to provide the fluid from the fluid source to the electrode.

3. The device according to claim 1 wherein:
at least a portion of the electrically conductive cone shaped surface has a contact angle ($\theta$) with the fluid from the fluid source thereon of less than 90 degrees.

4. The device according to claim 1 wherein:
the at least one fluid outlet opening is defined by an interior surface of the distal end of the shaft and an exterior surface of the portion of the electrode adjacent the distal end of shaft.

5. The device according to claim 4 wherein:
the at least one fluid outlet opening faces in a direction that is substantially perpendicular to a surface of the tissue being treated and is sheltered by the shaft from having direct contact with the tissue being treated.

6. The device according to claim 1 further comprising:
means to shelter the at least one fluid outlet opening from having direct contact with the tissue being treated.

7. The device according to claim 6 wherein: the means to shelter the at least one fluid outlet opening comprises the shaft.

8. The device according to claim 1 further comprising: a plurality of fluid outlet openings.

9. The device according to claim 8 wherein:
the plurality of fluid outlet openings are arranged to provide the fluid from the fluid source around the electrode.

10. The device according to claim 8 wherein:
the plurality of fluid outlet openings are located at the distal end of the shaft and are defined by the distal end of the shaft and the exterior surface of the portion of the electrode adjacent the distal end of shaft.

11. The device according to claim 8 wherein:
the plurality of fluid outlet openings comprise four equally spaced openings located at the distal end of the shaft, each opening being defined by the distal end of the shaft and the exterior surface of the portion of the electrode adjacent the distal end of shaft.

12. The device according to claim 1 further comprising:
at least one recess formed in an exterior surface of the distal portion of the electrode, the at least one recess to provide an elongated fluid flow channel for the fluid from the fluid source to flow distally along the exterior surface of the distal portion of the electrode.

13. The device according to claim 12 further comprising:
a plurality of recesses, each recess to provide a fluid flow channel for the fluid from the fluid source to flow distally along the exterior surface of the electrode.

14. The device according to claim 12 wherein: the at least one recess is in fluid communication with the at least one fluid outlet opening and extends distally from the at least one fluid outlet opening.

15. The device according to claim 12 wherein: the number of recesses is equal to the number of fluid outlet openings.

16. The device of claim 1 wherein:
the electrode further comprises a distal end, and
the distal end of the electrode is blunt.

17. The device of claim 16 wherein:
the cone shaped portion of the electrode is located adjacent to the blunt distal end of the electrode.
18. The device of claim 1 wherein:
the electrode further comprises a distal end, and
the distal end of the electrode is spherical.
19. The device of claim 18 wherein:
the cone shaped portion of the electrode is located adjacent to the spherical distal end of the electrode.
20. The device of claim 18 wherein:
the spherical distal end of the electrode comprises a hemisphere of about 180 degrees.
21. The device of claim 1 wherein:
the cone shaped portion further comprises a concentric cone shaped portion.
22. The device of claim 1 wherein:
the cone shaped portion further comprises an eccentric cone shaped portion.
23. An electrosurgical device to treat tissue in a presence of radio frequency power and a fluid provided simultaneously from a distal portion of the device, the device having a proximal end and a distal end and comprising:
a handle;
a shaft extending from the handle, the shaft supporting an electrode tip in rigid relation to the handle and having a distal end;
a fluid passage being connectable to a fluid source of the fluid;
the electrode tip comprising a single metal contact element providing an electrode, at least a portion of the electrode extending distally beyond the distal end of the shaft;
the portion of the electrode extending distally beyond the distal end of the shaft comprising a neck portion and an enlarged end portion, the enlarged end portion located distal to the neck portion and comprising an electrically conductive cone shaped portion, the cone shaped portion having a circular portion which narrows towards the distal end of the device along an electrically conductive cone shaped surface; and
at least one fluid outlet opening in fluid communication with the fluid passage, wherein the at least one fluid outlet opening is located at the distal end of the shaft and is defined by the distal end of the shaft and an exterior surface of the electrode at a proximal end of the neck portion which is adjacent the distal end of shaft.
24. The device according to claim 23, wherein:
the at least one fluid outlet opening is arranged to provide the fluid from the fluid source to the electrode.
25. The device according to claim 23 wherein:
at least a portion of the electrically conductive cone shaped surface has a contact angle (θ) with the fluid from the fluid source thereon of less than 90 degrees.
26. An electrosurgical device to treat tissue in a presence of radio frequency power and a fluid provided simultaneously from a distal portion of the device, the device having a proximal end and a distal end and comprising:
a handle;
a shaft extending from the handle, the shaft supporting an electrode tip in rigid relation to the handle and having a distal end;
a fluid passage being connectable to a fluid source of the fluid;
the electrode tip comprising a single metal contact element providing an electrode, at least a portion of the electrode extending distally beyond the distal end of the shaft;
the portion of the electrode extending distally beyond the distal end of the shaft comprising a neck portion and an enlarged end portion, the enlarged end portion located distal to the neck portion and comprising an electrically conductive cone shaped portion, the cone shaped portion having a circular portion which narrows towards the distal end of the device along an electrically conductive cone shaped surface;
at least one fluid outlet opening in fluid communication with the fluid passage; and
at least one recess formed in an exterior surface of a proximal end portion of the neck portion of the electrode, the at least one recess being in fluid communication with the at least one fluid outlet opening and providing an elongated fluid flow channel for the fluid from the fluid source to flow distally along the exterior surface of the neck portion of the electrode.
27. The device according to claim 26 wherein:
the neck portion of the electrode includes a shank portion contained within a cavity of the shaft proximal to the distal end of the shaft.
28. The device according to claim 27 wherein:
the at least one fluid outlet opening is located at the distal end of the shaft and is defined by both the interior surface of the cavity and an exterior surface of the shank portion adjacent the distal end of shaft.
29. The device according to claim 26 wherein:
at least a portion of the electrically conductive cone shaped surface has a contact angle (θ) with the fluid from the fluid source thereon of less than 90 degrees.
30. An electrosurgical device to treat tissue in a presence of radio frequency power and a fluid provided simultaneously from a distal portion of the device, the device having a proximal end and a distal end and comprising:
a handle;
a shaft extending from the handle, the shaft supporting an electrode tip in rigid relation to the handle and having a distal end;
a fluid passage being connectable to a fluid source of the fluid;
the electrode tip comprising a single metal contact element providing an electrode, at least a portion of the electrode extending distally beyond the distal end of the shaft;
the portion of the electrode extending distally beyond the distal end of the shaft comprising a neck portion and an enlarged end portion, the enlarged end portion located distal to the neck portion and comprising an electrically conductive cone shaped portion, the cone shaped portion having a circular portion which narrows towards the distal end of the device along an electrically conductive cone shaped surface;
at least one fluid outlet opening in fluid communication with the fluid passage; and
at least one longitudinally extending recess formed in an exterior surface of a roximal end portion of the neck portion of the electrode the at least one longitudinall extending recess bein in fluid communication with the at least one fluid outlet opening and providing an elongated fluid flow channel extending between the distal end of the shaft and the enlarged end portion of the electrode for the fluid from the fluid source to flow distally along the exterior surface of the neck portion of the electrode towards the enlarged end portion of the electrode.
31. The device according to claim 30 wherein:
at least a portion of the electrically conductive cone shaped surface has a contact angle (θ) with the fluid from the fluid source thereon of less than 90 degrees.

32. An electrosurgical device comprising:
a handle;
a shaft extending from the handle, the shaft supporting an electrode tip in rigid relation to the handle;
a fluid passage being connectable to a fluid source of a fluid;
the electrode tip comprising a single metal contact element providing an electrode having an electrically conductive cone shaped portion, the cone shaped portion having a circular portion which narrows towards the distal end of the device along an electrically conductive cone shaped surface;
at least one fluid outlet opening in fluid communication with the fluid passage, the fluid outlet opening arranged to provide the fluid from the fluid source to the electrode; and
at least one recess formed in an exterior surface of a proximal end portion of the electrode contained within a cavity of the shaft proximal to a distal end of the shaft, the at least one recess providing an elongated fluid flow channel in fluid communication with the at least one fluid outlet opening which is defined by the interior surface of the cavity and the exterior surface of the proximal end portion of the electrode.

33. The device according to claim 32 wherein:
at least a portion of the electrically conductive cone shaped surface has a contact angle (θ) with the fluid from the fluid source thereon of less than 90 degrees.

34. A surgical method for treating tissue comprising:
providing tissue having a tissue surface;
providing radio frequency power and a fluid to an electrosurgical device having a distal end portion which simultaneously provides the radio frequency power and the fluid to a tissue treatment site, the distal end portion comprising at least one fluid outlet opening and a single metal contact element providing an electrode having an electrically conductive cone shaped portion, the cone shaped portion having a circular portion which narrows towards the distal end of the device along an electrically conductive cone shaped surface, the electrode having at least one recess formed in an exterior surface thereof, the at least one recess being in fluid communication with the at least one fluid outlet opening and providing an elongated fluid flow channel for the fluid to flow distally along the exterior surface of the electrode;
providing the fluid from the electrosurgical device;
forming a localized fluid coupling with the fluid which couples the tissue surface and the electrode, the fluid coupling localized at the distal end portion of the electrosurgical device;
providing the radio frequency power to the tissue;
moving the electrode of the electrosurgical device along the tissue;
coagulating the tissue; and
blunt dissecting the tissue with the cone shaped portion of the electrode.

* * * * *

UNITED STATES PATENT AND TRADEMARK OFFICE
CERTIFICATE OF CORRECTION

Page 1 of 1

PATENT NO.       : 7,998,140 B2
APPLICATION NO.  : 10/813736
DATED            : August 16, 2011
INVENTOR(S)      : Michael E. McClurken et al.

It is certified that error appears in the above-identified patent and that said Letters Patent is hereby corrected as shown below:

On the Title page, Related U.S. Application Data (63), the line reading:
"2003, application No. 10/813,736, and a" should read --2003, and a--.

In claim 30, at col. 44, line 55, the language reading "exterior surface of a roximal end portion" should read --exterior surface of a proximal end portion--.

In claim 30, at col. 44, line 56, the language reading "at least one longitudinall" should read --at least one longitudinally--.

In claim 30, at col. 44, line 57, the language reading "extending recess bein" should read --extending recess being--.

Signed and Sealed this
Fourteenth Day of February, 2012

David J. Kappos
*Director of the United States Patent and Trademark Office*